(12) United States Patent
Mizuno et al.

(10) Patent No.: US 6,713,634 B2
(45) Date of Patent: Mar. 30, 2004

(54) PYRROLOAZEPINE DERIVATIVES

(75) Inventors: Akira Mizuno, Kyoto (JP); Makoto Shibata, Ashikaga (JP); Tomoe Iwamori, Ibaraki (JP); Tetsuo Shimamoto, Suita (JP); Kyoko Nakanishi, Ibaraki (JP); Norio Inomata, Minoo (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 0 days.

(21) Appl. No.: 10/188,234

(22) Filed: Jul. 3, 2002

(65) Prior Publication Data

US 2003/0166926 A1 Sep. 4, 2003

Related U.S. Application Data

(63) Continuation of application No. 09/801,816, filed on Mar. 9, 2001, now Pat. No. 6,489,473, which is a continuation of application No. 09/312,713, filed on May 17, 1999, now Pat. No. 6,258,805, which is a continuation of application No. 08/875,495, filed as application No. PCT/JP96/03522 on Dec. 2, 1996, now Pat. No. 5,962,448.

(30) Foreign Application Priority Data

Dec. 1, 1995 (JP) .............................. 7-335714
Feb. 9, 1996 (JP) .............................. 8-46928

(51) Int. Cl.$^7$ ........................................... C07D 207/00
(52) U.S. Cl. ..................................... 548/537
(58) Field of Search ...................... 540/521; 548/537

(56) References Cited

U.S. PATENT DOCUMENTS

| | | | |
|---|---|---|---|
| 5,206,239 A | 4/1993 | Mizuno et al. | 514/215 |
| 5,391,731 A | 2/1995 | Mizuno et al. | 514/215 |
| 5,397,780 A | 3/1995 | Mizuno et al. | 514/215 |
| 5,399,557 A * | 3/1995 | Mizuno et al. | 514/215 |
| 5,416,082 A | 5/1995 | Mizuno et al. | 514/215 |
| 5,684,161 A | 11/1997 | Imoto et al. | 548/531 |
| 5,962,448 A | 10/1999 | Mizuno et al. | 514/215 |
| 6,187,772 B1 | 2/2001 | Mizuno et al. | 514/215 |
| 6,211,362 B1 | 4/2001 | Mizuno et al. | 540/521 |
| 6,258,805 B1 | 7/2001 | Mizuno et al. | 514/215 |
| 6,271,223 B1 | 8/2001 | Mizuno et al. | 514/211.1 |

FOREIGN PATENT DOCUMENTS

| | | |
|---|---|---|
| HU | 195510 | 5/1988 |
| HU | P9501619 | 2/1996 |

* cited by examiner

*Primary Examiner*—Bruck Kifle
(74) *Attorney, Agent, or Firm*—Oblon, Spivak, McClelland, Maier & Neustadt, P.C.

(57) ABSTRACT

A method of effecting serotonin-2-receptor antagonism in a mammal in need thereof, which includes administering to the mammal an effective amount of the compound of the formula (I), or a pharmaceutically acceptable salt thereof:

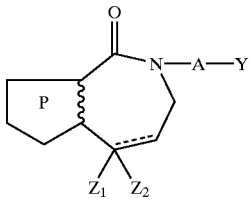

(I)

wherein ring P, the dashed line, A, Y, $Z_1$ and $Z_2$ are defined herein.

20 Claims, No Drawings

PYRROLOAZEPINE DERIVATIVES

TECHNICAL FIELD

This invention relates to novel pyrroloazepine derivatives. More specifically, this invention is concerned with pyrrolo[3,2-c]azepine derivatives, pyrrolo[3,4-c]azepine derivatives and salts thereof, said derivatives and salts having strong serotonin-2 receptor antagonistic action of excellent selectivity and being useful, for example, for the prevention or treatment of ischemic heart diseases such as angina pectoris, arrhythmia, myocardial infarction, congestive heart failure and post-PTCA restenosis, cerebrovascular disturbances such as cerebral infarction and cerebral sequelae after subarachnoid hemorrhage, peripheral circulatory disturbances such as arteriosclerosis obliterans, thromboangiitis obliterans, Raynaud disease and Buerger disease, hypertension; their preparation process; and therapeutics containing them as effective ingredients.

BACKGROUND ART

Serotonin is a compound contained abundantly in platelets, which are a blood component, and in a central nervous system, it acts as a neurotransmitter. In platelets, it is released upon stimulation by thromboxane $A_2$, ADP, collagen or the like, and synergistically acts on release of various platelet aggregation factors through activation of serotonin-2 receptors in the platelets and vascular smooth muscle cells and also on vasoconstriction by norepinephrine through $\alpha_1$ receptors, thereby inducing strong platelet aggregation and vasoconstriction [P. M. Vanhoutte, "Journal of Cardiovascular Pharmacology", Vol. 17 (Supple. 5), S6–S12 (1991)].

Serotonin is also known to potentiate proliferation of vascular smooth muscle cells [S. Araki et al., "Atherosclerosis", Vol. 83, pp.29–34(1990)]. It has been considered that, particularly when endothelial cells are injured as in arteriosclerosis or myocardial infarction, the vasoconstricting action and thrombus forming action of serotonin are exasperated, thereby reducing or even stopping blood supply to myocardial, cerebral and peripheral organs [P. Golino et al., "The New England Journal of Medicine", Vol. 324, No. 10, pp.641–648(1991), Y. Takiguchi et al., "Thrombosis and Haemostasis", Vol. 68(4), pp.460–463 (1992), A. S. Weyrich et al., "American Journal of Physiology", Vol. 263, H349-H358(1992)].

Being attracted by such actions of serotonin or serotonin-2 receptors, various attempts are now under way to use a serotonin-2 receptor antagonist as a pharmaceutical for ischemic diseases of the heart, the brain and peripheral tissues.

Several compounds, led by sarpogrelate, are known to have serotonin-2 receptor antagonistic action. They however do not include anything having the pyrrolo[3,2-c]azepine skeleton or the pyrrolo[3,4-c]azepine skeleton. Those known to have serotonin-2 receptor antagonistic action are accompanied with many problems to be improved in potency, toxicity, side effects or the like. On the other hand, medicines which have anti-serotonin action and $\alpha_1$-blocking action in combination are considered to become extremely effective medicines for the treatment and prevention of hypertension and ischemic heart diseases, because they have possibility to reduce side effects, such as orthostatic hypotension and reflex tachycardia, induced by antihypertensive action on the basis of the $\alpha_1$-blocking action and hypertension is a serious risk factor for ischemic heart diseases.

DISCLOSURE OF THE INVENTION

In view of the foregoing circumstances, the present inventors have proceeded with extensive research, resulting in the finding of pyrroloazepine derivatives which have strong serotonin-2 receptor antagonistic action and low toxicity and less side effects and are useful for the treatment and prevention of ischemic heart diseases, cerebrovascular disturbances and peripheral circulatory disturbances. It has also been found that the compounds according to the present invention include those also having $\alpha_1$-blocking action in combination and that such compounds are useful as antihypertensives or the like having less side effects and are widely usable for the treatment and prevention of circulatory diseases.

The present invention has been completed based on the above described findings. A first object of the present invention is to provide a pyrroloazepine derivative or a salt thereof, said pyrroloazepine derivative being represented by the following formula (I):

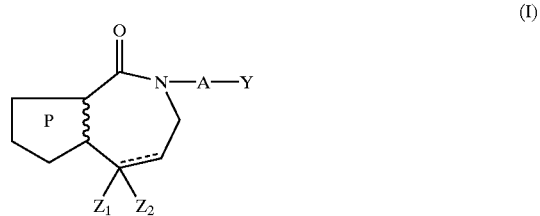

(I)

wherein the ring P represented by:

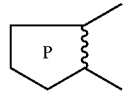

means a pyrrole ring represented by the following structure:

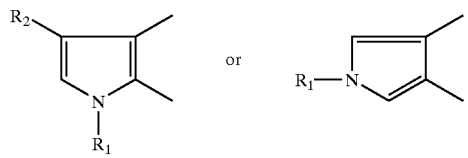

in which $R_1$ represents an alkyl group, a cycloalkyl group, a cycloalkyl-alkyl group, a substituted or unsubstituted aralkyl group or a substituted or unsubstituted aryl group, and $R_2$ represents a hydrogen atom or an alkyl group;

the dashed line indicates the presence or absence of a bond; and, when the bond indicated by the dashed line is present, $Z_2$ is not present and $Z_1$ represents a hydrogen atom but, when the bond indicated by the dashed line is absent, $Z_1$ and $Z_2$ are both hydrogen atoms; $Z_1$ represents a hydrogen atom and $Z_2$ represents a group $OR_3$ in which $R_3$ represents a hydrogen atom, a substituted or unsubstituted alkyl group or a substituted or unsubstituted aralkyl group; $Z_1$ and $Z_2$ both represent groups $SR_4$ in which $R_4$ represents a substituted or unsubstituted alkyl group, a substituted or unsubstituted aralkyl group or a substituted or unsubstituted aryl group; or $Z_1$ and $Z_2$ are combined together to represent an oxygen atom, a group $NOR_5$ in which $R_5$ represents a hydrogen atom, a substituted or unsubstituted alkyl group, a substituted or unsubstituted aralkyl group or a substituted or unsubstituted aryl group, or a group:

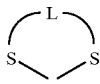

in which L represents a substituted or unsubstituted ethylene group or a substituted or unsubstituted trimethylene group;

A represents an alkylene group, an alkenylene group or an alkynylene group; and

Y represents a group:

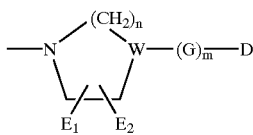

in which W represents CH, C= or a nitrogen atom; and, when W represents CH, m stands for 0 or 1, n stands for 1 or 2, G represents an oxygen atom, a sulfur atom, a carbonyl group, a sulfinyl group, a sulfonyl group, an alkylene group, an alkenylene group, a group;

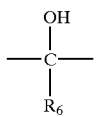

in which $R_6$ represents a substituted or unsubstituted aryl group, a group:

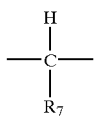

in which $R_7$ represents a hydroxyl group, an alkoxy group or an aralkyloxy group, or a substituted or unsubstituted cyclic or acyclic acetal group; when W represents C=, m stands for 1, n stands for 1 or 2, G represents a group:

in which the double bond is coupled with W and $R_8$ represents a substituted or unsubstituted alkyl group, a substituted or unsubstituted aryl group or a substituted or unsubstituted aralkyl group; when W represents a nitrogen atom, m stands for 0 or 1, n stands for 2 or 3, and G represents a carbonyl group, a sulfonyl group, an alkylene group, an alkenylene group or a group —$CHR_9$— in which $R_9$ represents a substituted or unsubstituted alkyl group, a substituted or unsubstituted aryl group or a substituted or unsubstituted aralkyl group; $E_1$ and $E_2$ each independently represents a hydrogen atom or a lower alkyl group; and D represents a substituted or unsubstituted aromatic hydrocarbon group or a substituted or unsubstituted aromatic heterocyclic group.

Another object of the present invention is to provide a preparation process of the pyrroloazepine derivative (I) or its salt.

A further object of the present invention is to provide a pharmaceutical which comprises the pyrroloazepine derivative (I) or its pharmaceutically-acceptable salt as an effective ingredient and is usable for the treatment or the like of circulatory diseases.

BEST MODES FOR CARRYING OUT THE INVENTION

In the pyrroloazepine derivatives (I) of the present invention, the ring P represents any one of the following pyrrole rings:

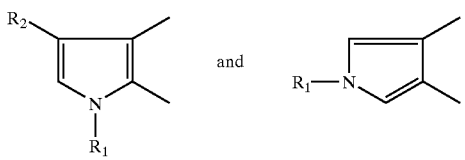

wherein $R_1$ and $R_2$ have the same meanings as defined above.

Preferred examples of the group $R_1$ bonded to the nitrogen atom of the pyrrole ring can include linear or branched alkyl groups having 1–8 carbon atoms preferably, such as methyl, ethyl, n-propyl, isopropyl and n-pentyl; cycloalkyl groups having 3–8 carbon atoms, such as cyclopropyl, cyclopentyl and cyclohexyl; cycloalkyl-alkyl groups having 4–8 carbon atoms, such as cyclopropylmethyl, cyclohexylmethyl and cyclohexylethyl; aralkyl groups having 7–22 carbon atoms, such as diphenylmethyl, benzyl and phenethyl; and aryl groups having 6–14 carbon atoms, such as phenyl and naphthyl. One or more hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and ethoxy. Particularly preferred examples of the group $R_1$ can be methyl, ethyl, benzyl and phenyl.

Preferred examples of the group $R_2$ bonded to a carbon atom of the pyrrole ring can include a hydrogen atom; and linear or branched alkyl groups having 1–8 carbon atoms preferably, such as methyl, ethyl, n-propyl, isopropyl and n-pentyl.

On the other hand, preferred examples of the group A in the compound (I) according to the present invention can include linear or branched alkylene groups having 2–10 carbon atoms, such as ethylene, trimethylene, tetramethylene, pentamethylene and octamethylene; linear or branched alkenylene groups having 4–10 carbon atoms, such as 2-butenylene and 3-pentenylene; and linear or branched alkynylene groups having 4–10 carbon atoms, such as 2-butynylene and 3-pentynylene. One or more of the hydrogen atoms of each of these groups may be substituted by a like number of halogen atoms such as fluorine, chlorine and/or bromine atoms. Among the above groups, trimethylene and tetramethylene are particularly preferred.

Further, preferred examples of the group $Z_1$ and the group $Z_2$ in the compound (I) according to the present invention can include the following combinations: when the bond indicated by the dashed line is present, $Z_1$ represents a hydrogen atom; when the bond indicated by the dashed line is absent, $Z_1$ and $Z_2$ are both hydrogen atoms, $Z_1$ represents a hydrogen atom and $Z_2$ represents the group $OR_3$, $Z_1$ and $Z_2$ both represent the groups $SR_4$, and $Z_1$ and $Z_2$ are combined together to represent an oxygen atom, the group $NOR_5$ or the group:

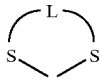

Preferred examples of $R_3$ in the group $OR_3$ can include a hydrogen atom; linear or branched alkyl groups having 1–4 carbon atoms preferably, such as methyl and ethyl; and aralkyl groups having 7–22 carbon atoms, such as benzyl and phenethyl. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Of these, hydrogen atom and methyl group are particularly preferred.

Preferred examples of $R_4$ in the group $SR_4$ can include linear or branched alkyl groups having 1–4 carbon atoms preferably, such as methyl and ethyl; aryl groups having 6–14 carbon atoms such as phenyl and naphthyl; and aralkyl groups having 7–22 carbon atoms such as benzyl and phenethyl. One or more of the hydrogen atoms of each of these groups may be substituted, for example, by a like number of halogen atoms such as fluorine, chlorine and/or bromine atoms, alkyl groups having 1–4 carbon atoms preferably, such as methyl and/or ethyl, and/or alkoxy groups having 1–4 carbon atoms, such as methoxy and/or ethoxy.

In addition, preferred examples of $R_5$ in the group $NOR_5$ can include a hydrogen atom; linear or branched alkyl groups having 1–4 carbon atoms preferably, such as methyl and ethyl; aryl groups having 6–14 carbon atoms, such as phenyl and naphthyl; and aralkyl groups having 7–22 carbon atoms, such as benzyl and phenethyl. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Of these, hydrogen atom and methyl group are particularly preferred.

Further, preferred examples of L in the group

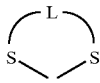

can include ethylene and trimethylene. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, aryl groups having 6–14 carbon atoms, such as phenyl and naphthyl, aralkyl groups having 7–22 carbon atoms, such as benzyl and phenethyl, and/or alkylidene groups having 1–4 carbon atoms preferably, such as methylidene and/or ethylidene.

In the compound (I) according to the present invention, Y is a group:

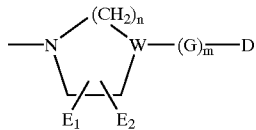

wherein D, $E_1$, $E_2$, G, W, m and n have the same meanings as defined above. The group (hereinafter called the "central heterocyclic group") represented by the following formula:

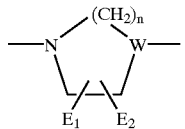

wherein $E_1$, $E_2$, W and n have the same meanings as defined above is a heterocyclic group derived from pyrrolidine, piperidine, piperazine or homopiperazine, and two or less of the hydrogen atoms on the ring may be substituted by a like number of alkyl groups having 1–4 carbon atoms preferably, such as methyl and/or ethyl.

When the central heterocyclic group is a heterocyclic group derived from pyrrolidine or piperidine, preferably a piperidine group, m stands for 0 or 1 (with the proviso that m stands for 1 when W represents C=), and G represents an oxygen atom, a sulfur atom, a carbonyl group, a sulfinyl group, a sulfonyl group, an alkylene group (an alkylene group having 1–4 carbon atoms preferably, with a methylene group being particularly preferred), an alkenylene group (an alkenylene group having 2–5 carbon atoms preferably, with a 2-propenylene group being particularly preferred), a group:

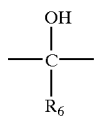

in which $R_6$ represents a substituted or unsubstituted aryl group, a group:

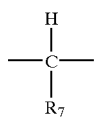

in which $R_7$ represents a hydroxyl group, an alkoxy group or an aralkyloxy group, a group:

in which the double bond is coupled with W, $R_8$ represents an alkyl group having 1–4 carbon atoms preferably, such as methyl or ethyl, an aryl group having 6–14 carbon atoms, such as phenyl or naphthyl, or an aralkyl group having 7–22 carbon atoms, such as benzyl or phenethyl, and these groups may be in substituted forms, or a cyclic or acyclic acetal group in which one or more of the hydrogen atoms may be substituted.

Here, $R_6$ represents, for example, an aryl group having 6–14 carbon atoms, such as phenyl or naphthyl. Illustrative of one or more substituents on its ring can be halogen atoms such as fluorine, chlorine and/or bromine; alkyl groups having 1–4 carbon atoms preferably, such as methyl and/or ethyl; alkoxy groups having 1–4 carbon atoms preferably, such as methoxy and/or ethoxy; and/or hydroxyl groups. Of these, preferred is a phenyl group which may be either unsubstituted or substituted by one or more fluorine atoms.

Further, $R_7$ represents a hydroxyl group; an alkoxy group having 1–4 carbon atoms, such as methoxy or ethoxy; or a substituted or unsubstituted aralkyloxy group having 7–22 carbon atoms, such as benzyloxy, 4-fluorobenzyloxy or 2-phenylethoxy.

Exemplary substituents for $R_8$ can include one or more of halogen atoms such as fluorine, chlorine and/or bromine atoms, alkyl groups having 1–4 carbon atoms preferably, such as methyl and/or ethyl, alkoxyl groups having 1–4 carbon atoms preferably, such as methoxy and/or ethoxy groups, and hydroxyl groups. Illustrative of the substituent for the cyclic or acyclic acetal can be halogen atoms such as fluorine, chlorine and bromine, alkyl groups having 1–4 carbon atoms preferably, such as methyl and ethyl, aryl groups having 6–14 carbon atoms, such as phenyl and naphthyl, aralkyl groups having 7–22 carbon atoms, such as benzyl and phenethyl, and alkylidene groups having 1–4 carbon atoms preferably, such as methylidene and ethylidene.

Exemplary cyclic or acyclic acetal groups include groups represented by the following formulas:

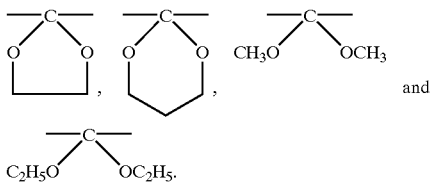

As a particularly preferred example of G when the central heterocyclic group is one derived from pyrrolidine or piperidine, a carbonyl group can be mentioned.

When the central heterocyclic group is a group derived form piperazine or homopiperazine, preferably a piperazine group, m stands for 0 or 1 (preferably 0), and G represents a carbonyl group, a sulfonyl group, an alkylene group (preferably, an alkylene group having 1–4 carbon atoms, with a methylene group being particularly preferred), an alkenylene group (preferably, an alkenylene group having 3–6 carbon atoms, with a 2-propenylene group being particularly preferred), a group —$CHR_9$— in which $R_9$ represents an alkyl group having 1–4 carbon atoms preferably, such as methyl or ethyl, an aryl group having 6–14 carbon atoms, such as phenyl or naphthyl, or an aralkyl group having 7–22 carbon atoms, such as benzyl or phenethyl).

The above-described $R_9$ may be substituted further by one or more of halogen atoms such as fluorine, chlorine and/or bromine, alkyl groups having 1–4 carbon atoms preferably, such as methyl and/or ethyl, and/or alkoxy groups having 1–4 carbon atoms preferably, such as methoxy and/or ethoxy.

As a preferred example of G when the central heterocyclic group is one derived from piperazine or homopiperazine, a substituted or unsubstituted phenylmethylene group can be mentioned.

Preferred examples of group D can include aromatic hydrocarbon groups having 6–28 carbon atoms preferably, such as a phenyl group in which one or more of the hydrogen atoms may be substituted and a naphthyl group in which one or more of the hydrogen atoms may be substituted.

Other preferred examples of D can include aromatic heterocyclic groups, preferably those each of which is monocyclic or dicyclic and contains the same or different three or less oxygen, sulfur and/or nitrogen atoms—such as pyridyl, pyrimidyl, benzisothiazolyl, benzisoxazolyl, indazolyl and indolyl groups in which one or more of hydrogen atoms may be substituted.

Examples of the substituents for the above aromatic hydrocarbon group or aromatic heterocyclic group can include halogen atoms such as fluorine, chlorine and bromine; alkyl groups having 1–4 carbon atoms preferably, such as methyl and ethyl; alkoxyl groups having 1–4 carbon atoms preferably, such as methoxy and ethoxy; aryl groups having 6–14 carbon atoms, such as phenyl and naphthyl; aralkyl groups having 7–22 carbon atoms, such as benzyl and phenethyl; aralkyloxy groups having 7–22 carbon atoms preferably, such as benzyloxy; cyano groups; nitro groups; carboxyl groups; alkoxycarbonyl groups (with an alcohol moiety thereof having 1–6 carbon atoms preferably); lower alkylsulfonylamino groups (with an alkyl moiety thereof having 1–4 carbon atoms preferably); carbamoyl groups; and hydroxyl groups.

Among these examples of group D, preferred ones can include phenyl groups which may be substituted by one or more of halogen atoms, alkoxy groups and/or hydroxyl groups; benzisothiazolyl groups which may be substituted by one or more halogen atoms; benzisoxazolyl groups which may be substituted by one or more halogen atoms; and indazolyl groups which may be substituted by one or more halogen atoms. Particularly preferred are an unsubstituted phenyl group; and phenyl groups substituted by one or more of fluorine atoms, chlorine atoms, methoxy groups and/or hydroxyl groups.

Many of the compounds (I) according to the present invention have isomers. It is to be noted that these isomers and mixtures thereof are all embraced by the present invention.

Various processes can be employed for the preparation of the pyrroloazepine derivatives (I) according to the present invention. It is however preferred to prepare them, for example, by any one or a combination of the following processes.

Process 1

Pyrroloazepine derivatives (IIa) and (IIb) useful as starting materials can be synthesized, for example, by the following process:

Process (a)

Each compound of the formula (IIa) can be obtained in accordance with the following reaction scheme, namely, by reacting a 1-substituted pyrrole-3-carboxylic acid or a derivative thereof represented by the formula (XXIa) with a β-alanine or a derivative thereof represented by the formula (XXII) or an organic or inorganic salt thereof and, if necessary, conducting deprotection to obtain a compound represented by the formula (XXIIIa) and then subjecting the thus-obtained compound to a ring-closing reaction. When the group $R_2$ of the compound (XXIa) is a hydrogen atom, the compound represented by the formula (IIb) can also be prepared together with the compound (IIa) [they will hereinafter be collectively called "the pyrroloazepine derivative (II)"].

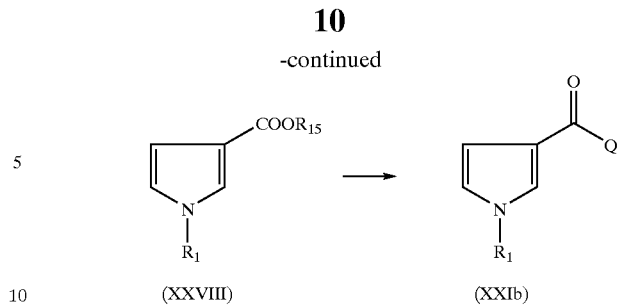

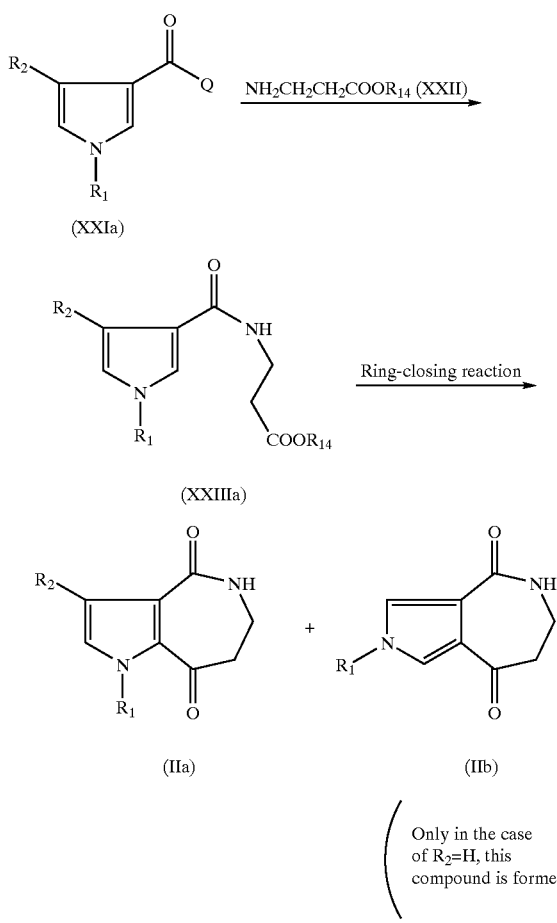

wherein $R_{14}$ represents a hydrogen atom or a carboxyl-protecting group, Q represents a hydroxyl group, an alkoxy group or an eliminative group easily replaceable by an amino group, and $R_1$ and $R_2$ have the same meanings as defined above.

The compound represented by the formula (XXIa), which is the starting material in the above-described reaction, can be synthesized by various processes. Describing one example of such processes, a compound (XXIb)—which is different from the compound (XXIa) in that $R_2$ is a hydrogen atom—can be obtained in accordance with the following reaction scheme, namely, by causing a propiolic acid ester represented by the formula (XXVII) to act on an N-substituted-N-formylglycine represented by the formula (XXVI) in the presence of an acid anhydride such as acetic anhydride or propionic anhydride to obtain a compound (XXVIII) and then converting the thus-obtained compound by a method known per se in the art.

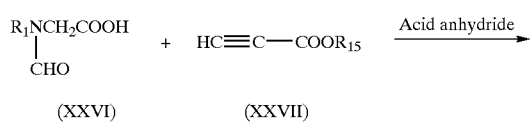

wherein $R_{15}$ represents an alkyl group, an aralkyl group or an aryl group, and $R_1$ and Q have the same meanings as defined above.

The compound (XXVI) and compound (XXVII), which are employed as starting materials in the above reaction scheme, are either known compounds or compounds available following a known process. Illustrative of the group $R_{15}$ in the compound (XXVII) can be linear or branched alkyl groups such as methyl, ethyl and isopropyl; aralkyl groups such as benzyl; and aryl groups such as phenyl. Of these, methyl and ethyl are particularly preferred. Further, examples of the acid anhydride can include acetic anhydride and propionic anhydride. Of these, acetic anhydride is particularly preferred. The reaction between the compound (XXVI) and the compound (XXVII) can be conducted by adding 1 mol or more of an acid anhydride and approximately 1 to 5 mol of the compound (XXVII) to 1 mol of the compound (XXVI), heating the resultant mixture to 80° C. to the reflux temperature and then stirring the same for 4 to 24 hours or so. This reaction can be conducted in the acid anhydride (preferably, acetic anhydride) or by adding a solvent which does not take part in the reaction, such as toluene.

Further, as another process for obtaining the 1-substituted pyrrole-3-carboxylic acid or the derivative thereof, a process can be mentioned in which in accordance with the following reaction scheme, a group $R_1''$ is introduced by a method known per se in the art into a compound (XXIX) obtained by the process disclosed in a publication [A. M. van Leusen et al, Tetrahedron Letters, 5337–5340 (1972)] to convert the compound into another compound (XXX) and then converting it further into a compound represented by the formula (XXIc) by a method known per se in the art.

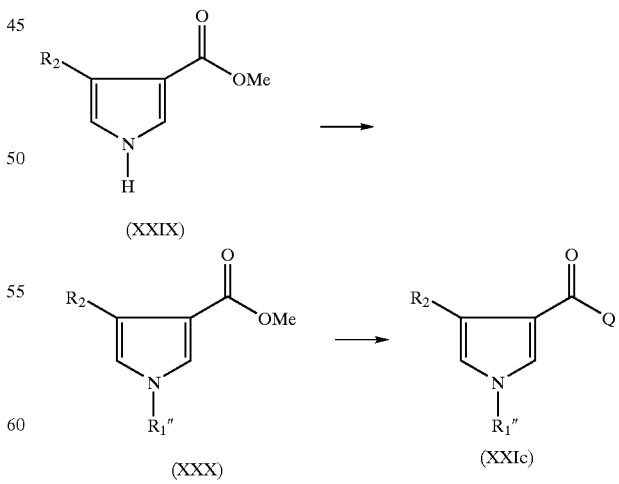

wherein $R_1''$ represents an alkyl group, a cycloalkyl group, a cycloalkyl-alkyl group or a substituted or unsubstituted aralkyl group, and $R_2$ and Q have the same meanings as defined above.

Examples of the eliminative group, which is easily replaceable with an amino group and is represented by the group Q in the compounds (XXIa), (XXIb) and (XXIc), can include halogen atoms, carboxylic acid residues and the like.

On the other hand, as the carboxyl-protecting group represented by the group $R_{14}$ in the compound (XXII), it is possible to use, in addition to lower alkyl groups such as methyl, ethyl, n-propyl, isopropyl, n-butyl, isobutyl and t-butyl and aralkyl groups having 7–20 carbon atoms, such as benzyl and 9-anthrylmethyl, conventional protecting groups such as those described in T. W. Greene: "Protective Groups in Organic Synthesis" (John Wiley & Sons, Inc.) and the like.

For the synthesis of the compound (XXIIIa), it is possible to use any one of various processes disclosed in "Compendium of Organic Synthetic Methods" (WILEY-INTERSCIENCE; A Division of John Wiley & Sons, Inc.) and the like. Illustrative processes can include a process in which a 1-substituted-pyrrole-3-carboxylic acid [the compound (XXIa) in which Q=OH] and a β-alanine or a derivative thereof represented by the compound (XXII) or an organic or inorganic salt thereof are treated with an organic compound such as diethyl phosphorocyanidate (DEPC), diphenylphosphoryl azide (DPPA), dicyclohexyl-carbodiimide (DCC), 1-ethyl-3-(3-dimethylaminopropyl) carbodiimide hydrochloride or 2-iodo-1-methylpyridinium iodide or an inorganic compound such as silicon tetrachloride or tin tetrachloride, if necessary, in the presence of an organic or inorganic base; and a process in which a 1-substituted-pyrrole-3-carboxylic acid is converted into its acid halide, symmetric acid anhydride, mixed acid anhydride, its active ester such as p-nitrophenyl ester, or the like by a method known per se in the art, and is then reacted with the compound (XXII), if necessary, in the presence of an organic or inorganic base.

Each compound (XXIIIa) thus obtained is subjected to a ring-closing reaction, optionally after removing the protecting group by virtue of a suitable method such as the action of an acid or a base, or catalytic reduction. This ring-closing reaction is conducted by treating the compound (XXIIIa) together with an organic acid such as methanesulfonic acid, trifluoromethanesulfonic acid or trifluoroacetic acid, an inorganic acid such as sulfuric acid or polyphosphoric acid or a mixture of such an organic or inorganic acid and phosphorus pentoxide at room temperature to 170° C., preferably at 80–120° C.

In this case, a solvent which does not take part in the reaction may be added as needed.

As an alternative, the ring-closing reaction can also be practiced by, optionally after addition of a catalyst, treating the compound (XXIIIa) with oxalyl chloride, thionyl chloride, thionyl bromide, oxalyl bromide, phosgene, phosphorus trichloride, phosphorus tribromide, phosphoryl chloride, phosphoryl bromide or the like to convert it into its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane. In the above-described reactions, the compound (IIa) and the compound (IIb) can be formed at varied ratios by changing the reaction conditions.

Process (b)

Among the pyrroloazepine derivatives (IIa) and (IIb), compounds (IIa") and (IIb") in each of which the group $R_1$ is other than an aryl group can be obtained in accordance with the following reaction scheme.

Namely, the compound (IIa") and the compound (IIb") can be obtained by providing a compound (XXId) as a raw material, treating it in a similar manner as in the process (a) to obtain a compound (IIa') and a compound (IIb'), and then introducing a group $R_1''$ to the pyrrole-N positions of these compounds (IIa') and (IIb')

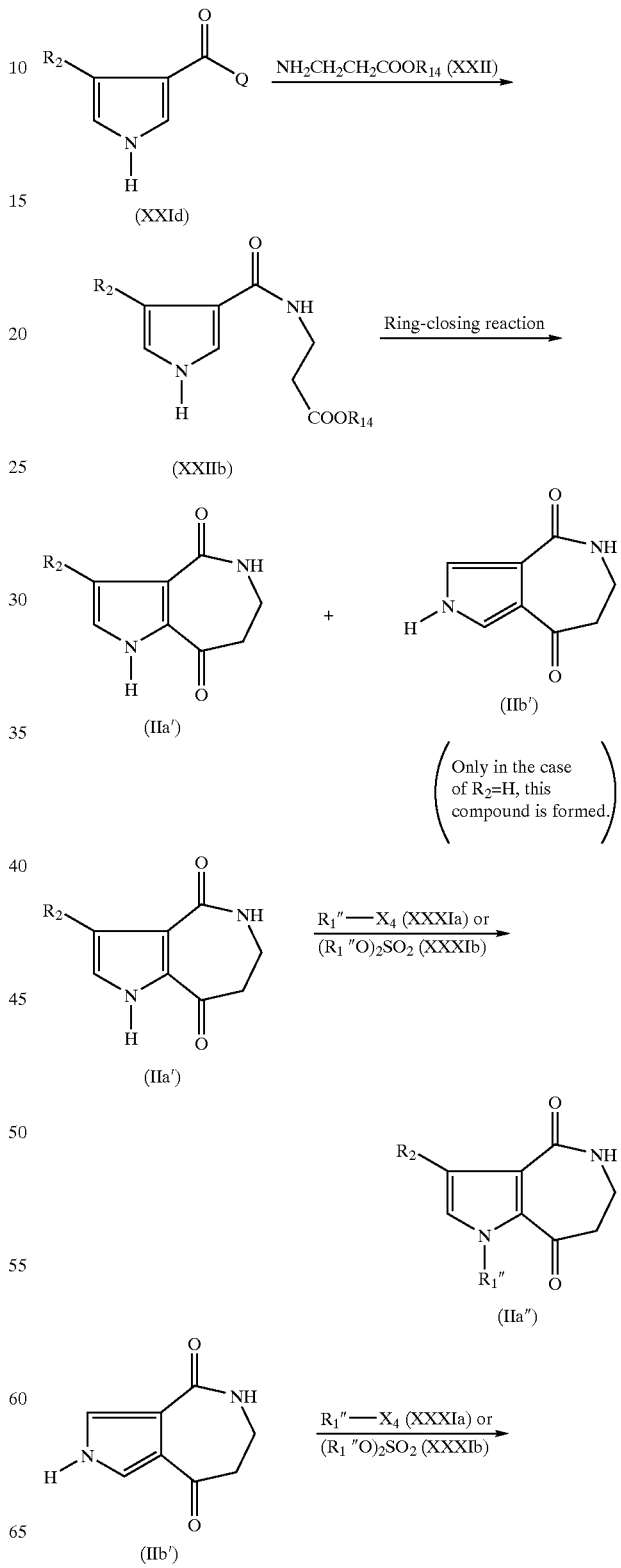

-continued

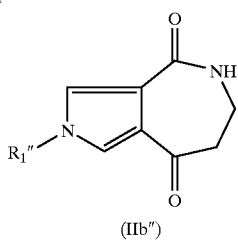

(IIb")

wherein $R_1''$, $R_2$, $R_{14}$ and Q have the same meanings as defined above, and $X_4$ represents an eliminative group.

The conversion from the compound (IIa') into the compound (IIa") can be effected by treating the compound (IIa') with an organic or inorganic base and then reacting the compound represented by the formula (XXXIa) or (XXXIb), or by causing the compound (XXXIa) or the compound (XXXIb) to act on the compound (IIa') in the presence of such a base.

Examples of the eliminative group represented by the group $X_4$ in the compound (XXXIa) can include halogen atoms such as chlorine and bromine, alkylsulfonyloxy groups such as methanesulfonyloxy, and arylsulfonyloxy groups such as p-toluenesulfonyloxy. Exemplary organic or inorganic bases can include potassium carbonate, sodium carbonate, potassium hydroxide, sodium hydroxide, sodium hydride, triethylamine, sodium methoxide, and potassium t-butoxide. Further, illustrative solvents usable in the above reaction include acetone, 2-butanone, acetonitrile, tetrahydrofuran, dioxane, dimethylformamide, and dimethylsulfoxide. The reaction is conducted at −20° C. to reflux temperature.

On the other hand, the conversion from the compound (IIb') into the compound (IIb") can also be effected under similar conditions as in the above-described conversion from the compound (IIa') into the compound (IIa").

Incidentally, the compounds obtained following the above-described process (a) and process (b)—said compounds being represented by the following formulas (XIXa) and (XIXb):

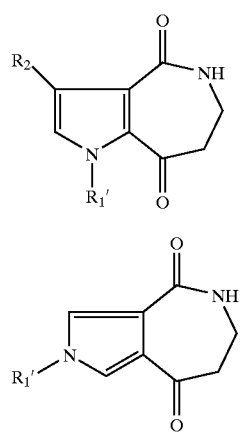

wherein $R_1'$ represents a hydrogen atom, an alkyl group, a cycloalkyl group, a cycloalkyl-alkyl group, a substituted or unsubstituted aralkyl group or a substituted or unsubstituted aryl group, and $R_2$ has the same meaning as defined above— are useful as intermediates for the production of pharmaceutical products.

Process 2

Among the pyrroloazepine derivatives (I), compounds (Ia) in each of which $Z_1$ and $Z_2$ are combined together to represent an oxygen atom can be synthesized, for example, by any one of the following processes.

Process (a)

Each compound (Ia) can be obtained in accordance with the following reaction scheme, namely, by reacting a compound represented by the formula (II) with a compound represented by the formula (III) to convert the compound (II) into a compound represented by the formula (IV) and then reacting a nitrogen-containing compound represented by the formula (V) or a salt thereof with the compound (IV):

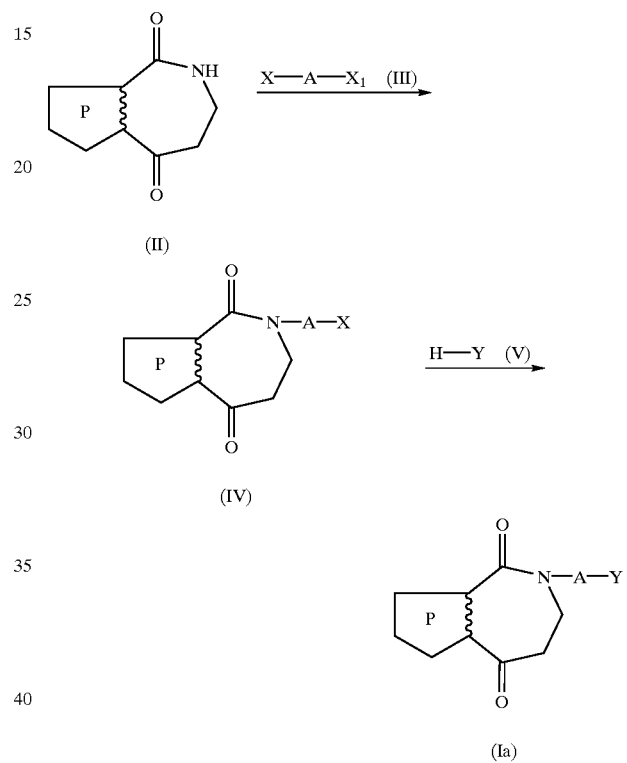

wherein X and $X_1$ represent the same or different eliminative groups, and A, the ring P and Y have the same meanings as defined above.

In the above-described reaction, the conversion from the compound (II) into the compound (IV) can be effected by treating the compound (II) with an organic or inorganic base and then reacting the compound (III), or by causing the compound (III) to act on the compound (II) in the presence of such a base.

The groups X and $X_1$ in the compound (III) are eliminative groups. Illustrative can be halogen atoms such as chlorine and bromine, alkylsulfonyloxy groups such as methanesulfonyloxy, and arylsulfonyloxy groups such as p-toluenesulfonyloxy.

Exemplary organic or inorganic bases can include sodium hydride, potassium hydroxide, sodium bis(trimethylsilyl) amide, n-butyl lithium, lithium diisopropylamide, and potassium t-butoxide.

Further, illustrative solvents usable in the above reaction can include diethyl ether, tetrahydrofuran, dioxane and toluene. The reaction can be conducted preferably at −79° C. to room temperature.

The above-described process is to synthesize each compound (IV) from its corresponding compound (II) as a raw material. Among the compounds (IV), those containing a chlorine atom or bromine atom as X can each be synthesized directly from pyrrole-3-carboxylic acid or its derivative by the following process (a') or process (a") without going through the corresponding compound (II).

Process (a')

Each compound represented by the formula (IVa') is obtained in accordance with the following reaction scheme, namely, by reacting a 1-substituted-pyrrole-3-carboxylic acid or a derivative thereof represented by the formula (XXIa) with an N-substituted-β-alanine or a derivative thereof represented by the formula (XXIV) or an organic or inorganic salt thereof and, if necessary, conducting deprotection to obtain a compound represented by the formula (XXV) and then subjecting the thus-obtained compound or an inorganic or organic salt thereof to a ring-closing reaction. When $R_2$ represents a hydrogen atom, the compound (IVb') can also be prepared together with the compound (IVa') [the compound (IVa') and the compound (IVb') may hereinafter be collectively called "(IV')"].

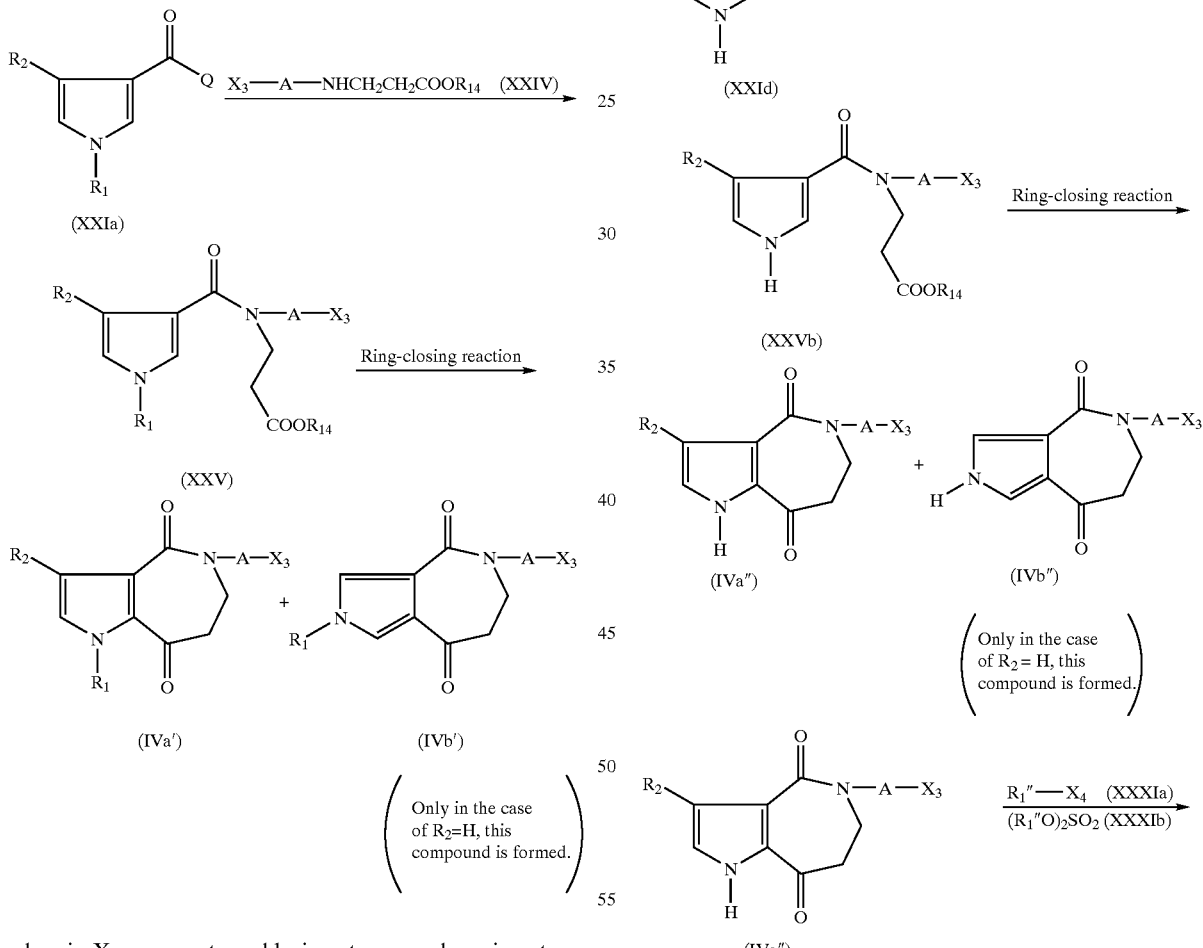

wherein $X_3$ represents a chlorine atom or a bromine atom, and A, $R_1$, $R_2$, $R_{14}$ and Q have the same meanings as defined above.

In the above-described reaction scheme, the compound represented by the formula (XXIV) can be synthesized with reference to the process disclosed in a publication [A. Fkyerat et al., "Tetrahydron", Vol. 49, pp.11237–11252 (1993)] or a conventionally-known process. Further, the conversion from the compound (XXIa) to the compound (IVa') and the compound (IVb') can be effected under similar conditions as in the conversion from the compound (XXIa) to the compound (IIa) and the compound (IIb) described above under Process (a) of Process 1.

Process (a")

Among the compounds (IV), a compound (IVa''') and a compound (IVb''') in each of which the group $R_1$ is other than an aryl group can be obtained in accordance with the following reaction scheme, namely, by introducing a group $R_1$" into the pyrrole-N positions of the corresponding compounds (IVa") and (IVb") which are available in a similar manner as in the above-described process (a') [the compound (IVa''') and the compound (IVb''') may hereinafter be collectively called "(IV''')"].

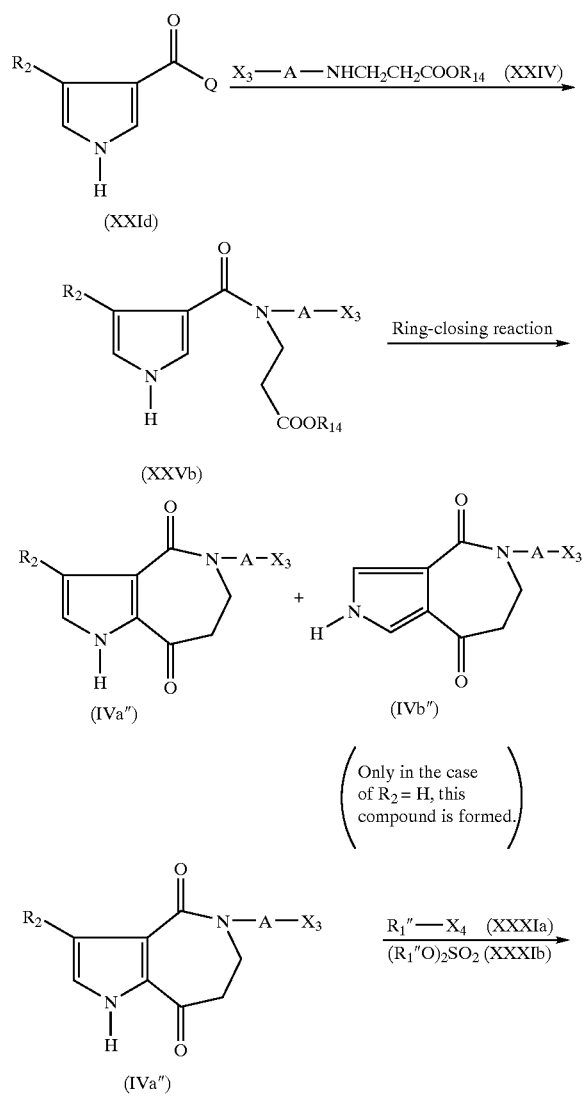

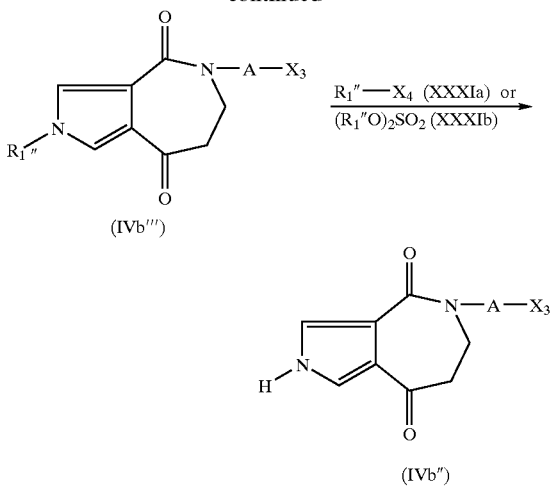

wherein A, $R_1''$, $R_2$, $R_{14}$, Q, $X_3$ and $X_4$ have the same meanings as defined above.

The conversion from the compound (XXId) into the compounds (IVa'') and the compound (IVb'') can be effected under the same conditions as in the conversion from the compound (XXIa) into the compound (IVa') and the compound (IVb') described above under Process (a') of Process 2. On the other hand, the conversion from the compound (IVa'') into the compound (IVa''') and that from the compound (IVb'') into the compound (IVb''') can be effected under similar conditions as in the conversion from the compound (IIa') into the compound (IIa'') and that from the compound (IIb') into the compound (IIb'') described above under Process (b) of Process 1.

To prepare the compound (Ia) from the thus-obtained compound (IV), compound (IV') or compound (IV''') and the nitrogen-containing compound (V), it is only necessary to react the nitrogen-containing compound (V) or an organic acid salt or inorganic acid salt thereof with the compound (IV), compound (IV') or compound (IV'''), for example, in a solvent such as methanol, ethanol, dimethylformamide, dimethylsulfoxide, acetonitrile, acetone, 2-butanone, tetrahydrofuran, dioxane or toluene at 0° C. to 150° C. In this reaction, an organic base such as triethylamine, pyridine, collidine or potassium t-butoxide or an inorganic base such as potassium carbonate, sodium carbonate, sodium hydrogencarbonate, potassium hydroxide or sodium hydride can be used as needed. Further, an alkali iodide such as potassium iodide or sodium iodide can also be added as needed.

Each of the nitrogen-containing compounds (V) is either a known compound or a compound readily available by a known process or a process similar to such a known process. Examples of the nitrogen-containing compound (V) can include 1-phenylpiperazine, 1-(2-fluorophenyl)piperazine, 1-(3-fluorophenyl)piperazine, 1-(4-fluorophenyl)piperazine, 1-(4-hydroxyphenyl)piperazine, 1-(4-nitrophenyl)piperazine, 1-(2-chlorophenyl)piperazine, 1-(3-chlorophenyl)piperazine, 1-(4-chlorophenyl)piperazine, 1-(2-methoxyphenyl)piperazine, 1-(3-methoxyphenyl)piperazine, 1-(4-methoxyphenyl)piperazine, 1-(4-methanesulfonamidophenyl)piperazine, 1-(4-cyanophenyl)piperazine, 1-(4-carbamoylphenyl)piperazine, 1-(4-methoxycarbonylphenyl)piperazine, 1-(2-pyridyl)piperazine, 1-(2-pyrimidinyl)piperazine, 1-benzylpiperazine, 1-diphenylmethylpiperazine, 1-cinnamylpiperazine, 1-benzoylpiperazine, 1-(4-benzyloxybenzoyl)piperazine, 1-(4-hydroxybenzoyl)piperazine, 1-(2-furoyl)piperazine, 1-(1,2-benzisoxazol-3-yl)piperazine, 4-phenylpiperidine, 4-benzylpiperidine, α,α-bis(4-fluorophenyl)-4-piperidinemethanol, 4-(4-fluorobenzoyl)piperidine, 4-benzoylpiperidine, 4-(4-methoxybenzoyl)piperidine, 4-(4-chlorobenzoyl)piperidine, 3-(4-fluorobenzoyl)piperidine, 4-(6-fluoro-1,2-benzisoxazol-3-yl)piperidine, 4-(6-fluoro-1,2-benzisothiazol-3-yl)piperidine, 4-(6-fluoro-1H-indazol-3-yl)piperidine, 3-benzoylpyrrolidine, 3-(4-fluorobenzoyl)pyrrolidine, 4-(4-fluorophenoxy)piperidine, 4-[(4-fluorophenyl)thio]piperidine, 4-[(4-fluorophenyl)sulfinyl]piperidine, 4-[(4-fluorophenyl)sulfonyl]-piperidine, 4-[bis(4-fluorophenyl)methylene]piperidine, and 4-(4-fluorobenzoyl)piperidine ethylene acetal.

Process (b)

Further, the compound (Ia) can also be obtained by causing a nitrogen-containing compound represented by the formula (VI) to act on the compound represented by the formula (II) in accordance with the following reaction formula:

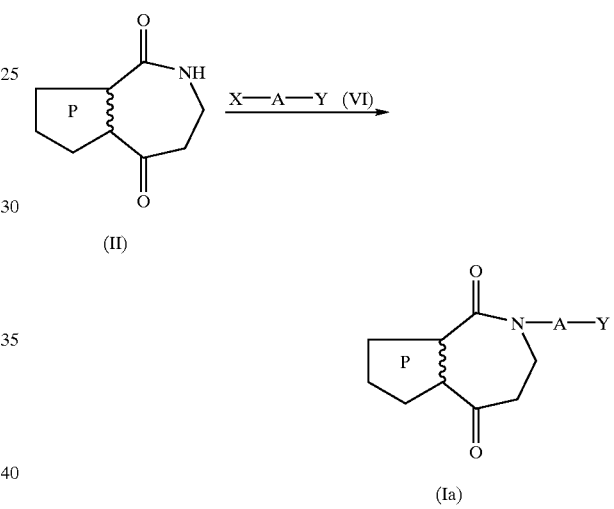

wherein A, the ring P, X and Y have the same meanings as defined above.

The conversion from the compound (II) into the compound (Ia) is conducted by causing the compound (VI) to act either after treatment of the compound (II) with an inorganic base or an organic base or in the presence of an inorganic base or an organic base. Reaction conditions are similar to those employed upon conversion from the compound (II) into the compound (IV) and described above under Process (a) of Process 2. Further, the compound (VI) can be synthesized by reacting the compound (III) with the compound (V) in a manner known per se in the art.

Process 3

Among the pyrroloazepine derivatives (I), the compounds (Ib) and (Id) in each of which $Z_1$ and $Z_2$ both represent groups $SR_4$ or $Z_1$ and $Z_2$ are combined together to represent the group:

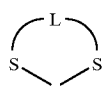

wherein L has the same meaning as defined above can be synthesized by any one of the following processes.

Process (a)

The compound (Ib) is obtained in accordance with the following reaction scheme, namely, by reacting a thiol compound, which is represented by the formula (VIIa) or (VIIb) [the compound (VIIa) and the compound (VIIb) may hereinafter be collectively called "the thiol compound (VII)"], with a compound (II) and then causing a nitrogen-containing compound (VI) to act.

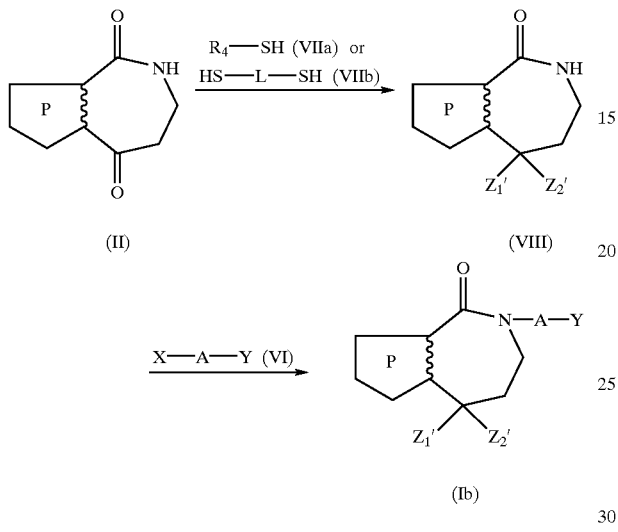

wherein $Z_1'$ and $Z_2'$ both represent groups $SR_4$ in which $R_4$ has the same meaning as defined above or are combined together to represent a group —S—L—S— in which L has the same meaning as defined above, and A, L, the ring P, $R_4$, X and Y have the same meanings as defined above.

For the conversion from the compound (II) into the compound (VIII), a suitable method can be selected from those disclosed, for example, in T. W. Greene: "Protective Groups in Organic Synthesis" (John Wiley & Sons, Inc.) and the like. Describing one example, there is a process in which the thiol compound (VII) and boron trifluoride-ether complex are caused to act on the compound (II) in chloroform. Further, the conversion from the compound (VIII) into the compound (Ib) can be effected under the same conditions as in the conversion from the compound (II) into the compound (Ia) described above under Process (b) of Process 2.

Process (b)

Each compound represented by the formula (Id) can be obtained by causing the thiol compound (VII) to act on a compound (Ic) in accordance with the following reaction scheme.

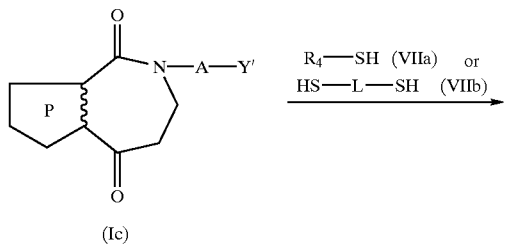

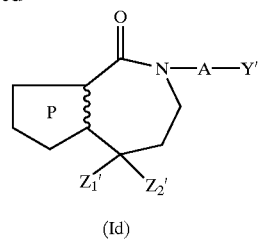

wherein
Y' represents a group:

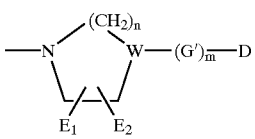

in which, when W represents CH, G' represents an oxygen atom, a sulfur atom, a sulfinyl group, a sulfonyl group, an alkylene group, an alkenylene group, a group:

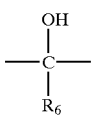

in which $R_6$ has the same meaning as defined above, a group:

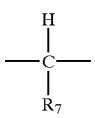

in which $R_7$ has the same meaning as defined above, or a substituted or unsubstituted cyclic or acyclic acetal group; when W represents C=, G' represents a group:

in which the double bond is coupled with W and $R_8$ represents a substituted or unsubstituted alkyl group, a substituted or unsubstituted aryl group or a substituted or unsubstituted aralkyl group; when W represents a nitrogen atom, G' represents a carbonyl group, a sulfonyl group, an alkylene group, an alkenylene group or a group —$CHR_9$— in which $R_9$ has the same meaning as defined above; D, $E_1$, $E_2$, m and n have the same meanings as defined above; and A, L, the ring P, $R_4$, $Z_1'$ and $Z_2'$ have the same meanings as defined above.

The compound (Ic) as the starting material is a compound which can be synthesized by Process 2. The conversion from the compound (Ic) into the compound (Id) can be effected under similar conditions as in the conversion of from the compound (II) into the compound (VIII) described above under Process (a) of Process 3.

Process 4

Among the pyrroloazepine derivatives (I), the compounds (Ie) and (If) in each of which $Z_1$ and $Z_2$ are combined together to represent a group $NOR_5$ can each be synthesized by any one of the following processes.

Process (a)

Each compound (Ie) is obtained in accordance with the following reaction scheme, namely, by causing hydroxylamine or a derivative thereof (IX) or a salt thereof to act on a compound represented by the formula (IV) and then causing a nitrogen-containing compound (V) to act.

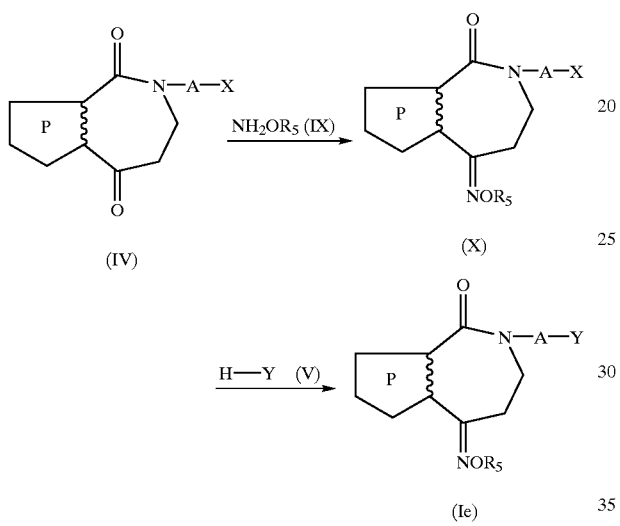

wherein A, the ring P, $R_5$, X and Y have the same meanings as defined above.

The reaction between the compound (IV) and the hydroxylamine or its derivative (IX) is effected, if necessary, in the presence of an organic base such as pyridine, triethylamine, collidine or sodium acetate or an inorganic base such as potassium carbonate or sodium hydroxide. The hydroxylamine or its derivative (IX) may also be used in the form of an organic acid salt or an inorganic acid salt.

The reaction is conducted at 0° C. to reflux temperature, preferably 0° C.–100° C. by using a suitable solvent, for example, methanol, ethanol, propanol, tetrahydrofuran, dimethylformamide or dimethylsulfoxide as needed.

Further, the conversion from the thus-obtained compound (X) into the compound (Ie) can be effected under similar conditions as in the conversion from the compound (IV) into the compound (Ia) shown above under Process (a) of Process 2.

Process (b)

Each compound (If) is obtained by causing hydroxylamine or its derivative (IX) or a salt thereof to act on a compound (Ic) in accordance with the following reaction formula:

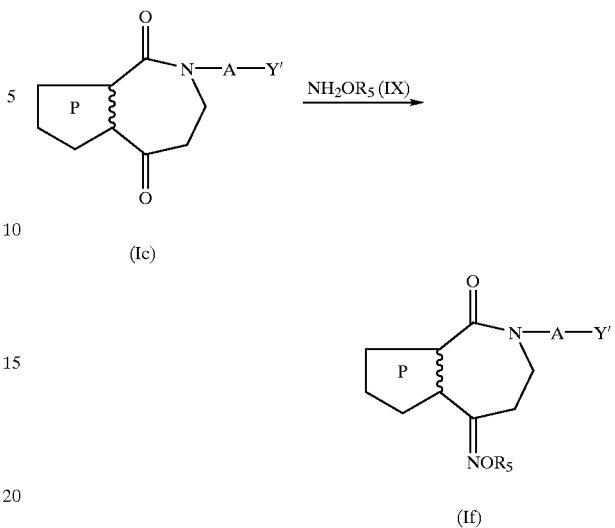

wherein A, the ring P, $R_5$ and Y' have the same meanings as defined above.

The conversion from the compound (Ic) into the compound (If) can be effected under similar conditions as the conversion from the compound (IV) into the compound (X) shown above under Process (a) of Process 4.

Process 5

Among the pyrroloazepine derivatives (I), the compounds (Ig) and (Ih) in each of which Z, represents a hydrogen atom and $Z_2$ represents a hydroxyl group can each be synthesized by any one of the following processes.

Process (a)

Each compound (Ig) is obtained in accordance with the following reaction scheme, namely, by reducing a compound represented by the formula (IV) and then causing a nitrogen-containing compound (V) to act.

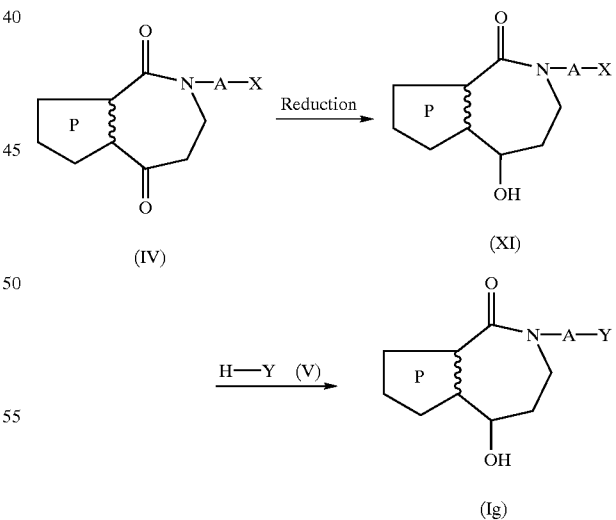

wherein A, the ring P, X and Y have the same meanings as defined above.

The conversion from the compound (IV) into the compound (XI) is conducted by treating the compound (IV) with a reducing agent such as sodium borohydride, sodium cyanoborohydride or borane at −78° C. to reflux temperature, preferably −20° C. to room temperature or by treating the compound (IV) with hydrogen gas in the presence of a catalyst.

The conversion from the compound (XI) into the compound (Ig) can be effected under similar conditions as the conversion from the compound (IV) into the compound (Ia) shown above under Process (a) of Process 2.

Process (a')

The compounds (Ig/α-OH) and (Ig/β-OH)

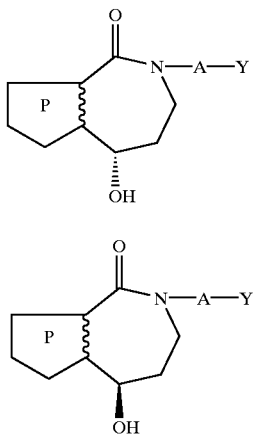

(Ig/α-OH)

(Ig/β-OH)

wherein A, the ring P and Y have the same meanings as defined above, which are optically active substances of the compound (Ig), can each be selectively synthesized by effecting asymmetric reduction in the reduction step from the compound (IV) into the compound (XI) shown above under Process (a) of Process 5.

For the asymmetric reduction, a variety of methods can be applied. As a typical example, a method making use of an oxazaborolidine-borane reducing reagent can be mentioned.

The compounds (Ig/α-OH) and (Ig/β-OH), optically active substances, can be obtained by reducing a compound, which is represented by the following formula (IV):

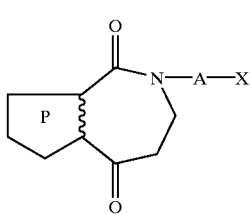

(IV)

wherein A, the ring P and X have the same meanings as defined above, with a borane reducing reagent in the presence of a chiral oxazaborolidine represented by the following formulas (XIIa) or (XIIb) [the compound (XIIa) and the compound (XIIb) will hereinafter be collectively called "the compound (XII)"]:

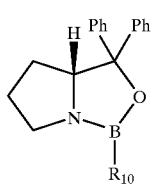

(XIIa)

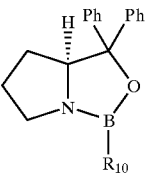

(XIIb)

wherein $R_{10}$ represents a hydrogen atom, an alkyl group or an aryl group, and then causing a compound, which is represented by the following formula (V):

H—Y  (V)

wherein Y has the same meaning as defined above, to act.

The chiral oxazaborolidine (XII) employed in the above reaction is a known catalyst, and its preparation processes are disclosed in publications [E. J. Corey et al., "J. Am. Chem. Soc.", Vol. 109, pp.7925–7926 (1987); E. J. Corey et al., "Tetrahedron Lett.", Vol. 31, pp.611–614 (1990); M. P. DeNinno et al., "Tetrahedron Lett.", Vol. 31, pp.7415–7418 (1990); S. Wallbaum et al., "Tetrahedron: Asymmetry", Vol. 3, pp.1475–1504 (1992)], Japanese Patent Application Laid-Open (Kokai) No. HEI 4-224556 and the like.

Preferred examples of $R_{10}$ in the chiral oxazaborolidine (XII) can include a hydrogen atom, a methyl group, an n-butyl group and a phenyl group. Particularly preferred is a methyl group. Specific examples of the chiral oxazaborolidine (XII) can include (R)-3,3-diphenyl-1-methyltetrahydro-1H,3H-pyrrolo[1,2-c][1,3,2]oxazaborol and (S)-3,3-diphenyl-1-methyltetrahydro-1H,3H-pyrrolo[1,2-c][1,3,2]oxazaborol.

The chiral oxazaborolidine (XII) is used in an amount sufficient to convert the reactant into a stoichiometric or less amount of the target product, preferably in 0.05 to 0.2 equivalent relative to the compound (IV).

Illustrative of the borane reducing agent which is employed as a reducing agent can include borane-dimethyl sulfide complex and borane-tetrahydrofuran complex, with borane-dimethyl sulfide complex being particularly preferred. The reducing agent is used preferably in an amount of from 1.5 to 3.0 equivalents relative to the compound (IV).

The reaction is conducted preferably in an inert gas atmosphere such as nitrogen gas or argon gas, in a solvent, for example, toluene, xylene, tetrahydrofuran, 1,2-dimethoxyethane, n-hexane or cyclohexane or a mixed solvent system thereof, preferably in toluene or tetrahydrofuran, at −20° C. to room temperature, preferably −5 to +5° C.

Incidentally, it is desired to keep the water content of the reaction system as low as possible during the reaction so that inactivation of the borane reducing agent is suppressed, deactivation of the catalyst is prevented and lowering in the optical purity is reduced. As an illustrative method for this purpose, it can be mentioned to conduct the reaction in the presence of a dehydrating agent. Preferred examples of the dehydrating agent can include molcular sieves 3A, molcular sieves 4A and molcular sieves 5A.

As another example of the asymmetric reduction method, an asymmetric reduction method of the asymmetric hydrogen transfer, said method making use of a ruthenium catalyst, can be mentioned.

Namely, the compounds (Ig/α-OH) and (Ig/β-OH) are obtained by reducing a compound, which is represented by the following formula (IV):

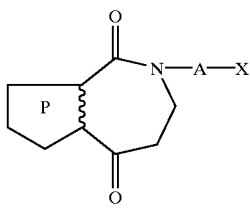
(IV)

wherein A, the ring P and X have the same meanings as defined above, in a solvent as a hydrogen source in the presence of a chiral ruthenium complex, and then reacting a nitrogen-containing compound represented by the following formula (V):

H—Y        (V)

wherein Y has the same meaning as defined above. The chiral ruthenium complex is available from a arenedichloro-ruthenium complex, which is represented by the following formula (XIII):

[RuCl$_2$($\eta^6$-arene)]$_2$        (XIII)

wherein arene represents benzene, toluene, mesitylene, p-cymene or hexamethylbenzene, and a chiral aminosulfonamide compound represented by the following formula (XIVa) or (XIVb):

(XIVa)
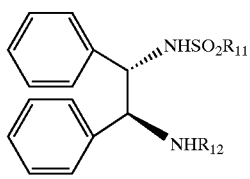

(XIVb)
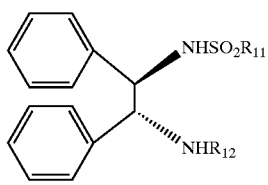

wherein R11 represents a phenyl group which may be substituted by one or more methyl groups or a naphthyl group which may be substituted by one or more methyl groups, and R$_{12}$ represents a hydrogen atom or a methyl group.

The chiral ruthenium complex, which is used in the above-described reaction and is prepared from the arenedichloro-ruthenium complex (XIII) and the chiral aminosulfonamide compound (XIVa) or (XIVb), is a known catalyst and is disclosed in publications [R. Noyori et al., "J. Am. Chem. Soc.", Vol. 117, pp.7562–7563 (1995); R. Noyori et al., "J. Am. Chem. Soc.", Vol. 118, pp.2521–2522 (1996)] and the like.

As a specific example of the arenedichloro-ruthenium complex (XIII), di-$\mu$-chlorobis[$\eta$-mesitylene]-chlororuthenium(II) can be mentioned.

On the other hand, preferred examples of the group R$_{11}$ in the chiral aminosulfonamide compound (XIVa) or (XIVb) can include phenyl, p-tolyl, 2,4,6-trimethylphenyl and 1-naphthyl, with p-tolyl being particularly preferred. Further, as a preferred example of R$_{12}$, a hydrogen atom can be mentioned. Specific examples of the chiral aminosulfonamide compound (XIVa) or (XIVb) can include (1R,2R)-N-(p-tolylsulfonyl)-1,2-diphenylethylenediamine, (1S,2S)-N-(p-tolylsulfonyl)-1,2-diphenylethylenediamine.

The chiral ruthenium complex is used in an amount sufficient to convert the reactant into a stoichiometric or less amount of the target product, preferably in 0.005 to 0.02 equivalent relative to the compound (IV).

The asymmetric reducing reaction can be conducted either in a mixed system of an azeotropic mixture of formic acid and triethylamine and, if necessary, an appropriate solvent, for example, tetrahydrofuran, acetonitrile, dichloromethane, toluene or N,N-dimethylformamide or in 2-propanol in the presence of a catalytic amount of sodium hydroxide. Preferably, it is conducted in a mixed system of a formic acid-triethylamine azeotropic mixture and tetrahydrofuran or in a mixed system of a formic acid-triethylamine azeotropic mixture and dichloromethane.

The reaction is conducted at room temperature to 60° C., preferably at room temperature.

Other illustrative methods can include an asymmetric reducing reaction of the hydrogen transfer type, which makes use of a chiral iridium complex catalyst [disclosed in A. Pfaltz et al., "Helv. Chim. Acta., Vol. 74, p.232 (1991)" or the like]; an asymmetric hydriding reaction making use of a chiral ruthenium complex catalyst [disclosed in R. Noyori et al., "Tetrahydron Lett.", Vol. 32, pp.4163–4166 (1991), R. Noyori et al., "J. Am. Chem. Soc.", Vol. 117, pp.2675–2676 (1995), R. Noyori et al., "J. Am. Chem. Soc.", Vol. 117, pp.10417–10418 (1995), or the like]; a chiral rhodium complex catalyst [disclosed in J. Bakos et al., "J. Organomet. Chem.", Vol. 197, 85 (1980) or the like]; a chiral iridium complex catalyst [H. Takaya et al., "J. Am. Chem. Soc.", Vol. 115, p.3318 (1993) or the like], or the like; asymmetric reduction making use of chiral diisopinocam-phenylchloroborane [H. C. Brown et al., "J. Am. Chem. Soc.", Vol. 110, pp.1539–1546 (1988) or the like]; and asymmetric reduction making use of chiral BINAL-H [disclosed in R. Noyori et al., "J. Am. Chem. Soc.", Vol. 101, pp.3129–3131 (1979), R. Noyori et al., "J. Am. Chem. Soc.", Vol. 106, pp.6709–6716 (1984), or the like].

Process (b)

Each compound (Ih) is obtained by reducing a compound represented by the compound (Ic) in accordance with the following reaction formula:

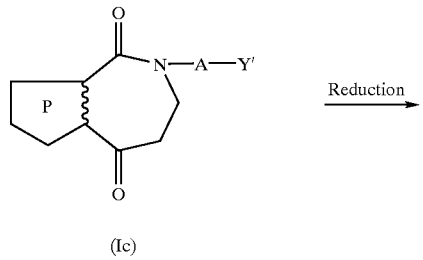
(Ic)

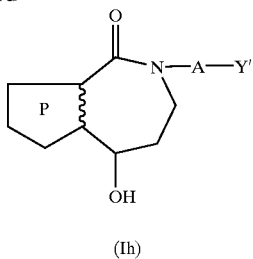

(Ih)

wherein A, the ring P and Y' have the same meanings as defined above.

The conversion from the compound (Ic) into the compound (Ih) can be effected under similar conditions as in the conversion from the compound (IV) into the compound (XI) shown above under Process (a) of Process 5.

Process (b')

The compounds (Ih/α-OH) and (Ih/β-OH)

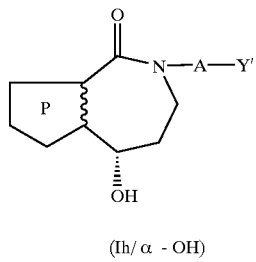 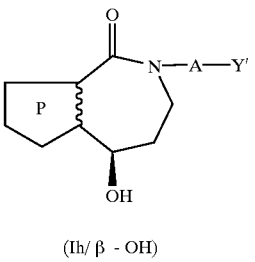

(Ih/α - OH)    (Ih/β - OH)

wherein A, the ring P and Y' have the same meanings as defined above, which are optically active substances of the compound (Ih), can each be selectively synthesized by effecting asymmetric reduction in the reduction step from the compound (Ic) into the compound (Ih) shown above under Process (b) of Process 5.

For the asymmetric reduction, a variety of methods can be applied. As a typical example, a method making use of an oxazaborolidine-borane reducing reagent can be mentioned. The reaction can be effected under similar conditions as in Process (a') of Process 5 except that the amount of the borane reducing reagent is increased to 4.0 to 7.0 equivalents relative to the compound (Ic).

As another example of the asymmetric reduction method, an asymmetric reduction method of the hydrogen transfer type, said method making use of a ruthenium catalyst, can be mentioned. The reaction can be effected under similar conditions to those shown above under Process (a') of Process 5.

Also applicable are the methods shown above under Process (a') of Process 5, namely, the asymmetric reducing reaction of the hydrogen transfer type, which makes use of the chiral iridium complex catalyst; the asymmetric hydriding reaction making use of the chiral ruthenium complex catalyst, the chiral rhodium complex catalyst, the chiral iridium complex catalyst or the like; and the asymmetric reduction making use of the chiral diisopinocamphenylchloroborane; and the asymmetric reduction making use of chiral BINAL-H.

Process 6

Among the pyrroloazepine derivatives (I), compounds (Ii) in each of which $Z_1$ represents a hydrogen atom and $Z_2$ represents the group $OR_{13}$ can be synthesized, for example, by any one of the following processes.

Process (a)

Each compound (Ii) can be obtained in accordance with the following reaction scheme, namely, by reacting a compound represented by the formula (XV) with a compound represented by the formula (XI) to obtain a compound represented by the formula (XVI) and then reacting a nitrogen-containing compound represented by the formula (V) with the compound (XVI).

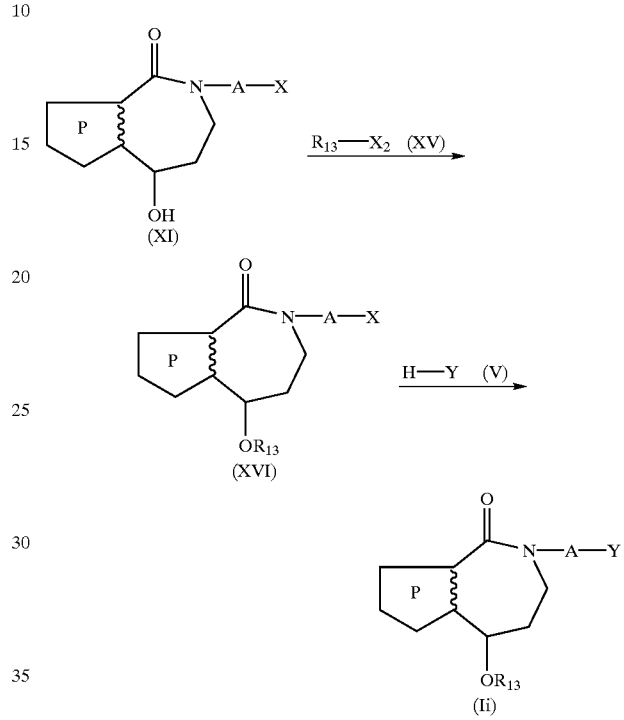

wherein $R_{13}$ represents a substituted or unsubstituted alkyl group or a substituted or unsubstituted aralkyl group, $X_2$ represents an eliminative group, and A, the ring P, X and Y have the same meanings as defined above.

In the above-described reaction, the conversion from the compound (XI) into the compound (XVI) can be conducted by causing the compound (XV) to act on the compound (XI) either after treatment of the compound (XI) with an inorganic base or an organic base or in the presence of such a base.

The group $X_2$ in the compound (XV) is an eliminative group. Illustrative can be halogen atoms such as chlorine and bromine, alkylsulfonyloxy groups such as methanesulfonyloxy, and arylsulfonyloxy groups such as p-toluenesulfonyloxy.

Exemplary organic or inorganic bases, which are usable in the above reaction, can include sodium hydride, sodium bis(trimethylsilyl)amide, lithium diisopropylamide, and potassium t-butoxide. Further, illustrative solvents usable in the above reaction can include tetrahydrofuran, dioxane, dimethylformamide, dimethylsulfoxide, N-methylpyrrolidone and toluene. The reaction may be conducted at −78° C. to reflux temperature.

The conversion from the compound (XVI) into the compound (Ii) can be effected under similar conditions as in the conversion from the compound (IV) into the compound (Ia) described above under Process (a) of Process 2.

Process (a')

The compounds (Ii/α-OR$_{13}$) and (Ii/β-OR$_{13}$)

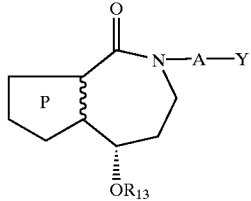

(Ii/α - OR$_{13}$)

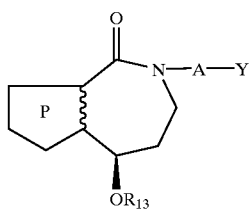

(Ii/β - OR$_{13}$)

wherein A, the ring P, R$_{13}$ and Y have the same meanings as defined above, which are optically active substances of the compound (Ii), can each be prepared by the process shown above under Process (a) of Process 6 except that compounds (XI/α-OH) and (XI/β-OH):

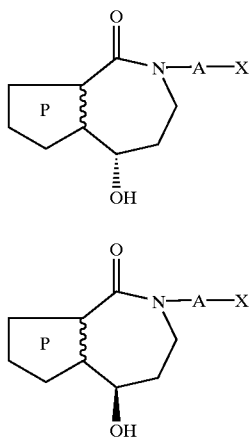

(XI/α - OH)

(XI/β - OH)

wherein A, the ring P and X have the same meanings as defined above are used as starting materials instead of the compound (XI). The compounds (XI/α-OH) and (XI/β-OH) are compounds which are obtained by subjecting the compound (IV) to asymmetric reduction in accordance with the method shown above under Process (a') of Process 5.

Process (b)

Each compound (Ii) is obtained by causing a compound (XV) to act on a compound represented by the formula (Ig) in accordance with the following reaction formula:

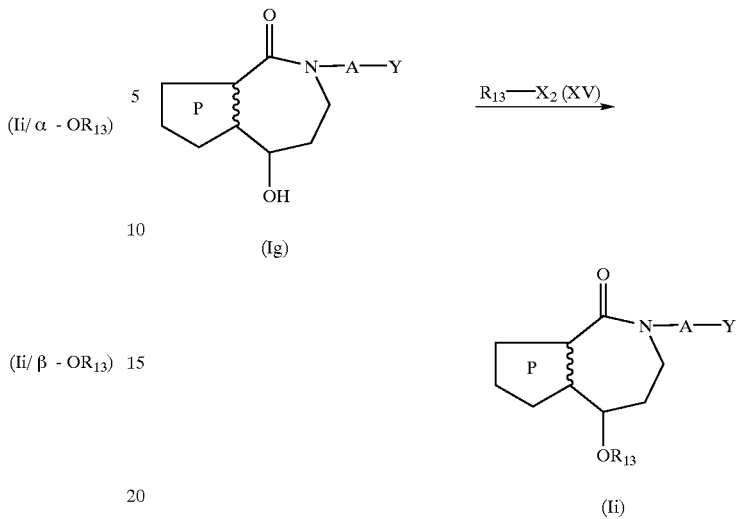

wherein A, the ring P, R$_{13}$, X$_2$ and Y have the same meanings as defined above.

In the above-described reaction, the conversion from the compound (Ig) into the compound (Ii) can be effected under similar conditions as in the conversion from the compound (XI) into the compound (XVI) described above under Process (a) of Process 6.

Process (b')

The compounds (Ii/α-OR$_{13}$) and (Ii/β-OR$_{13}$), which are optically active substances of the compound (Ii), can each be prepared by the process shown above under Process (b) of Process 6 except that compounds (Ig/α-OH) and (Ig/β-OH):

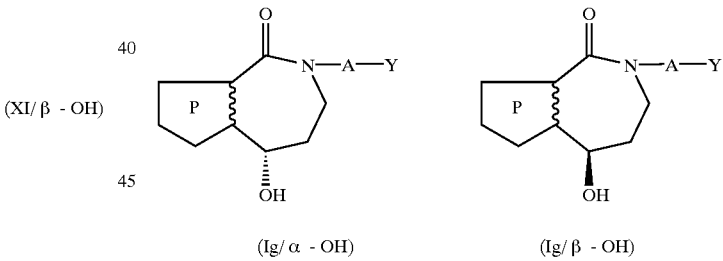

(Ig/α - OH)  (Ig/β - OH)

wherein A, the ring P and Y have the same meanings as defined above are used as starting materials instead of the compound (Ig).

Process 7

Among the pyrroloazepine derivatives (I), the compounds (Ij) in each of which the bond indicated by the dashed line is present and Z$_1$ represents a hydrogen atom can be synthesized by any one of the following processes.

Process (a)

Each compound (Ij) is obtained in accordance with the following reaction scheme, namely, by subjecting a compound represented by the formula (XI) to dehydration treatment to obtain a compound represented by the formula (XVII) and then causing a nitrogen-containing compound (V) to act on the compound (XVII).

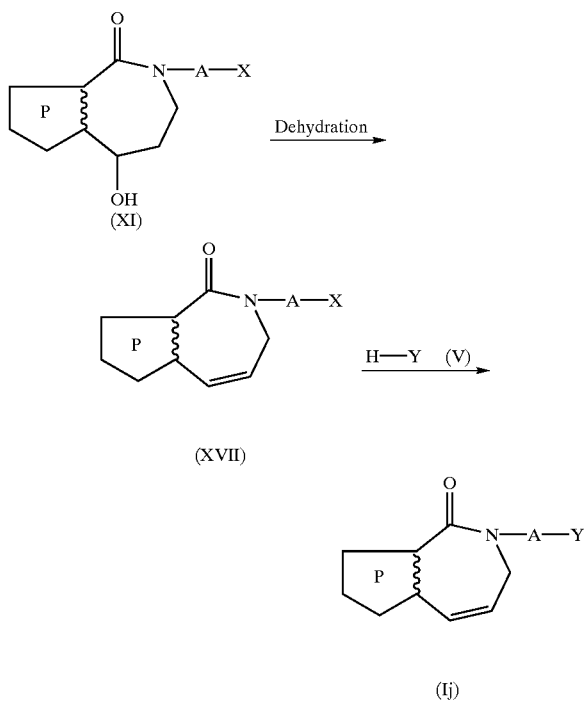

(XI)

(XVII)

(Ij)

wherein A, the ring P, X and Y have the same meanings as defined above.

In the above-described reaction, the conversion from the compound (XI) into the compound (XVII) can be achieved by adding a solvent such as water, methanol, ethanol, ethyl acetate, chloroform or toluene to the compound (XI) as needed and then treating the compound (XI) with an acid such as hydrogen chloride, hydrogen bromide, sulfuric acid, methanesulfonic acid, p-toluenesulfonic acid or the like at −20° C. to 100° C., preferably at −20° C. to room temperature.

As an alternative, the conversion from the compound (XI) into the compound (XVII) can also be effected by causing methanesulfonyl chloride, p-toluenesulfonyl chloride, phosphorus trichloride, phosphorus oxychloride, thionyl chloride or the like and a base such as triethylamine, pyridine or collidine to act on the compound (XI), if necessary, in a solvent such as dichloromethane, chloroform or toluene.

The conversion from the compound (XVII) into the compound (Ij) can be effected under similar conditions as in the conversion from the compound (IV) into the compound (Ia) described above under Process (a) of Process 2.

Process (b)

Each compound (Ij) is obtained by subjecting a compound represented by the formula (Ig) to dehydration treatment in accordance with the following reaction formula:

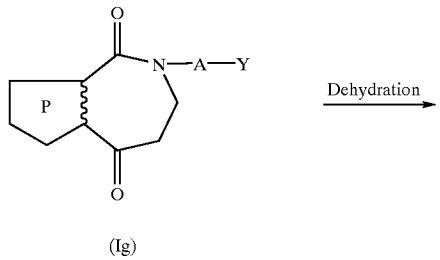

(Ig)

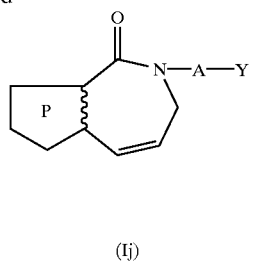

(Ij)

wherein A, the ring P and Y have the same meanings as defined above.

In the above-described reaction, the conversion from the compound (Ig) into the compound (Ij) can be effected under similar conditions as in the conversion from the compound (XI) into the compound (XVII) described above under Process (a) of Process 7.

Process 8

Among the pyrroloazepine derivatives (I), compounds (Ik) in each of which $Z_1$ and $Z_2$ both represent hydrogen atoms can be synthesized by any one of the following processes.

Process (a)

Each compound (Ik) is obtained in accordance with the following reaction scheme, namely, by reducing a compound represented by-the formula (XVII) to obtain a compound represented by the formula (XVIII) and then reacting a nitrogen-containing compound (V) with the compound (XVIII).

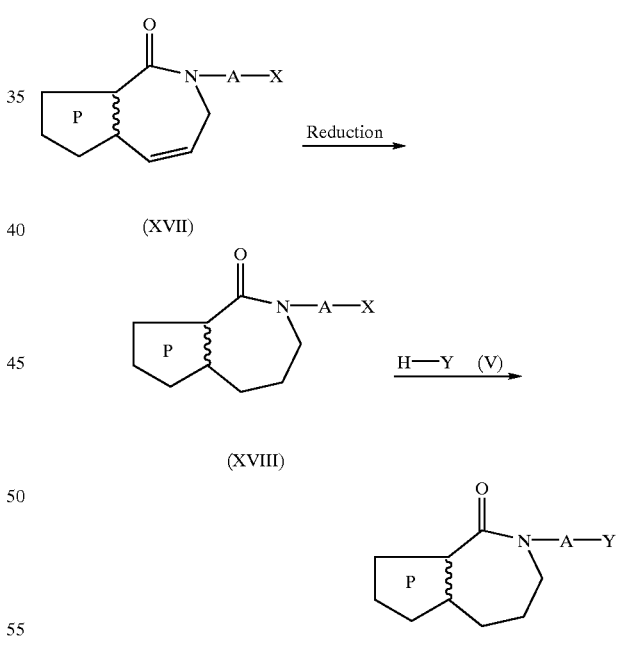

(XVII)

(XVIII)

(Ik)

wherein A, the ring P, X and Y have the same meanings as defined above.

In the above-described reaction, the conversion from the compound (XVII) into the compound (XVIII) can be conducted by treating, in the presence of a catalyst such as palladium-carbon or platinum, the compound (XVII) with hydrogen gas in an ordinarily-employed solvent at −78° C. to reflux temperature, preferably at room temperature.

The conversion from the compound (XVIII) into the compound (Ik) can be effected under similar conditions as in the conversion from the compound (IV) into the compound (Ia) described above under Process (a) of Process 2.

Process (b)

Each compound (Ik) is obtained by reducing a compound represented by the formula (Ij) in accordance with the following reaction formula:

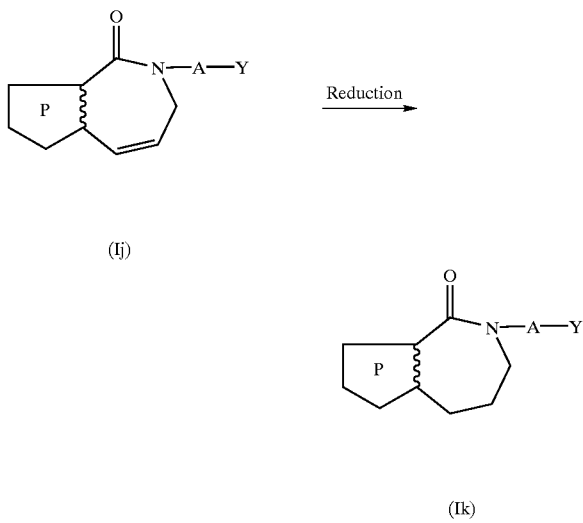

wherein A, the ring P and Y have the same meanings as defined above.

In the above-described reaction, the conversion from the compound (Ij) into the compound (Ik) can be effected under similar conditions as in the conversion from the compound (XVII) into the compound (XVIII) described above under Process (a) of Process 8.

Incidentally, among the compounds obtained in the course of the above-described processes 1 to 8, the compounds which are represented by the following formula (XX):

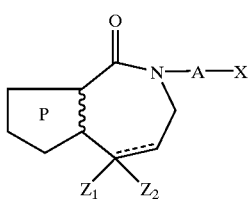

wherein the dashed line, A, the ring P, X, $Z_1$ and $Z_2$ have the same meanings as defined above are useful as intermediates for the preparation of pharmaceutical products.

If necessary, the compounds (I) of the present invention obtained according to the above-described processes can each be reacted with one of various acids to convert the compound into its salt. Then, the resulting salt can be purified by a method such as recrystallization or column chromatography.

Exemplary acids usable for the conversion of the pyrroloazepine derivatives (I) into their salts can include inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid.

Further, the compounds (I) according to the present invention include those containing asymmetric centers. Each racemic mixture can be isolated by one or more of various methods, whereby a single optically-active substance can be obtained. Usable methods include, for example:

(1) Isolation by an optically active column.
(2) Isolation by recrystallization subsequent to conversion into a salt with an optically active acid.
(3) Isolation by an enzyme reaction.
(4) Isolation by a combination of the above methods (1) to (3).

The pyrroloazepine derivatives (I) and their salts, which are obtained as described above, have strong serotonin-2 blocking action as will be demonstrated in tests to be described subsequently herein.

Moreover, the compounds (I) according to the present invention have also been found to include those also having $\alpha_1$ blocking action. From the results of pharmacological tests and toxicity tests, the compounds (I) according to the present invention have also been found to possess such merits as (1) extremely high safety, (2) long action lasting time and (3) high bioavailability. The compounds (I) according to the present invention can therefore be used as therapeutics for the treatment of circulatory diseases such as ischemic heart diseases, cerebrovascular disturbances, peripheral circulatory disturbances and hypertension.

When the pyrroloazepine derivatives (I) according to this invention are used as medicines, they can be administered in an effective dose as they are. As an alternative, they can also be formulated into various preparation forms by known methods and then administered.

Exemplary preparation forms as medicines include orally administrable preparation forms such as tablets, powders, granules, capsules and syrups as well as parenterally administrable preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth gum, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol, syrup, and the like.

When the compounds (I) according to the present invention are used as medicines, their dose varies depending on the administration purpose, the age, body weight, conditions, etc. of the patient to be administered. In oral administration, the daily dose may generally be about 0.01–1,000 mg.

The present invention will next be described in further detail by the following referential examples, examples and tests. It is however to be noted that the present invention is by no means limited to the following examples and tests.

REFERENTIAL EXAMPLE 1

Synthesis of Methyl 1-methyl-3-pyrrolecarboxylate

Subsequent to stirring of a mixture of 9.52 g (82.3 mmol) of N-formylsarcosine, 25.56 g (304 mmol) of methyl propiolate and 65 ml of acetic anhydride for 24 hours over an oil bath of 130° C., the reaction mixture was concentrated under reduced pressure.

Toluene (30 ml) was added to the residue, followed by concentration under reduced pressure. These procedures were repeated again and the resulting brown oil was distilled under reduced pressure. A 93–96° C. fraction was collected under 4 mmHg, whereby 9.01 g of the title compound were obtained (yield: 79.6%).

Appearance: Colorless to pale yellow oil.

IR (film/cm$^{-1}$): 1705, 1543, 1442, 1250, 1222, 1117, 764.

NMR (measured at 400 MHz in CDCl$_3$ with TMS as an internal standard, δ ppm): 3.65(3H,s), 3.78(3H,s), 6.51–6.58 (2H,m), 7.22(1H,m).

REFERENTIAL EXAMPLE 2
Synthesis of Ethyl 1-ethyl-3-pyrrolecarboxylate

Using 117.1 g (1 mol) of N-formylsarcosine, 98.1 g (1 mol) of ethyl propiolate and 638 ml of acetic anhydride, a reaction and post treatment were conducted in a similar manner as in Referential Example 1. The resulting brown oil was distilled under reduced pressure and a 103–104° C. fraction was collected under 4 mmHg, whereby 109.19 g of the title compound were obtained (yield: 71.3%).

Appearance: Colorless to pale yellow oil.

IR (film/cm$^{-1}$): 1701, 1544, 1250, 1218, 1113, 1026, 965, 763.

NMR (measured at 400 MHz in CDCl$_3$ with TMS as an internal standard, δ ppm): 1.32(3H,t,J=7.1 Hz), 3.66(3H,s), 4.26(2H,q,J=7.1 Hz), 6.54(1H,m), 6.57(1H,m), 7.23(1H,t,J=1.9 Hz).

REFERENTIAL EXAMPLE 3
Synthesis of Ethyl 1-benzyl-3-pyrrolecarboxylate

Using 1.93 g (10 mmol) of N-benzyl-N-formylglycine, 3.65 g (37.2 mmol) of ethyl propiolate and 10 ml of acetic anhydride, a reaction and post treatment were conducted in a similar manner as in Referential Example 1. The resulting brown oil was purified by silica gel column chromatography [silica gel: "No.9385", product of Merck & Co., Inc. (the same silica gel was also used in the subsequent referential examples and examples); eluent: ethyl acetate/hexane=1/3], whereby 2.156 g of the title compound were obtained (yield: 94.0%).

Appearance: Pale yellow oil.

IR (film/cm$^{-1}$): 2980, 1702, 1541, 1508, 1455, 1373, 1221, 1112, 1027, 968, 763, 711.

NMR (measured in CDCl$_3$ with TMS as an internal standard/400 MHz/δ ppm): 1.33(3H,t,J=7.1 Hz), 4.26(2H, q,J=7.1 Hz), 5.06(2H,s), 6.59–6.64(2H,m), 7.27–7.39(4H, m).

REFERENTIAL EXAMPLE 4
Synthesis of Ethyl 1-phenyl-3-pyrrolecarboxylate

From 2.69 g (15 mmol) of N-formyl-N-phenylglycine, 5.47 g (55.8 mmol) of ethyl propiolate and 15 ml of acetic anhydride, 2.894 g of the title compound were obtained in a similar manner as in Referential Example 3 (yield: 89.6%).

Appearance: Pale yellow oil.

IR (film/cm$^{-1}$): 1709, 1600, 1544, 1509, 1260, 1224, 1138, 757, 692.

NMR (measured at 400 MHz in CDCl$_3$ with TMS as an internal standard, δ ppm): 1.36(3H,t,J=7.1 Hz), 4.31(2H,q, J=7.1 Hz), 6.76(1H,br.s), 7.01(1H,br.s), 7.31(1H,t,J=7.2 Hz), 7.34–7.50(4H,m), 7.68(1H,s).

REFERENTIAL EXAMPLE 5
Synthesis of 1-methyl-3-pyrrolecarboxylic Acid

A mixture of 7.66 g (50 mmol) of the ethyl 1-methyl-3-pyrrolecarboxylate obtained in Reference Example 2 and 37.5 ml (75 mmol) of a 2 N aqueous solution of sodium hydroxide was refluxed for 2 hours. The reaction mixture was cooled down to 0° C., at which 6 N hydrochloric acid was added under stirring to acidify the reaction mixture. Sodium chloride (15 g) was then added, followed by stirring for 1 hour over an ice-acetone bath. Precipitated crystals were collected. After the crystals were washed with chilled water, the crystals were dried under reduced pressure, whereby 5.77 g of the title compound were obtained (yield: 92.2%).

Appearance: Colorless needle crystals.

Melting point: 144.0–146.5° C. (recrystallized from ethyl acetate-isopropyl ether).

IR (KBr/cm$^{-1}$): 3300–2200, 1671, 1534, 1450, 1347, 1260, 1221, 1128, 1066, 767, 712.

NMR (measured at 400 MHz in CDCl$_3$ with TMS as an internal standard, δ ppm): 3.68(3H,s), 6.56(1H,m), 6.62(1H, m), 7.31(1H,m).

REFERENTIAL EXAMPLE 6
Synthesis of 1-phenyl-3-pyrrolecarboxylic Acid

A mixture of 15.50 g (72 mmol) of ethyl 1-phenyl-3-pyrrolecarboxylate obtained following the procedures of Reference Example 4 and 54 ml (108 mmol) of a 2 N aqueous solution of sodium hydroxide was refluxed for 3 hours. The reaction mixture was cooled down to 0° C., at which 2 N hydrochloric acid was added under stirring to acidify the reaction mixture, followed by the extraction (twice) with chloroform.

Chloroform layers were washed with a saturated aqueous solution of sodium chloride. The chloroform solution was dried over anhydrous sodium sulfate and was then concentrated under reduced pressure. The resultant crude crystals were recrystallized from ethyl acetate-hexane, whereby 11.51 g of the title compound were obtained (yield: 85.4%).

Appearance: Colorless flake crystals.

Melting point: 119.0–121.0° C.

IR (KBr/cm$^{-1}$): 2590, 1676, 1599, 1552, 1511, 1446, 1285, 1232, 1168, 1091, 1044, 969, 820, 754, 684.

NMR (measured at 400 MHz in CDCl$_3$ with TMS as an internal standard, δ ppm): 6.82(1H,dd,J=1.7 Hz,2.9 Hz), 7.05(1H,t,J=2.7 Hz), 7.34(1H,m), 7.40–7.50(4H,m), 7.78 (1H,t,J=1.9 Hz)

EXAMPLE 1
Synthesis of Benzyl 3-(1-methyl-3-pyrrolecarboxamido) propionate (Compound No. 1)

Into a solution of 5.01 g (40 mmol) of 1-methyl-3-pyrrolecarboxylic acid and 16.87 g (48 mmol) of β-alanine benzyl ester p-toluenesulfonate in 200 ml of dimethylformamide (hereinafter called "DMF"), a solution of 7.83 g (48 mmol) of diethyl phosphorocyanidate in 50 ml of DMF was added dropwise under ice cooling and stirring. A solution of 9.71 g (96 mmol) of triethylamine in 50 ml of DMF was then added dropwise, and the reaction mixture was stirred at room temperature for 67 hours.

The reaction mixture was concentrated under reduced pressure, followed by the addition of ethyl acetate-benzene (3:1 V/V) to the residue. The resultant solution was washed with a half-saturated aqueous solution of potassium carbonate, water, a 10% aqueous solution of citric acid, water and a saturated aqueous solution of sodium chloride. The solution was dried over anhydrous sodium sulfate and was then concentrated under reduced pressure. The residue was washed with hexane and was then recrystallized from ethyl acetate-hexane, whereby 9.44 g of the title compound were obtained (yield: 82%).

EXAMPLE 2
Synthesis of Ethyl 3-(1-ethyl-3-pyrrolecarboxamido) propionate (Compound No. 2)

Into a suspension of 3.33 g (23.9 mmol) of 1-ethyl-3-pyrrolecarboxylic acid, 4.41 g (28.7 mmol) of β-alanine ethyl ester hydrochloride and 5.50 g (28.7 mmol) of 1-ethyl-3-(3-dimethylaminopropyl)carbodiimide hydrochloride in 40 ml of methylene chloride, 4.0 ml (28.7 mmol) of triethylamine were added dropwise under ice cooling and stirring. The reaction mixture was stirred at room temperature for 2.5 hours.

The reaction mixture was washed with 1 N hydrochloric acid, a saturated aqueous solution of sodium hydrogencarbonate, water and a saturated aqueous solution of sodium chloride, dried over anhydrous magnesium sulfate, and then concentrated under reduced pressure. The residue was purified by chromatography on a silica gel column (eluent: 2%-methanol/methylene chloride→10%-methanol/methylene chloride), whereby 2.19 g of the title compound were obtained (yield: 38%).

EXAMPLE 3
Synthesis of Benzyl 3-(3-pyrrolecarboxamido)propionate (Compound No. 3)

Using 1.67 g (15 mmol) of 3-pyrrolecarboxylic acid, 6.33 g (18 mmol) of β-alanine benzyl ester p-toluenesulfonate, 2.94 g (18 mmol) of diethyl phosphorocyanidate, 3.64 g (36 mmol) of triethylamine and 50 ml of DMF, 3.62 g of the title compound were obtained in a similar manner as in Example 1 (yield: 89%).

EXAMPLE 4
Synthesis of Ethyl 3-(4-methyl-3-pyrrolecarboxamido) propionate (Compound No. 4)

Using 7.63 g (60 mmol) of 4-methyl-3-pyrrolecarboxylic acid, 15.4 g (100 mmol) of β-alanine ethyl ester hydrochloride, 14 ml (100 mmol) of triethylamine, 17.3 g (90 mmol) of 1-ethyl-3-(3-dimethylaminopropyl) carbodiimide hydrochloride and 100 ml of methylene chloride, 5.80 g of the title compound were obtained in a similar manner as in Example 2 (yield: 26%).

EXAMPLE 5
Synthesis of 3-(1-methyl-3-pyrrolecarboxamido)propionic Acid (Compound No. 5)

To a solution of 7.16 g (25 mmol) of Compound No. 1 in 300 ml of tetrahydrofuran (hereinafter abbreviated as "THF"), 716 mg of 5%-palladium/carbon were added, followed by stirring for 72 hours under a hydrogen gas stream. The reaction mixture was filtered, and the catalyst was washed with methanol. The filtrate and the washing were combined, followed by concentration under reduced pressure. The residue was recrystallized from acetonitrile, whereby 4.14 g of the title compound were obtained (yield: 84%).

EXAMPLE 6
Synthesis of 3-(1-ethyl-3-pyrrolecarboxamido)propionic Acid (Compound No. 6)

To a solution of 2.19 g (9.2 mmol) of Compound No. 2 in 30 ml of ethanol, 5 ml (10 mmol) of a 2 N aqueous solution of sodium hydroxide were added. The reaction mixture was stirred at room temperature for 1.5 hours. The reaction mixture was then concentrated under reduced pressure, 20 ml (20 mmol) of 1 N hydrochloric acid were added to the residue, and the resultant mixture was extracted with methylene chloride (three times). The organic layers were washed with a saturated aqueous solution of sodium chloride, dried over anhydrous magnesium sulfate, and then concentrated under reduced pressure. The residue was recrystallized from acetonitrile, whereby 1.37 g of the title compound were obtained (yield: 71%).

EXAMPLE 7
Synthesis of 3-(3-pyrrolecarboxamido)propionic Acid (Compound No. 7)

Using 8.29 g (30.4 mmol) of Compound No. 3, 829 mg of 5%-palladium/carbon, hydrogen gas and 200 ml of THF, 3.89 g of the title compound were obtained in a similar manner as in Example 5 (yield: 70%).

EXAMPLE 8
Synthesis of 3-(4-methyl-3-pyrrolecarboxamido)propionic Acid (Compound No. 8)

Using 5.83 g (26 mmol) of Compound No. 4, 13 ml (26 mmol) of a 2 N aqueous solution of sodium hydroxide and 50 ml of ethanol, 4.35 g of the title compound were obtained in a similar manner as in Example 6 (yield: 85%).

EXAMPLE 9
Synthesis of 1-methyl-1,4,5,6,7,8-hexahydropyrrolo[3,2-c]azepine-4,8-dione (Compound No. 9) and 2-methyl-2,4,5,6,7,8-hexahydropyrrolo[3,4-c]azepine-4,8-dione (Compound No. 10)

A mixture of 348 mg (1.5 mmol) of Compound No. 5 and 17.5 g of polyphosphoric acid (80%) was stirred at 100° C. for 1 hour. Water (150 ml) was added to the reaction mixture. Potassium carbonate was then added to the resultant mixture to adjust its pH to 5. The thus-obtained mixture was suturated with sodium chloride, followed by extraction with THF (three times). The organic layers were washed with a saturated aqueous solution of sodium chloride, dried over anhydrous sodium sulfate, and then concentrated under reduced pressure. The residue was separated and purified by chromatography on a silica gel column (eluent: 3%-methanol/chloroform), whereby 161 mg of Compound No. 9 and 52 mg of Compound No. 10 were obtained (yields: 50% and 16%, respectively).

EXAMPLE 10
Synthesis of 1-ethyl-1,4,5,6,7,8-hexahydropyrrolo[3,2-c]azepine-4,8-dione (Compound No. 11)

Using 1.35 g (6.42 mmol) of Compound No. 6 and 65 g of polyphosphoric acid (80%), 615 mg of the title compound were obtained in a similar manner as in Example 9 (yield: 50%).

EXAMPLE 11
Synthesis of 1,4,5,6,7,8-hexahydropyrrolo[3,2-c]azepine-4,8-dione (Compound No. 12) and 2,4,5,6,7,8-hexahydropyrrolo[3,4-c]azepine-4,8-dione (Compound No. 13)

Using 2.0 g (11 mmol) of Compound No. 7 and 210 g of polyphosphoric acid (80%), 670 mg of Compound No. 12 and 119 mg of Compound No. 13 were obtained in a similar manner as in Example 9 (yields: 37% and 7%, respectively).

EXAMPLE 12
Synthesis of 3-methyl-1,4,5,6,7,8-hexahydropyrrolo[3,2-c]azepine-4,8-dione (Compound No. 14)

Using 4.15 g (21 mmol) of Compound No. 8 and 208 g of polyphosphoric acid (80%), 2.12 g of the title compound were obtained in a similar manner as in Example 9 (yield: 57%).

EXAMPLE 13
Synthesis of 1,3-dimethyl-1,4,5,6,7,8-hexahydropyrrolo[3,2-c]azepine-4,8-dione (Compound No. 15)

Into a suspension of 1.62 g (14.4 mmol) of potassium t-butoxide and 317 mg (1.2 mmol) of 18-crown-6 in 20 ml of THF, a suspension of 2.12 g (12 mmol) of Compound No.

14 in 20 ml of THF and a solution of 2.55 g (18 mmol) of methyl iodide in 5 ml of THF were successively added dropwise under ice cooling and stirring. The reaction mixture was stirred at room temperature. Twenty-four hours later, a solution of 0.81 g (7.2 mmol) of potassium t-butoxide and 1.28 g (9.0 mmol) of methyl iodide in 5 ml of DMF was added and further 24 hours later, a solution of 0.81 g (7.2 mmol) of potassium t-butoxide and 1.28 g (9.0 mmol) of methyl iodide in 5 ml of DMF was added. The reaction mixture was stirred at room temperature for further 3 hours.

The reaction mixture was concentrated under reduced pressure. A saturated aqueous solution of sodium chloride was added to the residue, followed by extraction with ethyl acetate (3 times). Organic layers were dried over anhydrous sodium sulfate and were then concentrated under reduced pressure. The residue was purified by chromatography on a silica gel column (eluent: 15%-acetone/methylene chloride) and was then recrystallized from ethyl acetate-hexane, whereby 0.98 g of the title compound was obtained (yield: 43%).

EXAMPLE 14
Synthesis of 1-benzyl-1,4,5,6,7,8-hexahydropyrrolo[3,2-c]azepine-4,8-dione (Compound No. 16)

A suspension of 1.64 g (10 mmol) of Compound No. 12, 3.42 g (20 mmol) of benzyl bromide and 2.76 g (20 mmol) of potassium carbonate in 100 ml of 2-butanone was refluxed for 22 hours. The reaction mixture was filtered, and the filtrate was concentrated under reduced pressure. Chloroform was added to the residue. The organic layer was washed with water and a saturated aqueous solution of sodium chloride, dried over anhydrous sodium sulfate, and then concentrated under reduced pressure.

The residue was purified by chromatography on a silica gel column (eluent: 1%-methanol/chloroform→2%-methanol/chloroform), whereby 2.36 g of the title compound were obtained (yield: 93%).

EXAMPLE 15
Synthesis of 5-(3-chloropropyl)-1-methyl-1,4,5,6,7,8-hexahydropyrrolo[3,2-c]azepine-4,8-dione (Compound No. 17)

Into a solution of 1.68 g (15 mmol) of potassium t-butoxide in 40 ml of THF, 1.34 g (7.5 mmol) of Compound No. 9 were added under ice cooling and stirring. After the reaction mixture was stirred at 0° C. for 1 hour, a solution of 5.90 g (37.5 mmol) of 1-bromo-3-chloropropane in 40 ml of THF was added dropwise at the same temperature, followed by stirring at room temperature for 93 hours.

An aqueous solution of 1.58 g of citric acid monohydrate was added to the reaction mixture, and the resultant mixture was concentrated under reduced pressure. Water was added to the residue, followed by extraction with chloroform (twice). The organic layers were washed with a saturated aqueous solution of sodium chloride, dried over anhydrous sodium sulfate, and then concentrated under reduced pressure. The residue was purified by chromatography on a silica gel column (eluent: ethyl acetate/hexane=2/1), whereby 628 mg of the title compound were obtained (yield: 33%).

EXAMPLE 16
Synthesis of 5-(4-chlorobutyl)-1-methyl-1,4,5,6,7,8-hexahydropyrrolo[3,2-c]azepine-4,8-dione (Compound No. 18)

Using 1.78 g (10 mmol) of Compound No. 9, 2.24 g (20 mmol) of potassium t-butoxide, 8.57 g (50 mmol) of 1-bromo-4-chlorobutane and 100 ml of THF, 1.32 g of the title compound were obtained in a similar manner as in Example 15 (yield: 49%).

EXAMPLE 17
Synthesis of 5-(3-chloropropyl)-2-methyl-2,4,5,6,7,8-hexahydropyrrolo[3,4-c]azepine-4,8-dione (Compound No. 19)

Into a suspension of 264 mg (6.6 mmol) of 60% sodium hydride in 30 ml of DMF, a solution of 1.07 g (6 mmol) of Compound No. 10 in 20 ml of DMF was added under ice cooling and stirring. After the reaction mixture was stirred at 0° C. for 1 hour and then at room temperature for 1 hour, a solution of 4.72 g (30 mmol) of 1-bromo-3-chloropropane in 5 ml of DMF was added dropwise at 0° C. The reaction mixture was stirred at 0° C. for 1 hour and then at room temperature for 17 hours.

To the reaction mixture, 3 ml of 1 N hydrochloric acid were added, followed by concentration under reduced pressure. Water was added to the residue, followed by extraction with chloroform (three times). The organic layers were washed with a saturated aqueous solution of sodium chloride, dried over anhydrous sodium sulfate, and then concentrated under reduced pressure. The residue was purified by chromatography on a silica gel column (eluent: ethyl acetate→8%-methanol/chloroform), whereby 429 mg of the title compound were obtained (yield: 28%).

EXAMPLE 18
Synthesis of 5-(3-chloropropyl)-1-ethyl-1,4,5,6,7,8-hexahydropyrrolo[3,2-c]azepine-4,8-dione (Compound No. 20)

Using 610 mg (3.2 mmol) of Compound No. 11, 718 mg (6.4 mmol) of potassium t-butoxide, 2.52 g (16 mmol) of 1-bromo-3-chloropropane and 20 ml of THF, 245 mg of the title compound were obtained in a similar manner as in Example 15 (yield: 28%).

EXAMPLE 19
Synthesis of 5-(3-chloropropyl)-1,3-dimethyl-1,4,5,6,7,8-hexahydropyrrolo[3,2-c]azepine-4,8-dione (Compound No. 21)

Using 0.96 g (5 mmol) of Compound No. 15, 1.12 g (10 mmol) of potassium t-butoxide, 3.46 g (22 mmol) of 1-bromo-3-chloropropane and 50 ml of THF, 676 mg of the title compound were obtained in a similar manner as in Example 15 (yield: 50%).

EXAMPLE 20
Synthesis of 1-benzyl-5-(3-chloropropyl)-1,4,5,6,7,8-hexahydropyrrolo[3,2-c]azepine-4,8-dione (Compound No. 22)

Using 2.03 g (8 mmol) of Compound No. 16, 1.80 g (16 mmol) of potassium t-butoxide, 6.30 g (40 mmol) of 1-bromo-3-chloropropane and 40 ml of THF, 585 mg of the title compound were obtained in a similar manner as in Example 15 (yield: 22%).

EXAMPLE 21
Synthesis of Ethyl 3-[1-methyl-3-[N-(3-chloropropyl)]pyrrolecarboxamido]propionate (Compound No. 23)

A suspension of 50.05 g (400 mmol) of 1-methyl-3-pyrrolecarboxylic acid in 180 ml of THF was cooled to −5° C., into which a solution of 50.77 g (400 mmol) of oxalyl chloride in 20 ml of THF was added dropwise under stirring over about 5 minutes, followed by the addition of 200 μl of DMF. After the reaction mixture was stirred at room temperature for 1.5 hours, 200 ml of THF and 101.3 g (440 mmol) of ethyl 3-(3-chloropropyl)aminopropionate hydrochloride were added successively. The reaction mixture was cooled to −5° C., to which a solution of 161.9 g (1.60 mol) of triethylamine in 200 ml of THF was added under stirring at such a rate that the internal temperature did not exceed 10° C. The resultant mixture was stirred under cooling for 10 minutes and then at room temperature for 1.5 hours.

Ethyl acetate was added to the reaction mixture. The organic layer was washed successively with a 1/3 saturated aqueous solution of sodium chloride, 2 N hydrochloric acid, a 1/3 saturated aqueous solution of sodium chloride, a saturated aqueous solution of sodium hydrogencarbonate-a saturated aqueous solution of sodium chloride (2:1 V/V), and a saturated aqueous solution of sodium chloride. Then, the organic layer was dried over anhydrous sodium sulfate and concentrated under reduced pressure, whereby 120.22 g of a crude product were obtained.

Although the product was substantially pure, a portion of the crude product was purified by chromatography on a silica gel column (eluent: 2%-methanol/chloroform). Physical data of the purified product were then measured, so that the product was confirmed to be the title compound.

EXAMPLE 22

Synthesis of Ethyl 3-[1-phenyl-3-[N-(3-chloropropyl)]pyrrolecarboxamido]propionate (Compound No. 24)

Into a solution of 3.74 g (20 mmol) of 1-phenyl-3-pyrrolecarboxylic acid and 5.52 g (24 mmol) of ethyl 3-(3-chloropropyl)aminopropionate hydrochloride in 200 ml of dichloromethane, 2.43 g (24 mmol) of triethylamine, 4.60 g (24 mmol) of 1-ethyl-3-(3-dimethylaminopropyl)carbodiimide hydrochloride and 586 mg (4.8 mmol) of 4,4-dimethylaminopyridine were added successively under ice cooling and stirring, followed by stirring at room temperature for 5 hours.

Post treatment was conducted as in Example 2. The residue was purified by chromatography on a silica gel column (eluent: chloroform), whereby 6.27 g of the title compound were obtained (yield: 86%).

EXAMPLE 23

Synthesis of 3-[1-methyl-3-[N-(3-chloropropyl)]pyrrolecarboxamido]propionic Acid (Compound No. 25)

Into a solution of 118.81 g of the crude product obtained in Example 21 in 47.4 ml of THF, 237 ml (474 mmol) of a 2 N aqueous solution of sodium hydroxide, said solution having had been chilled in advance, were added dropwise under ice cooling and stirring at such a rate that the internal temperature did not exceed 5° C. The reaction mixture was then stirred at room temperature for 30 minutes.

The reaction mixture was ice-cooled and then washed with toluene. Under ice-cooling and stirring, 6 N hydrochloric acid (79 ml) was added into the water layer at such a rate that the internal temperature did not exceed 5° C., followed by extraction with dichloromethane (twice). The dichloromethane layer was washed with water and a saturated aqueous solution of sodium chloride, dried over anhydrous sodium sulfate, and then concentrated under reduced pressure, whereby 108.05 g of a crude product were obtained.

Although the product was substantially pure, a portion of the crude product was purified by chromatography on a silica gel column (eluent: 10%-methanol/chloroform). Physical data of the purified product were then measured, so that the product was confirmed to be the title compound.

EXAMPLE 24

Synthesis of 3-[1-methyl-3-[N-(3-chloropropyl)]pyrrolecarboxamido]propionic Acid Dicyclohexylamine Salt (Compound No. 26)

Into a solution of 106.68 g of the crude product obtained in Example 23 in 390 ml of ethyl acetate, 70.71 g (390 mmol) of dicyclohexylamine were added dropwise under ice cooling and stirring. After the reaction mixture was stirred under ice cooling and stirring for 30 minutes and then at room temperature for 16 hours, precipitated crystals were collected by filtration and then dried under reduced pressure, whereby 136.17 g of the title compound were obtained (yield summed up from 1-methyl-3-pyrrolecarboxylic acid: 77%).

EXAMPLE 25

Synthesis of 5-(3-chloropropyl)-1-methyl-1,4,5,6,7,8-hexahydropyrrolo[3,2-c]azepine-4,8-dione (Compound No. 17) and 5-(3-chloropropyl)-2-methyl-2,4,5,6,7,8-hexahydropyrrolo[3,4-c]azepine-4,8-dione (Compound No. 19)

A mixture of 494 mg (3.48 mmol) of phosphorus pentoxide and 3.00 g (31.2 mmol) of methanesulfonic acid was stirred at 90° C. until homogeneity, and was then ice-cooled. Into the mixture, 1.36 g (3 mmol) of Compound No. 26 were added under stirring, followed by heating with stirring at 90° C. for 30 minutes. The reaction mixture was ice-cooled, to which 16 g of ice water were added, followed by extraction with chloroform three times. The chloroform layer was washed with water and a saturated aqueous solution of sodium chloride, dried over anhydrous sodium sulfate and then concentrated under reduced pressure. The residue was separated and purified by chromatography on a silica gel column (eluent: 1%-methanol/chloroform), whereby 635 mg of Compound No. 17 and 54 mg of Compound No. 19 were obtained (yields: 83% and 7.1%, respectively).

EXAMPLE 26

Synthesis of 5-(3-chloropropyl)-1-phenyl-1,4,5,6,7,8-hexahydropyrrolo[3,2-c]azepine-4,8-dione (Compound No. 27) and 5-(3-chloropropyl)-2-phenyl-2,4,5,6,7,8-hexahydropyrrolo[3,4-c]azepine-4,8-dione (Compound No. 28)

A mixture of 2.90 g (8 mmol) of Compound No. 24 and 6 ml (12 mmol) of a 2 N aqueous solution of sodium hydroxide was stirred at room temperature for 3.5 hours.

The reaction mixture was ice-cooled, to which 2 N hydrochloric acid was added to adjust its pH to 3, followed by extraction with chloroform. The chloroform layer was washed with a saturated aqueous solution of sodium chloride, dried over anhydrous sodium sulfate and then concentrated under reduced pressure, whereby 2.88 g of a crude product were obtained.

To the crude product, a solution which had been obtained by heating a separately-prepared mixture of 852 mg (6 mmol) of phosphorus pentoxide and 8.53 g (88.8 mmol) of methanesulfonic acid at 90° C. until homogeneity was added, followed by stirring at 90° C. for 30 minutes. Post treatment and purification were conducted as in Example 25, whereby 1.50 g of Compound No. 27 and 171 mg of Compound No. 28 were obtained (yields: 59% and 6.7%, respectively).

EXAMPLE 27

Synthesis of 5-(3-chloropropyl)-8-hydroxy-1-methyl-1,4,5,6,7,8-hexahydropyrrolo[3,2-c]azepin-4-one (Compound No. 29)

Into a suspension of 1.27 g (5 mmol) of Compound No. 17 in 12.5 ml of ethanol, 189 mg (5 mmol) of sodium borohydride were added in small portions under ice cooling and stirring, and the reaction mixture was stirred at room temperature for 1 hour.

Water was then added to the reaction mixture, followed by concentration under reduced pressure. A saturated aqueous solution of sodium chloride was added to the concentrate, and the resultant mixture was extracted with chloroform (twice). The organic layer was dried over anhydrous sodium sulfate and then concentrated under reduced pressure. The residue was recrystallized from chloroform-ethyl acetate, whereby 1.01 g of the title compound were obtained (yield: 79%).

EXAMPLE 28
Synthesis of 5-(3-chloropropyl)-8-methoxy-1-methyl-1,4,5, 6,7,8-hexahydropyrrolo[3,2-c]azepin-4-one (Compound No. 30)

Into a suspension of 28 mg (0.7 mmol) of 60% sodium hydride in 5 ml of THF, a solution of 180 mg (0.7 mmol) of Compound No. 29 in 10 ml of THF was added dropwise at room temperature under stirring. The reaction mixture was refluxed for 10 minutes and then stirred at room temperature for 30 minutes. A solution of 149 mg (1.05 mmol) of methyl iodide in 5 ml of THF was then added dropwise under ice-cooling and stirring, followed by stirring at room temperature for 15 hours.

Water was added to the reaction mixture, followed by concentration under reduced pressure. A 0.1 M phosphate buffer (pH 6.0) was added to the residue, and the resulting mixture was extracted with chloroform (twice). The organic layer was washed with a saturated aqueous solution of sodium chloride, dried over anhydrous sodium sulfate and then concentrated under reduced pressure. The residue was purified by chromatography on a silica gel column (eluent: 1%-methanol-chloroform), whereby 83 mg of the title compound were obtained (yield: 44%).

EXAMPLE 29
Synthesis of 5-(3-chloropropyl)-1-methyl-1,4,5,6-tetrahydropyrrolo[3,2-c]azepin-4-one (Compound No. 31)

Compound No. 29 (100 mg, 0.39 mmol) was dissolved under heat in 6 N hydrochloric acid, followed by stirring at room temperature for 30 minutes.

Water was added to the reaction mixture, and the resultant mixture was extracted with chloroform. The organic layer was washed with a saturated aqueous solution of sodium chloride, dried over anhydrous sodium sulfate and then concentrated under reduced pressure. The residue was purified by chromatography on a silica gel column (eluent: ethyl acetate/hexane=2/1), whereby 64 mg of the title compound were obtained (yield: 69%).

EXAMPLE 30
Synthesis of 5-[2-[4-(4-fluorophenyl)piperazin-1-yl]ethyl]-1-methyl-1,4,5,6,7,8-hexahydropyrrolo[3,2-c]azepine-4,8-dione (Compound No. 32)

Into a suspension of 1.92 g (48 mmol) of 60% sodium hydride in 100 ml of DMF, a solution of 7.13 g (40 mmol) of Compound No. 9 in 150 ml of DMF was added dropwise under ice cooling and stirring over 30 minutes. The reaction mixture was stirred at 0° C. for 30 minutes and then at room temperature for 1.5 hours, followed by the dropwise addition of a solution of 14.56 g (60 mmol) of 1-(2-chloroethyl)-4-(4-fluorophenyl)piperazine in 150 ml of DMF at 0° C. over 30 minutes. The resulting mixture was stirred at room temperature for 16 hours.

The reaction mixture was concentrated under reduced pressure. A half-saturated aqueous solution of potassium carbonate was added to the residue, followed by extraction with chloroform (twice). The organic layer was washed with a saturated aqueous solution of sodium chloride, dried over anhydrous sodium sulfate and then concentrated under reduced pressure. The residue was washed with hexane and then purified twice by chromatography on a silica gel column (eluent: 2%-methanol/chloroform, ethyl acetate), whereby 2.77 g of the title compound were obtained (yield: 18%).

EXAMPLE 31
Synthesis of 5-[3-[4-(4-fluorophenyl)piperazin-1-yl] propyl]-1-methyl-1,4,5,6,7,8-hexahydropyrrolo-[3,2-c] azepine-4,8-dione (Compound No. 33)

A suspension of 611 mg (2.4 mmol) of Compound No. 17, 649 mg (3.6 mmol) of 1-(4-fluorophenyl)piperazine, 498 mg (3.6 mmol) of potassium carbonate and 720 mg (4.8 mmol) of sodium iodide in 30 ml of acetonitrile was refluxed for 38 hours.

The reaction mixture was concentrated under reduced pressure. A half-saturated aqueous solution of potassium carbonate was added to the residue, followed by extraction with chloroform (twice). The organic layer was washed with a saturated aqueous solution of sodium chloride, dried over anhydrous sodium sulfate and then concentrated under reduced pressure. The residue was purified by chromatography on a silica gel column (eluent: 10%-methanol/ethyl acetate), whereby 1.02 g of the title compound were obtained (yield: 99%).

EXAMPLE 32
Synthesis of 5-[4-[4-(4-fluorophenyl)piperazin-1-yl]butyl]-1-methyl-1,4,5,6,7,8-hexahydropyrrolo[3,2-c]azepine-4,8-dione (Compound No. 34)

Using 403 mg (1.5 mmol) of Compound No. 18, 406 mg (2.25 mmol) of 1-(4-fluorophenyl)piperazine, 311 mg (2.25 mmol) of potassium carbonate, 450 mg (3 mmol) of sodium iodide and 22.5 ml of acetonitrile, 558 mg of the title compound were obtained in a similar manner as in Example 31 (yield: 90%).

EXAMPLE 33
Synthesis of 5-[3-[4-(4-fluorophenyl)piperazin-1-yl] propyl]-1,3-dimethyl-1,4,5,6,7,8-hexahydropyrrolo[3,2-c] azepine-4,8-dione (Compound No. 35)

Using 557 mg (2 mmol) of Compound No. 21, 541 mg (3 mmol) of 1-(4-fluorophenyl)piperazine, 415 mg (3 mmol) of potassium carbonate, 600 mg (4 mmol) of sodium iodide and 30 ml of acetonitrile, 662 mg of the title compound were obtained in a similar manner as in Example 31 (yield: 80%).

EXAMPLE 34
Synthesis of 1-ethyl-5-[3-[4-(4-fluorophenyl)piperazin-1-yl]propyl]-1,4,5,6,7,8-hexahydropyrrolo-[3,2-c]azepine-4,8-dione (Compound No. 36)

Using 146 mg (0.54 mmol) of Compound No. 20, 147 mg (0.81 mmol) of 1-(4-fluorophenyl)piperazine, 113 mg (0.81 mmol) of potassium carbonate, 163 mg (1.09 mmol) of sodium iodide and 8 ml of acetonitrile, 135 mg of the title compound were obtained in a similar manner as in Example 31 (yield: 61%).

EXAMPLE 35
Synthesis of 5-[3-[4-(4-fluorophenyl)piperazin-1-yl] propyl]-1-phenyl-1,4,5,6,7,8-hexahydropyrrolo-[3,2-c] azepine-4,8-dione (Compound No. 37)

Using 634 mg (2 mmol) of Compound No. 27, 433 mg (2.4 mmol) of 1-(4-fluorophenyl)piperazine, 332 mg (2.4 mmol) of potassium carbonate, 600 mg (4 mmol) of sodium iodide and 30 ml of acetonitrile, 856 mg of the title compound were obtained in a similar manner as in Example 31 (yield: 93%).

EXAMPLE 36

Synthesis of 1-benzyl-5-[3-[4-(4-fluorophenyl)piperazin-1-yl]propyl]-1,4,5,6,7,8-hexahydropyrrolo-[3,2-c]azepine-4,8-dione (Compound No. 38)

Using 529 mg (1.6 mmol) of Compound No. 22, 346 mg (1.92 mmol) of 1-(4-fluorophenyl)piperazine, 265 mg (1.92 mmol) of potassium carbonate, 480 mg (3.2 mmol) of sodium iodide and 20 ml of acetonitrile, 712 mg of the title compound were obtained in a similar manner as in Example 31 (yield: 94%).

EXAMPLE 37

Synthesis of 5-[3-[4-(4-fluorophenyl)piperazin-1-yl]propyl]-2-methyl-2,4,5,6,7,8-hexahydropyrrolo-[3,4-c]azepine-4,8-dione (Compound No. 39)

Using 382 mg (1.5 mmol) of Compound No. 19, 406 mg (2.25 mmol) of 1-(4-fluorophenyl)piperazine, 311 mg (2.25 mmol) of potassium carbonate, 450 mg (3 mmol) of sodium iodide and 30 ml of acetonitrile, 512 mg of the title compound were obtained in a similar manner as in Example 31 (yield: 86%).

EXAMPLE 38

Synthesis of 1-methyl-5-[3-(4-phenylpiperazin-1-yl)propyl]-1,4,5,6,7,8-hexahydropyrrolo[3,2-c]azepine-4,8-dione (Compound No. 40)

Using 509 mg (2 mmol) of Compound No. 17, 487 mg (3 mmol) of 1-phenylpiperazine, 415 mg (3 mmol) of potassium carbonate, 600 mg (4 mmol) of sodium iodide and 30 ml of acetonitrile, 726 mg of the title compound were obtained in a similar manner as in Example 31 (yield: 95%).

EXAMPLE 39

Synthesis of 5-[3-[4-(3-fluorophenyl)piperazin-1-yl]propyl]-1-methyl-1,4,5,6,7,8-hexahydropyrrolo-[3,2-c]azepine-4,8-dione (Compound No. 41)

Using 255 mg (1 mmol) of Compound No. 17, 261 mg (1 mmol) of 1-(3-fluorophenyl)piperazine hydrobromide, 336 mg (4 mmol) of sodium hydrogencarbonate, 300 mg (2 mmol) of sodium iodide and 15 ml of acetonitrile, 386 mg of the title compound were obtained in a similar manner as in Example 31 (yield: 97%).

EXAMPLE 40

Synthesis of 5-[3-[4-(2-fluorophenyl)piperazin-1-yl]propyl]-1-methyl-1,4,5,6,7,8-hexahydropyrrolo-[3,2-c]azepine-4,8-dione (Compound No. 42)

Using 255 mg (1 mmol) of Compound No. 17, 217 mg (1 mmol) of 1-(2-fluorophenyl)piperazine hydrochloride, 336 mg (4 mmol) of sodium hydrogencarbonate, 300 mg (2 mmol) of sodium iodide and 15 ml of acetonitrile, 356 mg of the title compound were obtained in a similar manner as in Example 31 (yield: 89%).

EXAMPLE 41

Synthesis of 5-[3-[4-(4-hydroxyphenyl)piperazin-1-yl]propyl]-1-methyl-1,4,5,6,7,8-hexahydropyrrolo-[3,2-c]azepine-4,8-dione (Compound No. 43)

Using 255 mg (1 mmol) of Compound No. 17, 259 mg (1 mmol) of 1-(4-hydroxyphenyl)piperazine hydrobromide, 336 mg (4 mmol) of sodium hydrogencarbonate, 300 mg (2 mmol) of sodium iodide and 15 ml of acetonitrile, 250 mg of the title compound were obtained in a similar manner as in Example 31 (yield: 63%).

EXAMPLE 42

Synthesis of 5-[3-[4-(4-chlorophenyl)piperazin-1-yl]propyl]-1-methyl-1,4,5,6,7,8-hexahydropyrrolo-[3,2-c]azepine-4,8-dione (Compound No. 44)

Using 255 mg (1 mmol) of Compound No. 17, 233 mg (1 mmol) of 1-(4-chlorophenyl)piperazine hydrochloride, 336 mg (4 mmol) of sodium hydrogencarbonate, 300 mg (2 mmol) of sodium iodide and 15 ml of acetonitrile, 415 mg of the title compound were obtained in a similar manner as in Example 31 (yield: 100%).

EXAMPLE 43

Synthesis of 1-methyl-5-[3-[4-(4-nitrophenyl)piperazin-1-yl]propyl]-1,4,5,6,7,8-hexahydropyrrolo-[3,2-c]azepine-4,8-dione (Compound No. 45)

Using 255 mg (1 mmol) of Compound No. 17, 207 mg (1 mmol) of 1-(4-nitrophenyl)piperazine, 168 mg (2 mmol) of sodium hydrogencarbonate, 300 mg (2 mmol) of sodium iodide and 15 ml of acetonitrile, 383 mg of the title compound were obtained in a similar manner as in Example 31 (yield: 90%).

EXAMPLE 44

Synthesis of 5-[3-[4-(4-methoxyphenyl)piperazin-1-yl]propyl]-1-methyl-1,4,5,6,7,8-hexahydropyrrolo-[3,2-c]azepine-4,8-dione (Compound No. 46)

Using 255 mg (1 mmol) of Compound No. 17, 264 mg (1 mmol) of 1-(4-methoxyphenyl)piperazine dihydrochloride, 504 mg (6 mmol) of sodium hydrogencarbonate, 300 mg (2 mmol) of sodium iodide and 15 ml of acetonitrile, 409 mg of the title compound were obtained in a similar manner as in Example 31 (yield: 100%).

EXAMPLE 45

Synthesis of 1-methyl-5-[3-[4-(2-pyrimidinyl)piperazin-1-yl]propyl]-1,4,5,6,7,8-hexahydropyrrolo-[3,2-c]azepine-4,8-dione (Compound No. 47)

Using 255 mg (1 mmol) of Compound No. 17, 237 mg (1 mmol) of 1-(2-pyrimidinyl)piperazine dihydrochloride, 504 mg (6 mmol) of sodium hydrogencarbonate, 300 mg (2 mmol) of sodium iodide and 15 ml of acetonitrile, 375 mg of the title compound were obtained in a similar manner as in Example 31 (yield: 98%).

EXAMPLE 46

Synthesis of 5-[3-(4-diphenylmethylpiperazin-1-yl)propyl]-1-methyl-1,4,5,6,7,8-hexahydropyrrolo-[3,2-c]azepine-4,8-dione (Compound No. 48)

Using 255 mg (1 mmol) of Compound No. 17, 252 mg (1 mmol) of 1-diphenylmethylpiperazine, 168 mg (2 mmol) of sodium hydrogencarbonate, 300 mg (2 mmol) of sodium iodide and 15 ml of acetonitrile, 380 mg of the title compound were obtained in a similar manner as in Example 31 (yield: 81%).

EXAMPLE 47

Synthesis of 1-methyl-5-[3-(4-phenylpiperidino)propyl]-1,4,5,6,7,8-hexahydropyrrolo[3,2-c]azepine-4,8-dione (Compound No. 49)

Using 255 mg (1 mmol) of Compound No. 17, 161 mg (1 mmol) of 4-phenylpiperidine, 168 mg (2 mmol) of sodium hydrogencarbonate, 300 mg (2 mmol) of sodium iodide and 15 ml of acetonitrile, 345 mg of the title compound were obtained in a similar manner as in Example 31 (yield: 91%).

EXAMPLE 48

Synthesis of 5-[3-[4-(6-fluoro-1,2-benzisoxazol-3-yl) piperidino]propyl]-1-methyl-1,4,5,6,7,8-hexahydropyrrolo [3,2-c]azepine-4,8-dione (Compound No. 50)

Using 255 mg (1 mmol) of Compound No. 17, 220 mg (1 mmol) of 4-(6-fluoro-1,2-benzisoxazol-3-yl)piperidine, 168 mg (2 mmol) of sodium hydrogencarbonate, 300 mg (2 mmol) of sodium iodide and 15 ml of acetonitrile, 404 mg of the title compound were obtained in a similar manner as in Example 31 (yield: 92%).

EXAMPLE 49

Synthesis of 5-[3-[4-(4-fluorobenzoyl)piperidino]-propyl]-1-methyl-1,4,5,6,7,8-hexahydropyrrolo[3,2-c]azepine-4,8-dione (Compound No. 51)

Using 127 mg (0.5 mmol) of Compound No. 17, 122 mg (0.5 mmol) of 4-(4-fluorobenzoyl)piperidine hydrochloride, 168 mg (2 mmol) of sodium hydrogencarbonate, 150 mg (1 mmol) of sodium iodide and 15 ml of acetonitrile, 176 mg of the title compound were obtained in a similar manner as in Example 31 (yield: 83%).

EXAMPLE 50

Synthesis of 5-[3-[4-(4-fluorophenyl)piperazin-1-yl] propyl]-1-methyl-1,4,5,6,7,8-hexahydropyrrolo-[3,2-c] azepin-4-one-8-spiro-2'-(1',3'-dithiolane) (Compound No. 52)

Into a solution of 398 mg (1 mmol) of Compound No. 33 and 168 μl (2 mmol) of 1,2-ethanedithiol in 15 ml of acetic acid, 246 μl (2 mmol) of boron trifluoride-ethyl ether complex were slowly added, followed by stirring at room temperature.

Twenty-four hours later, 1.5 ml (18 mmol) of 1,2-ethanedithiol and 1.97 ml (18 mmol) of boron trifluoride-ethyl ether complex were added further. The resultant mixture was stirred for 48 hours.

A 2 N aqueous solution of sodium hydroxide was added into the reaction mixture to alkalinize the same, followed by extraction with chloroform (twice). The organic layer was washed with a saturated aqueous solution of sodium chloride, dried over anhydrous sodium sulfate and then concentrated under reduced pressure. The residue was purified by chromatography on a silica gel column (eluent: 10%-methanol/ethyl acetate), whereby 373 mg of the title compound were obtained (yield: 79%).

EXAMPLE 51

Synthesis of 5-[3-[4-(4-fluorophenyl)piperazin-1-yl] propyl]-8-hydroxyimino-1-methyl-1,4,5,6,7,8-hexahydropyrrolo[3,2-c]azepin-4-one (Compound No. 53)

A solution of 95 mg (0.24 mmol) of Compound No. 33 and 84 mg (1.2 mmol) of hydroxylamine hydrochloride in 5 ml of pyridine was stirred at room temperature for 2.5 hours and then at 80–90° C. for 21 hours.

The reaction mixture was concentrated under reduced pressure. A half-saturated aqueous solution of potassium carbonate was added to the residue, followed by extraction with chloroform (twice). The organic layer was washed with a saturated aqueous solution of sodium chloride, dried over anhydrous sodium sulfate and then concentrated under reduced pressure. The residue was purified by chromatography on a silica gel column (eluent: 3%-methanol/ chloroform), whereby 86 mg of the title compound were obtained (yield: 83%).

EXAMPLE 52

Synthesis of 5-[3-[4-(4-fluorophenyl)piperazin-1-yl] propyl]-8-[(E)-hydroxyimino]-2-methyl-2,4,5,6,7,8-hexahydropyrrolo[3,4-c]azepin-4-one (Compound No. 54) and 5-[3-[4-(4-fluorophenyl)piperazin-1-yl]propyl]-8-[(Z)-hydroxyimino]-2-methyl-2,4,5,6,7, 8-hexahydropyrrolo[3,4-c]azepin-4-one (Compound No. 55)

A solution of 120 mg (0.3 mmol) of Compound No. 39 and 104 mg (1.5 mmol) of hydroxylamine hydrochloride in 15 ml of pyridine was stirred at 100° C. for 17 hours.

The reaction mixture was concentrated under reduced pressure. Water and toluene were added, and the resultant mixture was concentrated again under reduced pressure. A saturated aqueous solution of sodium hydrogencarbonate was added to the residue, followed by extraction with chloroform (three times). The organic layer was washed with a saturated aqueous solution of sodium chloride, dried over anhydrous sodium sulfate and then concentrated under reduced pressure. The residue was separated and purified by chromatography on a silica gel column (eluent: 6%-methanol-chloroform), whereby 81 mg of Compound No. 54 and 44 mg of Compound No. 55 were obtained (yields: 65% and 35%, respectively).

EXAMPLE 53

Synthesis of 5-[2-[4-(4-fluorophenyl)piperazin-1-yl]ethyl]-8-hydroxy-1-methyl-1,4,5,6,7,8-hexahydropyrrolo[3,2-c] azepin-4-one (Compound No. 56)

Into a solution of 384 mg (1 mmol) of Compound No. 32 in 15 ml of ethanol, 378 mg (10 mmol) of sodium borohydride were added in small portions under ice cooling and stirring. The reaction mixture was stirred at 0° C. for 30 minutes and then at room temperature for 16 hours.

Water was added to the reaction mixture. The resulting mixture was stirred at room temperature for 7 hours, and was then concentrated under reduced pressure. Water was added to the residue, followed by extraction with chloroform. The organic layer was washed with a saturated aqueous solution of sodium chloride, dried over anhydrous sodium sulfate and then concentrated under reduced pressure. The residue was purified by chromatography on a silica gel column (eluent: 3%-methanol/chloroform), whereby 376 mg of the title compound were obtained (yield: 97%).

EXAMPLE 54

Synthesis of 5-[3-[4-(4-fluorophenyl)piperazin-1-yl] propyl]-8-hydroxy-1-methyl-1,4,5,6,7,8-hexahydropyrrolo [3,2-c]azepin-4-one (Compound No. 57)

Using 956 mg (2.4 mmol) of Compound No. 33, 908 mg (24 mmol) of sodium borohydride and 30 ml of ethanol, 708 mg of the title compound were obtained in a similar manner as in Example 53 (yield: 74%).

EXAMPLE 55

Synthesis of 5-[4-[4-(4-fluorophenyl)piperazin-1-yl]butyl]-8-hydroxy-1-methyl-1,4,5,6,7,8-hexahydropyrrolo[3,2-c] azepin-4-one (Compound No. 58)

Using 206 mg (0.5 mmol) of Compound No. 34, 95 mg (2.5 mmol) of sodium borohydride and 15 ml of ethanol, 252 mg of the title compound were obtained in a similar manner as in Example 53 (yield: 94%).

EXAMPLE 56

Synthesis of 5-[3-[4-(4-fluorophenyl)piperazin-1-yl] propyl]-8-hydroxy-1,3-dimethyl-1,4,5,6,7,8-hexahydropyrrolo[3,2-c]azepin-4-one (Compound No. 59)

Using 600 mg (1.45 mmol) of Compound No. 35, 600 mg (15.9 mmol) of sodium borohydride and 20 ml of ethanol, 368 mg of the title compound were obtained in a similar manner as in Example 53 (yield: 61%).

EXAMPLE 57

Synthesis of 1-ethyl-5-[3-[4-(4-fluorophenyl)piperazin-1-yl]propyl]-8-hydroxy-1,4,5,6,7,8-hexahydropyrrolo[3,2-c]azepin-4-one (Compound No. 60)

Using 135 mg (0.33 mmol) of Compound No. 36, 150 mg (3.97 mmol) of sodium borohydride and 5 ml of ethanol, 130 mg of the title compound were obtained in a similar manner as in Example 53 (yield: 95%).

EXAMPLE 58

Synthesis of 5-[3-[4-(4-fluorophenyl)piperazin-1-yl]propyl]-8-hydroxy-1-phenyl-1,4,5,6,7,8-hexahydropyrrolo[3,2-c]azepin-4-one (Compound No. 61)

Using 461 mg (1 mmol) of Compound No. 37, 378 mg (10 mmol) of sodium borohydride and 15 ml of ethanol, 458 mg of the title compound were obtained in a similar manner as in Example 53 (yield: 99%).

EXAMPLE 59

Synthesis of 1-benzyl-5-[3-[4-(4-fluorophenyl)piperazin-1-yl]propyl]-8-hydroxy-1,4,5,6,7,8-hexahydropyrrolo[3,2-c]azepin-4-one (Compound No. 62)

Using 475 mg (1 mmol) of Compound No. 38, 378 mg (10 mmol) of sodium borohydride and 15 ml of ethanol, 403 mg of the title compound were obtained in a similar manner as in Example 53 (yield: 85%).

EXAMPLE 60

Synthesis of 5-[3-[4-(4-fluorophenyl)piperazin-1-yl]propyl]-8-hydroxy-2-methyl-2,4,5,6,7,8-hexahydropyrrolo[3,4-c]azepin-4-one (Compound No. 63)

Using 100 mg (0.25 mmol) of Compound No. 39, 100 mg (2.64 mmol) of sodium borohydride and 20 ml of ethanol, 104 mg of the title compound were obtained in a similar manner as in Example 53 (yield: 99%).

EXAMPLE 61

Synthesis of 8-hydroxy-1-methyl-5-[3-(4-phenylpiperazin-1-yl)propyl]-1,4,5,6,7,8-hexahydropyrrolo-[3,2-c]azepin-4-one (Compound No. 64)

Using 266 mg (0.7 mmol) of Compound No. 40, 132 mg (3.5 mmol) of sodium borohydride and 10 ml of ethanol, 252 mg of the title compound were obtained in a similar manner as in Example 53 (yield: 94%).

EXAMPLE 62

Synthesis of 5-[3-[4-(3-fluorophenyl)piperazin-1-yl]propyl]-8-hydroxy-1-methyl-1,4,5,6,7,8-hexahydropyrrolo[3,2-c]azepin-4-one (Compound No. 65)

Using 279 mg (0.7 mmol) of Compound No. 41, 265 mg (7 mmol) of sodium borohydride and 10 ml of ethanol, 235 mg of the title compound were obtained in a similar manner as in Example 53 (yield: 84%).

EXAMPLE 63

Synthesis of 5-[3-[4-(2-fluorophenyl)piperazin-1-yl]propyl]-8-hydroxy-1-methyl-1,4,5,6,7,8-hexahydropyrrolo[3,2-c]azepin-4-one (Compound No. 66)

Using 239 mg (0.6 mmol) of Compound No. 42, 227 mg (6 mmol) of sodium borohydride and 10 ml of ethanol, 196 mg of the title compound were obtained in a similar manner as in Example 53 (yield: 82%).

EXAMPLE 64

Synthesis of 8-hydroxy-5-[3-[4-(4-hydroxyphenyl)piperazin-1-yl]propyl]-1-methyl-1,4,5,6,7,8-hexahydropyrrolo[3,2-c]azepin-4-one (Compound No. 67)

Using 159 mg (0.4 mmol) of Compound No. 43, 151 mg (4 mmol) of sodium borohydride and 10 ml of ethanol, 122 mg of the title compound were obtained in a similar manner as in Example 53 (yield: 77%).

EXAMPLE 65

Synthesis of 5-[3-[4-(4-chlorophenyl)piperazin-1-yl]propyl]-8-hydroxy-1-methyl-1,4,5,6,7,8-hexahydropyrrolo[3,2-c]azepin-4-one (Compound No. 68)

Using 290 mg (0.7 mmol) of Compound No. 44, 265 mg (7 mmol) of sodium borohydride and 10 ml of ethanol, 260 mg of the title compound were obtained in a similar manner as in Example 53 (yield: 89%).

EXAMPLE 66

Synthesis of 8-hydroxy-1-methyl-5-[3-[4-(4-nitrophenyl)piperazin-1-yl]propyl]-1,4,5,6,7,8-hexahydropyrrolo[3,2-c]azepin-4-one (Compound No. 69)

Using 255 mg (0.6 mmol) of Compound No. 45, 227 mg (6 mmol) of sodium borohydride and 10 ml of ethanol, 248 mg of the title compound were obtained in a similar manner as in Example 53 (yield: 97%).

EXAMPLE 67

Synthesis of 8-hydroxy-5-[3-[4-(4-methoxyphenyl)piperazin-1-yl]propyl]-1-methyl-1,4,5,6,7,8-hexahydropyrrolo[3,2-c]azepin-4-one (Compound No. 70)

Using 287 mg (0.7 mmol) of Compound No. 46, 265 mg (7 mmol) of sodium borohydride and 10 ml of ethanol, 242 mg of the title compound were obtained in a similar manner as in Example 53 (yield: 84%).

EXAMPLE 68

Synthesis of 8-hydroxy-1-methyl-5-[3-[4-(2-pyrimidinyl)piperazin-1-yl]propyl]-1,4,5,6,7,8-hexahydropyrrolo[3,2-c]azepin-4-one (Compound No. 71)

Using 268 mg (0.7 mmol) of Compound No. 47, 265 mg (7 mmol) of sodium borohydride and 10 ml of ethanol, 220 mg of the title compound were obtained in a similar manner as in Example 53 (yield: 82%).

EXAMPLE 69

Synthesis of 5-[3-(4-diphenylmethylpiperazin-1-yl)propyl]-8-hydroxy-1-methyl-1,4,5,6,7,8-hexahydropyrrolo[3,2-c]azepin-4-one (Compound No. 72)

Using 282 mg (0.6 mmol) of Compound No. 48, 227 mg (6 mmol) of sodium borohydride and 10 ml of ethanol, 234 mg of the title compound were obtained in a similar manner as in Example 53 (yield: 83%).

EXAMPLE 70

Synthesis of 8-hydroxy-1-methyl-5-[3-(4-phenylpiperidino)propyl]-1,4,5,6,7,8-hexahydropyrrolo-[3,2-c]azepin-4-one (Compound No. 73)

Using 228 mg (0.6 mmol) of Compound No. 49, 227 mg (6 mmol) of sodium borohydride and 10 ml of ethanol, 199 mg of the title compound were obtained in a similar manner as in Example 53 (yield: 87%).

EXAMPLE 71

Synthesis of 5-[3-[4-(6-fluoro-1,2-benzisoxazol-3-yl)piperidino]propyl]-8-hydroxy-1-methyl-1,4,5,6,7,8-hexahydropyrrolo[3,2-c]azepin-4-one (Compound No. 74)

Using 307 mg (0.7 mmol) of Compound No. 50, 265 mg (7 mmol) of sodium borohydride and 10 ml of ethanol, 272 mg of the title compound were obtained in a similar manner as in Example 53 (yield: 88%).

EXAMPLE 72

Synthesis of 5-[3-[4-(4-fluorobenzoyl)piperidino]-propyl]-8-hydroxy-1-methyl-1,4,5,6,7,8-hexahydropyrrolo[3,2-c]azepin-4-one (Compound No. 75)

Using 642 mg (2.5 mmol) of Compound No. 29, 609 mg (2.5 mmol) of 4-(4-fluorobenzoyl)piperidine hydrochloride, 840 mg (10 mmol) of sodium hydrogencarbonate, 749 mg (5 mmol) of sodium iodide and 50 ml of acetonitrile, 837 mg of the title compound were obtained in a similar manner as in Example 31 (yield: 78%).

EXAMPLE 73

Synthesis of 5-[3-[4-(4-chlorophenyl)piperazin-1-yl]propyl]-8-methoxy-1-methyl-1,4,5,6,7,8-hexahydropyrrolo[3,2-c]azepin-4-one (Compound No. 76)

Using 81 mg (0.3 mmol) of Compound No. 30, 70 mg (0.3 mmol) of 1-(4-chlorophenyl)piperazine hydrochloride, 101 mg (1.2 mmol) of sodium hydrogencarbonate, 90 mg (0.6 mmol) of sodium iodide and 10 ml of acetonitrile, 77 mg of the title compound were obtained in a similar manner as in Example 31 (yield: 60%).

EXAMPLE 74

Synthesis of 5-[3-[4-(4-fluorophenyl)piperazin-1-yl]propyl]-8-methoxy-1-methyl-1,4,5,6,7,8-hexahydropyrrolo[3,2-c]azepin-4-one (Compound No. 77)

Using 480 mg (1.2 mmol) of Compound No. 57, 48 mg (1.2 mmol) of 60% sodium hydride, 170 mg (1.2 mmol) of methyl iodide and 20 ml of THF, 480 mg of the title compound were obtained in a similar manner as in Example 28 (yield: 97%).

EXAMPLE 75

Synthesis of 5-[3-[4-(4-fluorophenyl)piperazin-1-yl]propyl]-1-methyl-1,4,5,6-tetrahydropyrrolo[3,2-c]azepin-4-one (Compound No. 78)

A solution of 120 mg (0.3 mmol) of Compound No. 57 in 30 ml of hydrogen chloride-chloroform was stirred at room temperature for 2 hours.

A saturated aqueous solution of sodium hydrogencarbonate was added to the reaction mixture, followed by extraction with chloroform (twice). The organic layer was washed with a saturated aqueous solution of sodium chloride, dried over anhydrous sodium sulfate and then concentrated under reduced pressure. The residue was purified by chromatography on a silica gel column (eluent: 3%-methanol/chloroform), whereby 105 mg of the title compound were obtained (yield: 92%).

EXAMPLE 76

Synthesis of 5-[3-[4-(4-chlorophenyl)piperazin-1-yl]propyl]-1-methyl-1,4,5,6-tetrahydropyrrolo[3,2-c]azepin-4-one (Compound No. 79)

Into a solution of 83 mg (0.2 mmol) of Compound No. 68 in 10 ml of chloroform, 3 ml of a saturated hydrogen chloride/ethyl acetate solution and 5 ml of chloroform were added under ice cooling and stirring, followed by stirring at 0° C. for 1 hour. Further, 5 ml of 4 N hydrochloric acid were added, followed by stirring at room temperature for 2 hours. Post treatment and purification were conducted as in Example 75, whereby 78 mg of the title compound were obtained (yield: 98%).

EXAMPLE 77

Synthesis of 5-[3-[4-(4-fluorobenzoyl)piperidino]-propyl]-1-methyl-1,4,5,6-tetrahydropyrrolo]3,2-c]azepin-4-one (Compound No. 80)

Using 43 mg (0.1 mmol) of Compound No. 75, 3 ml of a saturated hydrogen chloride/ethyl acetate solution, 5 ml of 4 N hydrochloric acid and 15 ml of chloroform, 35 mg of the title compound were obtained in a similar manner as in Example 76 (yield: 85%).

EXAMPLE 78

Synthesis of 5-[3-[4-(4-chlorophenyl)piperazin-1-yl]propyl]-1-methyl-1,4,5,6,7,8-hexahydropyrrolo-[3,2-c]azepin-4-one (Compound No. 81)

In a reactor, 125 mg of 10%-palladium/carbon were placed. A solution of 477 mg (2 mmol) of Compound No. 31 in 30 ml of ethanol and 5 droplets of acetic acid were added, followed by stirring under a hydrogen gas stream at room temperature for 19 hours. The reaction mixture was filtered and the solid matter was washed with chloroform. The filtrate and the washing were combined, followed by concentration under reduced pressure. The residue was purified by chromatography on a silica gel column (eluent: ethyl acetate/hexane=3/1). The semisolid matter so obtained was dissolved in chloroform, followed by the addition of ethyl acetate. Precipitated crystals were removed by filtration, and the mother liquor was concentrated. To the residue, 187 mg (0.8 mmol) of 1-(4-chlorophenyl)piperazine hydrochloride, 269 mg (3.2 mmol) of sodium hydrogencarbonate, 240 mg (1.6 mmol) of sodium iodide and 15 ml of acetonitrile were added. The thus-obtained mixture was refluxed for 15 hours.

Post treatment and purification were conducted as in Example 31, whereby 158 mg of the title compound were obtained (yield: 49%).

EXAMPLE 79

Synthesis of 5-[3-[4-(4-fluorophenyl)piperazin-1-yl]propyl]-1-methyl-1,4,5,6,7,8-hexahydropyrrolo-[3,2-c]azepin-4-one (Compound No. 82)

Into a suspension of 50 mg of 10%-palladium/carbon in 10 ml of ethanol, a solution of 210 mg (0.55 mmol) of Compound No. 78 in 20 ml of ethanol and 5 droplets of acetic acid were added. The resultant mixture was stirred under a hydrogen gas stream at room temperature for 20 hours. The reaction mixture was filtered and the solid matter was washed with chloroform. The filtrate and the washing were combined, followed by concentration under reduced pressure.

A half-saturated aqueous solution of sodium hydrogencarbonate was added to the residue, followed by extraction with chloroform (three times). The organic layer was washed with a saturated aqueous solution of sodium chloride, dried over anhydrous sodium sulfate and then concentrated under reduced pressure. The residue was purified by chromatography on a silica gel column (eluent: ethyl acetate/methanol=5/1), whereby 210 mg of the title compound were obtained (yield: 100%).

Physical data of the compounds obtained above in Examples 1–79 are shown in Tables 1–21.

TABLE 1

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 1 | (1-methylpyrrol-3-yl)-C(=O)NH-CH$_2$CH$_2$-COOBzl | Colorless needle crystals 109.0–110.0° C. (ethyl acetate-hexane) | (270MHz) 2.66(2H, t, J=5.9Hz), 3.64(3H, s), 3.65(2H, m), 5.14(2H, s), 6.28 (1H, dd, J=2.0Hz, 2.6Hz), 6.33(1H, br.s), 6.53(1H, dd, J=2.0Hz, 2.6Hz), 7.11 (1H, t, J=2.0Hz), 7.29~7.41(5H, m) | (KBr) 3270, 1732, 1623, 1558, 1315, 1272, 1247, 1207, 1177, 1032, 962, 821, 753, 698 |
| 2 | (1-ethylpyrrol-3-yl)-C(=O)NH-CH$_2$CH$_2$-COOEt | Yellow oil | (400MHz) 1.25(3H, t, J=8.2Hz), 1.42 (3H, t, J=8.2Hz), 2.59(2H, t, J=8.0Hz), 3.65(2H, t, J=8.0Hz), 3.93 (2H, q, J=8.2Hz), 4.16(2H, q, J=8.2Hz), 6.32(1H, m), 6.34(1H, br.s), 6.61(1H, m), 7.21(1H, m) | (film) 3324, 2981, 1732, 1634, 1558, 1505, 1446, 1372, 1250, 1184, 1073, 1035, 821, 759 |
| 3 | (pyrrol-3-yl)-C(=O)NH-CH$_2$CH$_2$-COOBzl | Brown oil | (270MHz) 2.64(2H, t, J=5.9Hz), 3.65(2H, m), 5.11(2H, s), 6.33(1H, m), 6.59(1H, br.s), 6.68(1H, m), 7.22(1H, m), 7.29~7.31(5H, m), 9.90(1H, br.s) | (film) 3271, 2954, 1732, 1634, 1567, 1520, 1338, 1254, 1210, 1172, 756, 698, |
| 4 | (4-methylpyrrol-3-yl)-C(=O)NH-CH$_2$CH$_2$-COOEt | Pale brown oil | (400MHz) 1.26(3H, t, J=7.1Hz), 2.25(3H, s), 2.64(2H, t, J=6.0Hz), 3.71(2H, t, J=6.0Hz), 4.16(2H, q, J=7.1Hz), 6.52(1H, s), 7.40(1H, s), 9.62 (1H, br.s) | (film) 3246, 2980, 1719, 1624, 1534, 1448, 1375, 1329, 1256, 1188, 1074, 1028, 775 |

*Measured in CDCl$_3$ with TMS as an internal standard unless otherwise specifically indicated.

TABLE 2

| Comp'd No. | Structural formula | Property Melting point (recrystallization solvent) | NMR (δ ppm)* ( ): observation frequency | IR (cm$^{+1}$) ( ): measuring method |
|---|---|---|---|---|
| 5 | (1-methylpyrrol-3-yl)-C(=O)NH-CH$_2$CH$_2$-COOH | Pale brown prism crystals 136.0–138.5° C. (acetonitrile) | (270MHz)(DMSO-d$_6$/TMS) 2.44(2H, t, J=7.2Hz), 3.35(2H, m), 3.61 (3H, s), 6.39(1H, m), 6.66(1H, m), 7.21 (1H, m), 7.54(1H, t, J=5.5Hz) | (KBr) 3357, 1715, 1574, 1421, 1349, 1315, 1278, 1216, 1080, 922, 837, 769, 718 |
| 6 | (1-ethylpyrrol-3-yl)-C(=O)NH-CH$_2$CH$_2$-COOH | Colorless powdery crystals 157.5–158.0° C. (acetonitrile) | (400MHz)(DMSO-d$_6$/TMS) 1.31(3H, t, J= 7.1Hz), 3.36(2H, m), 3.90(2H, q, J= 7.3Hz), 6.39(1H, m), 6.74(1H, m), 7.28(1H, m), 7.70(1H, t, J=5.3Hz), 12.23(1H, br.s) | (KBr) 3364, 2978, 1719, 1572, 1427, 1352, 1269, 1234, 1193, 854, 757, 707 |

TABLE 2-continued

| Comp'd No. | Structural formula | Property Melting point (recrystallization solvent) | NMR (δ ppm)* ( ): observation frequency | IR (cm$^{+1}$) ( ): measuring method |
|---|---|---|---|---|
| 7 | (pyrrole-3-carboxamide with -NH-CH2CH2-COOH) | Colorless needle crystals 178.5–183.0° C. (methanol-isopropyl ether) | (400MHz)(DMSO-d$_6$/TMS) 2.45(2H, t, J=7.1Hz), 3.36(2H, m), 6.43(1H, s), 6.71(1H, s), 7.26(1H, s) 7.72(1H, br.s), 11.04(1H, br.s), 12.09(1H, s) | (KBr) 3381, 3272, 1718, 1567, 1538, 1427, 1351, 1210, 853, 757 |
| 8 | (4-methylpyrrole-3-carboxamide with -NH-CH2CH2-COOH) | Colorless powdery needles 163.5–164.5° C. (isopropanol-chloroform) | (400MHz)(DMSO-d$_6$/TMS) 2.14(3H, s), 2.44(2H, t, J=7.1Hz), 3.34(2H, m), 6.50(1H, s), 7.23(1H, s), 7.53(1H, m), 10.75(1H, br.s), 12.10(1H, br.s) | (KBr) 3394, 3260, 1720, 1593, 1561, 1426, 1221, 1204, 1184, 859, 763 |

*Measured in CDCl$_3$ with TMS as an internal standard unless otherwise specifically indicated.

TABLE 3

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 9 | (N-Me pyrrolo-fused bicyclic diketone/lactam) | Colorless prism crystals 174.0–176.0° C. (acetonitrile) | (270MHz) 2.86(2H, m), 3.52(2H, m), 3.97(3H, s), 6.78(1H, d, J=2.6Hz), 6.87(1H, d, J=2.6Hz), 7.98(1H, br.s) | (KBr) 3349, 1652, 1522, 1505, 1402, 1381, 1261, 1213, 892, 770 |
| 10 | (Me-N pyrrolo-fused bicyclic) | Colorless powdery crystals 218.0–220.0° C. (acetonitrile-isopropyl ether) | (270MHz) 2.82(2H, m), 3.52(2H, m), 3.74(3H, s), 6.90(1H, br.s), 7.34~7.36(2H, m) | (KBr) 3176, 1652, 1547, 1519, 1454, 1369, 1321, 1246, 1178, 1145, 910, 811 |
| 11 | (N-Et pyrrolo-fused bicyclic) | Colorless needle crystals 146.5–149.0° C. (chloroform-hexane) | (400MHz) 1.40(3H, t, J=7.1Hz), 2.87(2H, m), 3.50 (2H, m), 4.39(2H, q, J=7.1Hz), 6.29(1H, br.s), 6.82(1H, d, J=2.7Hz), 6.94(1H, d, J=2.7Hz) | (KBr) 3185, 3046, 2938, 1668, 1643, 1526, 1501, 1414, 1386, 1310, 1279, 1257, 1214, 1194, 894, 812 |
| 12 | (N-H pyrrolo-fused bicyclic) | Colorless needle crystals 285–287° C. (decomposed) (methanol-isopropyl ether) | (400MHz) 2.71(2H, m), 3.33(2H, m), 6.57(1H, s), 7.11(1H, d, J=2.4Hz), 8.29(1H, br.s), 12.13(1H, br.s) | (KBr) 3306, 3037, 2956, 1642, 1503, 1438, 1407, 1395, 1268, 882, 762 |

*Measured in CDCl$_3$ with TMS as an internal standard unless otherwise specifically indicated.

TABLE 4

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 13 | (pyrrole fused azepine dione, NH, HN, O, O) | Colorless powdery crystals 287° C. or higher (methanol-isopropyl ether) | (400MHz) 2.65(2H, m), 3.29(2H, m), 7.34(1H, s), 7.43(1H, s), 7.80(1H, br.s), 11.97(1H, br.s) | (KBr) 3309, 3120, 3057, 2946, 2880, 1647, 1620, 1526, 1474, 1456, 1419, 1377, 1360, 910, 838, 810, 759 |
| 14 | (Me-substituted pyrrole fused azepinone, NH, H) | Colorless powdery crystals 251.0–252.5° C. (decomposed) (acetonitrile-isopropyl ether) | (400MHz)(DMSO-d$_6$/TMS) 2.20(3H, s), 2.66(2H, m), 3.29(2H, m), 6.94(1H, d, J=2.6Hz), 7.89(1H, br.s), 11.85(1H, br.s) | (KBr) 3324, 3078, 2959, 2924, 1634, 1607, 1553, 1511, 1473, 1450, 1397, 1339, 901, 803 |
| 15 | (Me-substituted N-Me pyrrole fused azepinone) | Colorless powdery crystals 183.0–183.5° C. (ethyl acetate) | (400MHz) 2.30(3H, s), 2.82(2H, m), 3.47(2H, m), 3.90(3H, s), 6.17(1H, br.s), 6.69(1H, s) | (KBr) 3187, 3064, 2928, 1639, 1501, 1442, 1406, 1379, 1319, 1262, 1206, 1047, 901, 800 |
| 16 | (N-Bzl pyrrole fused azepinone) | Colorless needle crystals 170.5–171.5° C. (ethyl acetate-hexane) | (400MHz) 2.83(2H, m), 3.49(2H, m), 5.60(2H, s), 6.78(1H, br.s), 6.87(1H, d, J=2.7Hz), 6.97(1H, d, J=2.7Hz), 7.11(2H, m), 7.24~7.34(3H, m) | (KBr) 3195, 3064, 1656, 1526, 1498, 1453, 1408, 1305, 1271, 1217, 1118, 1023, 992, 893, 752, 696 |

*Measured in CDCl$_3$ with TMS as an internal standard unless otherwise specifically indicated.

TABLE 5

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 17 | (N-(CH$_2$)$_3$Cl substituted pyrrole fused azepinone, N-Me) | Pale yellow prism crystals 110.0–113.0° C. (ethyl acetate-hexane) | (270MHz) 2.14(2H, quint, J=6.7Hz), 2.85 (2H, dd, J=4.0Hz, 6.6Hz), 3.62 (2H, t, J=6.7Hz), 3.69(2H, m), 3.75 (2H, t, J=6.7Hz), 3.95(3H, s), 6.77 (1H, d, J=2.6Hz), 6.84(1H, d, J=2.6Hz) | (KBr) 3101, 2938, 1660, 1626, 1524, 1508, 1474, 1441, 1410, 1378, 1293, 1248, 1183, 1146, 1074, 985, 914, 805, 761, 652 |
| 18 | (N-(CH$_2$)$_4$Cl substituted pyrrole fused azepinone, N-Me) | Colorless needle crystals 100.0–102.0° C. (ethyl acetate-hexane) | (400MHz) 1.76~1.91(4H, m), 2.83(2H, dd, J=, 4.0Hz, 6.4Hz), 3.57~3.69(6H, m), 3.95(3H, s), 6.76(1H, d, J=2.6Hz), 6.83(1H, d, J=2.6Hz) | (KBr) 1654, 1622, 1506, 1410, 1377, 1308, 1240, 1204, 922, 760, 744 |

TABLE 5-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 19 | (structure: pyrrolo-azepine-dione with N-Me and N-(CH$_2$)$_3$Cl) | Colorless powdery crystals | (270MHz) 2.13(2H, quint, J=6.6Hz), 2.80(2H, m), 3.62(2H, t, J=6.6Hz), 3.66(2H, m), 3.71(2H, t, J=6.6Hz), 3.73(3H, s), 7.28~7.31(2H, m) | (KBr) 3454, 3110, 2948, 1654, 1612, 1553, 1519, 1490, 1250, 1172, 1048, 940, 862, 830, 725 |
| 20 | (structure: pyrrolo-azepine-dione with N-Et and N-(CH$_2$)$_3$Cl) | Colorless oil | (400MHz) 1.39(3H, t, J=7.1Hz), 2.14(2H, quint, J=6.7Hz), 2.85(2H, m), 3.61(2H, t, J=6.7Hz), 3.68(2H, m), 3.74(2H, t, J=6.7Hz), 4.36(2H, q, J=7.1Hz), 6.78(1H, d, J=2.7Hz), 6.92(1H, d, J=2.7Hz) | (film) 1653, 1625, 1520, 1497, 1411, 1288, 1243, 912, 755 |

*Measured in CDCl$_3$ with TMS as an internal standard unless otherwise specifically indicated.

TABLE 6

| Comp'd No. | Structural formula | Property Melting point (recrystallization solvent) | NMR (δ ppm)* ( ): observation frequency | IR (cm⁻¹) ( ): measuring method |
|---|---|---|---|---|
| 21 | (structure: methyl-substituted pyrrolo-azepine-dione with N-Me and N-(CH$_2$)$_3$Cl) | Colorless oil | (400MHz) 2.14(2H, quint, J=6.7Hz), 2.27(3H, s), 2.79(2H, m), 3.54~3.68(4H, m), 3.72(2H, t, J=6.7Hz), 3.87(3H, s), 6.66(1H, s) | (film) 2954, 1627, 1500, 1443, 1377, 1247, 918, 775 |
| 22 | (structure: pyrrolo-azepine-dione with N-Bzl and N-(CH$_2$)$_3$Cl) | Colorless oil | (400MHz) 2.13(2H, m), 2.81(2H, m), 3.61 (2H, t, J=6.4Hz), 3.66(2H, m), 3.74(2H, t, J=6.9Hz), 5.57(2H, s), 6.83(1H, d, J=2.7Hz), 6.95 (1H, d, J=2.7Hz), 7.10(2H, m), 7.23~7.34(3H, m) | (film) 2943, 1627, 1522, 1496, 1411, 1287, 1244, 1188, 1074, 914, 754, 735, 705 |
| 23 | (structure: pyrrole carboxamide with N-Me, N-(CH$_2$)$_3$Cl, and COOEt) | Pale yellow oil | (400MHz) 1.26(3H, t, J=7.1Hz), 2.12(2H, m), 2.68 (2H, t, J=7.3Hz), 3.57(2H, t, J=6.4Hz), 3.62~3.68(5H, m), 3.80(2H, t, J=7.3Hz), 4.15(2H, q, J=7.1Hz), 6.33(1H, m), 6.54 (1H, t, J=2.5Hz), 7.05(1H, t, J=2.0Hz) | (film) 2980, 1730, 1611, 1540, 1474, 1448, 1424, 1375, 1273, 1188, 1051, 754 |
| 24 | (structure: pyrrole carboxamide with N-Ph, N-(CH$_2$)$_3$Cl, and COOEt) | Pale yellow oil | (400MHz) 1.27(3H, t, J=7.1Hz), 2.16(2H, m), 2.72(2H, t, J=7.3Hz), 3.60(2H, t, J=6.2Hz), 3.70(2H, m), 3.85(2H, m), 4.16(2H, q, J=7.1Hz), 6.55(1H, m), 7.03(1H, m), 7.30(1H, m), 7.38~7.48(4H, m), 7.50(1H, m) | (film) 2980, 1730, 1618, 1541, 1509, 1423, 1379, 1280, 1226, 1192, 1146, 1074, 752, 693 |

*Measured in CDCl$_3$ with TMS as an internal standard unless otherwise specifically indicated.

TABLE 7

| Comp'd No. | Structural formula | Property Melting point (recrystallization solvent) | NMR (δ ppm)* ( ): observation frequency | IR (cm⁻¹) ( ): measuring method |
|---|---|---|---|---|
| 25 | (structure: 1-methylpyrrole-3-carboxamide with N-(CH₂)₃Cl and N-CH₂CH₂COOH) | Colorless oil | (400MHz) 2.07~2.21(2H, m), 2.73(2H, t, J=7.0Hz), 3.57(2H, t, J=6.3Hz), 3.65(3H, s), 3.70 (2H, t, J=7.3Hz), 3.79(2H, t, J=6.8Hz), 6.34(1H, m), 6.55(1H, m), 7.09(1H, m) | (film) 2952, 1728, 1568, 1539, 1480, 1436, 1374, 1276, 1214, 754 |
| 26 | (structure: compound 25 · dicyclohexylamine salt) | Colorless powdery crystals | (400MHz) 1.07~1.43(10H, m), 1.60~1.69(2H, m), 1.72~1.85(4H, m), 1.92~2.05(4H, m), 2.14(2H, m), 2.56(2H, m), 2.87(2H, m), 3.57(2H, t, J=6.5Hz), 3.60~3.69(5H, m), 3.80(2H, m), 4.96(1H, br.s), 6.40(1H, s), 6.51(1H, t, J=6.9Hz), 7.08(1H, s) | (KBr) 2945, 2855, 1605, 1537, 1452, 1393, 1311, 1282, 1244, 1210, 1137, 1073, 818, 757, 710, 659 |
| 27 | (structure: N-phenyl pyrrolo-azepine-dione with N-(CH₂)₃Cl) | Colorless powdery crystals 97.0–98.5° C. (ethyl acetate-hexane) | (400MHz) 2.16(2H, m), 2.81(2H, m), 3.64 (2H, t, J=6.4Hz), 3.75~3.81(4H, m), 6.92(1H, d, J=2.8Hz), 6.99(1H, d, J=2.0Hz), 7.22~7.27(2H, m), 7.40~7.46(3H, m) | (KBr) 3097, 1669, 1655, 1626, 1525, 1497, 1411, 1377, 1322, 1291, 1267, 1190, 1160, 908, 760, 752, 700 |
| 28 | (structure: N-phenyl pyrrolo-azepine-dione isomer with N-(CH₂)₃Cl) | Colorless powdery crystals 116.5–118.0° C. (ethyl acetate-hexane) | (400MHz) 2.16(2H, m), 2.67(2H, m), 3.64 (2H, t, J=6.4Hz), 3.71~3.79(4H, m), 7.37~7.52(5H, m), 7.73(1H, d, J=2.6Hz), 7.75(1H, d, J=2.6Hz) | (KBr) 3130, 1662, 1630, 1519, 1478, 1425, 1312, 1265, 1206, 1070, 924, 762, 687 |

*Measured in CDCl₃ with TMS as an internal standard unless otherwise specifically indicated.

TABLE 8

| Comp'd No. | Structural formula | Property Melting point (recrystallization solvent) | NMR (δ ppm)* ( ): observation frequency | IR (cm⁻¹) ( ): measuring method |
|---|---|---|---|---|
| 29 | (structure: 1-methyl pyrrolo-azepinone with OH and N-(CH₂)₃Cl) | Colorless powdery crystals 107.0–108.5° C. (ethyl acetate-hexane) | (400MHz) 2.05(2H, quint, J=6.7Hz), 2.22(2H, m), 2.61(1H, d, J=7.8Hz), 3.33(1H, m), 3.52~3.69(5H, m), 3.72(3H, s), 4.85~4.90(1H, m), 6.60(1H, d, J=2.9Hz), 6.66(1H, d, J=2.9Hz) | (KBr) 3228, 2953, 1586, 1542, 1513, 1483, 1441, 1286, 1046, 956, 730 |
| 30 | (structure: 1-methyl pyrrolo-azepinone with OMe and N-(CH₂)₃Cl) | Pale yellow oil | (400MHz) 1.95(1H, m), 2.09(2H, quint, J=6.7Hz), 2.48(1H, m), 3.29(1H, m), 3.37(3H, s), 3.59(2H, t, J=6.6Hz), 3.62(3H, s), 3.63~3.76(3H, m), 4.39(1H, t, J=3.8Hz), 6.60(1H, d, J=2.9Hz), 6.69(1H, d, J=2.9Hz) | (film) 3462, 2930, 1612, 1541, 1508, 1481, 1426, 1364, 1286, 1251, 1165, 1072, 1022, 950, 866, 734 |

TABLE 8-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 31 | | Yellow oil | (400MHz) 2.07(2H, quint, J=6.6Hz), 3.56 (2H, t, J=6.4Hz), 3.62(3H, s), 3.70 (2H, t, J=6.6Hz), 3.73(2H, d, J=6.9Hz), 6.13(1H, dt, J=6.9Hz, 9.8Hz), 6.66 (1H, d, J=2.9Hz), 6.69(1H, d, J=9.8Hz), 6.74(1H, d, J=2.9Hz) | (film) 3406, 1612, 1544, 1508, 1438, 1305, 1271, 1177, 1028, 817, 731 |
| 32 | | Yellow oil | (400MHz) 2.63~2.72(6H, m), 2.93(2H, m), 3.10(4H, m), 3.67(2H, m), 3.78(2H, m), 3.95(3H, s), 6.77(1H, d, J=2.6Hz), 6.83(1H, d, J=2.6Hz), 6.85(2H, m), 6.95(2H, m) | (film) 2945, 2817, 1652, 1626, 1510, 1455, 1410, 1380, 1303, 1247, 1164, 1141, 1008, 914, 816, 760 |

*Measured in CDCl₃ with TMS as an internal standard unless otherwise specifically indicated.

TABLE 9

| Comp'd No. | Structural formula | Property Melting point (recrystallization solvent) | NMR (δ ppm)* ( ): observation frequency | IR (cm⁻¹) ( ): measuring method |
|---|---|---|---|---|
| 33 | | Yellow oil [dihydrochloride] colorless oil | (270MHz) 1.88(2H, quint, J=7.3Hz), 2.48 (2H, t, J=7.3Hz), 2.62(4H, m), 2.84(2H, m), 3.12(4H, m), 3.58~3.74(4H, m), 3.95(3H, s), 6.77(1H, d, J=2.6Hz), 6.81~7.02(5H, m) | (film) 2945, 2819, 1654, 1624, 1509, 1410, 1380, 1246, 1163, 920, 817, 748 |
| 34 | | Colorless prism crystals 139.5– 142.0° C. (ethyl acetate-hexane) | (400MHz) 1.53~1.78(4H, m), 2.44(2H, m), 2.59 (4H, m), 2.82(2H, dd, J=4.1Hz), 3.11(4H, m), 3.58~3.68(4H, m), 3.95(3H, s), 6.77(1H, d, J=2.6Hz), 6.83(1H, d, J=2.6Hz), 6.84~6.90 (2H, m), 6.90~6.98(2H, m) | (KBr) 1643, 1617, 1504, 1409, 1378, 1248, 1136, 921, 816, 762 |
| 35 | | Colorless oil | (400MHz) 1.88(2H, quint, J=7.3Hz), 2.28(3H, s), 2.48(2H, t, J=7.3Hz), 2.61(4H, m), 2.79(2H, m), 3.12(4H, m), 3.58~3.66 (4H, m), 3.87(3H, s), 6.66(1H, s), 6.87(2H, m), 6.95(2H, m) | (film) 2944, 2819, 1626, 1509, 1444, 1377, 1232, 1132, 923, 816 |

TABLE 9-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 36 |  | Colorless oil | (400MHz) 1.38(3H, t, J=7.1Hz), 1.87(2H, quint, J=7.2Hz), 2.47(2H, t, J=7.2Hz), 2.61 (4H, m), 2.84(2H, m), 3.11(4H, m), 3.64~3.68(4H, m), 4.35(2H, t, J=7.1Hz), 6.70(1H, d, J=2.6Hz), 6.84~6.96(5H, m) | (film) 2931, 2819, 1652, 1634, 1505, 1411, 1243, 910, 817, 755 |

*Measured in CDCl$_3$ with TMS as an internal standard unless otherwise specifically indicated.

TABLE 10

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 37 | | Pale yellow oil | (400MHz) 1.90(2H, m), 2.49(2H, m), 2.62(4H, m), 2.81(2H, m), 3.12(4H, m), 3.70(2H, m), 3.77(2H, m), 6.84~6.91(2H, m), 6.91~7.01(4H, m), 7.22~7.28(2H, m), 7.38~7.47(3H, m) | (film) 2944, 2819, 1665, 1628, 1510, 1456, 1412, 1376, 1307, 1264, 1234, 1163, 906, 826, 752, 697 |
| 38 | | Pale yellow oil | (400MHz) 1.87(2H, m), 2.47(2H, m), 2.61(4H, m), 2.80(2H, m), 3.11(4H, m), 3.61~3.70(4H, m), 5.57(2H, s), 6.83~6.89(3H, m), 6.91~6.98(3H, m), 7.10(2H, m), 7.23~7.33(3H, m) | (film) 2943, 2819, 1654, 1624, 1509, 1498, 1455, 1411, 1288, 1243, 1163, 920, 817, 753 |
| 39 | | Colorless powdery crystals 140.0–141.0° C. (ethyl acetate-isopropyl ether) | (270MHz) 1.87(2H, quint, J=7.3Hz), 2.47(2H, t, J=7.3Hz), 2.62(4H, m), 2.79(2H, m), 3.12(4H, m), 3.60~3.68(4H, m), 3.72(3H, s), 6.87(2H, m), 6.95(2H, m), 7.27~7.29(2H, m) | (KBr) 3122, 2544, 2822, 1654, 1615, 1547, 1511, 1482, 1433, 1374, 1247, 1234, 1181, 1134, 1028, 965, 936, 826 |
| 40 | | Pale yellow oil | (400MHz) 1.88(2H, quint, J=7.3Hz), 2.47(2H, m), 2.61(4H, m), 2.83(2H, m), 3.20(4H, m), 3.63~3.72(4H, m), 3.95(3H, s), 6.77(1H, d, J=2.6Hz), 6.80~6.87(2H, m), 6.92(2H, m), 7.25(2H, m) | (film) 1653, 1624, 1600, 1501, 1410, 1380, 1246, 760 |

*Measured in CDCl$_3$ with TMS as an internal standard unless otherwise specifically indicated.

TABLE 11

| Comp'd No. | Structural formula | Property Melting point (recrystallization solvent) | IR (cm$^{-1}$) NMR (δ ppm)* ( ): observation frequency | ( ): measuring method |
|---|---|---|---|---|
| 41 | (structure: 1-methylpyrrolo-azepine-4,8-dione with (CH$_2$)$_3$-piperazine-(3-fluorophenyl)) | Colorless oil | (400MHz) 1.87(2H, m), 2.47(2H, m), 2.50(4H, m), 2.84(2H, m), 3.20(4H, m), 3.67(4H, m), 3.95(3H, s), 6.51(1H, m), 6.58(1H, m), 6.66(1H, m), 6.77(1H, d, J=2.6Hz), 6.83(1H, d, J=2.6Hz), 7.17(1H, n) | (film) 2945, 2821, 1654, 1616, 1582, 1522, 1501, 1448, 1410, 1381, 1307, 1248, 1180, 999, 974, 914, 845, 760, 684 |
| 42 | (structure: 1-methylpyrrolo-azepine-4,8-dione with (CH$_2$)$_3$-piperazine-(2-fluorophenyl)) | Yellow oil | (400MHz) 1.88(2H, m), 2.49(2H, m), 2.64(4H, m), 2.85(2H, m), 3.12(4H, m), 3.67(4H, m), 3.95(3H, s), 6.78(1H, d, J=2.7Hz), 6.83(1H, d, J=2.7Hz), 6.88~7.08 (4H, m) | (film) 2945, 2820, 1652, 1625, 1522, 1502, 1455, 1410, 1380, 1245, 1205, 1141, 1013, 913, 802, 758 |
| 43 | (structure: 1-methylpyrrolo-azepine-4,8-dione with (CH$_2$)$_3$-piperazine-(4-hydroxyphenyl)) | Colorless powdery crystals 188.0–190.0° C. (chloroform-hexane) | (270MHz) 1.88(2H, quint, J=7.3Hz), 2.47 (2H, t, J=7.3Hz), 2.61(4H, m), 2.84(2H, dd, J=4.0Hz, 7.1Hz), 3.07(4H, m), 3.67(4H, m), 3.95(3H, s), 6.73~6.88(6H, m) | (KBr) 3366, 2947, 2820, 1659, 1612, 1514, 1504, 1448, 1407, 1381, 1306, 1246, 922, 820, 760 |
| 44 | (structure: 1-methylpyrrolo-azepine-4,8-dione with (CH$_2$)$_3$-piperazine-(4-chlorophenyl)) | Colorless oil | (400MHz) 1.87(2H, m), 2.47(2H, m), 2.60(4H, m), 2.84(2H, m), 3.16(4H, m), 3.66(4H, m), 3.95(3H, s), 6.77(1H, d, J=2.6Hz), 6.80~6.86(3H, m), 7.19(2H, m) | (film) 2946, 2821, 1653, 1624, 1522, 1499, 1410, 1380, 1305, 1246, 920, 820, 759, 675 |

*Measured in CDCl$_3$ with TMS as an internal standard unless otherwise specifically indicated.

TABLE 12

| Comp'd No. | Structural formula | Property Melting point (recrystallization solvent) | IR (cm$^{-1}$) NMR (δ ppm)* ( ): observation frequency | ( ): measuring method |
|---|---|---|---|---|
| 45 | (structure: 1-methylpyrrolo-azepine-4,8-dione with (CH$_2$)$_3$-piperazine-(4-nitrophenyl)) | Orange prism crystals 142.0–144.5° C. (ethyl acetate-hexane) | (400MHz) 1.87(2H, m), 2.50(2H, m), 2.60(4H, m), 2.84(2H, m), 3.42(4H, m), 3.67(4H, m), 3.95(3H, s), 6.77(1H, d, J=2.6Hz), 6.81(2H, m), 6.84(1H, d, J=1.6Hz), 8.12(2H, m) | (KBr) 2947, 1648, 1599, 1505, 1412, 1381, 1323, 1241, 1106, 1021, 912, 829, 754, 692 |

TABLE 12-continued

| Comp'd No. | Structural formula | Property Melting point (recrystallization solvent) | IR (cm⁻¹) NMR (δ ppm)* ( ): observation frequency | ( ): measuring method |
|---|---|---|---|---|
| 46 | (structure: 1-methylpyrrole fused azepine-dione with (CH₂)₃-piperazine-N-(4-OMe-phenyl)) | Pale brown oil | (400MHz) 1.87(2H, m), 2.47(2H, m), 2.61(4H, m), 2.83(2H, m), 3.09(4H, m), 3.66(4H, m), 3.76(3H, s), 3.95(3H, s), 6.77(1H, d, J=2.6Hz), 6.79~6.85(3H, m), 6.85~6.92(2H, m) | (film) 2945, 2816, 1653, 1626, 1512, 1456, 1410, 1380, 1246, 1181, 1035, 912, 825, 760 |
| 47 | (structure: 1-methylpyrrole fused azepine-dione with (CH₂)₃-piperazine-N-(2-pyrimidinyl)) | Pale yellow oil | (400MHz) 1.88(2H, m), 2.46(2H, m), 2.50(4H, m), 2.84(2H, m), 3.67(4H, m), 3.82(4H, m), 3.95(3H, s), 6.47(1H, t, J=4.8Hz), 6.77(1H, d, J=2.7Hz), 6.83(1H, d, J=2.7Hz), 8.29(2H, d, J=4.8Hz) | (film) 2944, 1652, 1625, 1586, 1547, 1501, 1446, 1410, 1380, 1359, 1307, 1247, 983, 797, 748 |
| 48 | (structure: 1-methylpyrrole fused azepine-dione with (CH₂)₃-piperazine-N-CHPh₂) | Colorless oil | (400MHz) 1.81(2H, m), 2.35~2.54(10H, m), 2.80(2H, m), 3.57~3.67(4H, m), 3.94(3H, s), 4.21(1H, s), 6.75 (1H, d, J=2.6Hz), 6.81(1H, d, J=2.6Hz), 7.16(2H, m), 7.25(4H, m), 7.40(4H, m) | (film) 2809, 1626, 1522, 1501, 1410, 1380, 1246, 1151, 1009, 747, 708 |

*Measured in CDCl₃ with TMS as an internal standard unless otherwise specifically indicated.

TABLE 13

| Comp'd No. | Structural formula | Property Melting point (recrystallization solvent) | IR (cm⁻¹) NMR (δ ppm)* ( ): observation frequency | ( ): measuring method |
|---|---|---|---|---|
| 49 | (structure: 1-methylpyrrole fused azepine-dione with (CH₂)₃-piperidine-4-phenyl) | Yellow oil | (400MHz) 1.72~1.94(6H, m), 2.07(2H, m), 2.42~2.55(3H, m), 2.84(2H, m), 3.06(2H, d, J=11.2Hz), 3.66(4H, m), 3.95(3H, s), 6.78(1H, d, J=2.6Hz), 6.83(1H, d, J=2.6Hz), 7.16~7.24 (3H, m), 7.24~7.32(2H, m) | (film) 2933, 1652, 1626, 1522, 1503, 1472, 1410, 1380, 1247, 760, 701 |
| 50 | (structure: 1-methylpyrrole fused azepine-dione with (CH₂)₃-piperidine-4-(6-fluorobenzisoxazol-3-yl)) | Yellow oil | (400MHz) 1.88(2H, m), 2.03~2.20(6H, m), 2.48(2H, m), 2.85(2H, m), 3.01~3.12(3H, m), 3.63~3.71(4H, m), 3.95(3H, s), 6.78(1H, d, J=2.6Hz), 6.83(1H, d, J=2.6Hz), 7.05(1H, dt, J=2.1Hz, 8.8Hz), 7.23(1H, dd, J= 2.1Hz, 8.5Hz), 7.68(1H, dd, J= 5.1Hz, 8.8Hz) | (film) 2946, 2810, 1620, 1522, 1502, 1474, 1411, 1381, 1307, 1272, 1247, 1123, 1087, 956, 914, 841, 816, 759, 666 |

TABLE 13-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 51 | | Pale yellow prism crystals 127.5–130.5° C. (ethyl acetate-hexane) | (270MHz) 1.77~1.93(6H, m), 2.10(2H, m), 2.44(2H, t, J=7.3Hz), 2.84(2H, dd, J=3.6Hz, 6.9Hz), 3.01(2H, m), 3.20(1H, m), 3.59~3.72(4H, m), 3.95(3H, s), 6.77(1H, d, J=2.6Hz), 6.83(1H, d, J=2.6Hz), 7.14(2H, t, J=8.9Hz), 7.96(2H, dd, J=5.6Hz, 8.9Hz) | (KBr) 1672, 1630, 2946, 2774, 1595, 1519, 1501, 1407, 1380, 1305, 1267, 1243, 1205, 1159, 979, 922, 854, 788, 744 |
| 52 | | Pale yellow oil [dihydrochloride] Pale yellow powdery crystals 196° C. (decomposed) (ethanol-ethyl ether) | (400MHz) 1.82(2H, quint, J=7.3Hz), 2.45 (2H, t, J=7.3Hz), 2.50(4H, m), 2.69(2H, d, J=9.1Hz), 3.11(4H, m), 3.41~3.70(8H, m), 3.99(3H, s), 6.64(1H, d, J=2.9Hz), 6.70(1H, d, J=2.9Hz), 6.86(2H, m), 6.94(2H, m) | (film) 2921, 2817, 1508, 1508, 1427, 1401, 1355, 1303, 1232, 1162, 1141, 816, 734 |

*Measured in CDCl₃ with TMS as an internal standard unless otherwise specifically indicated.

TABLE 14

| Comp'd No. | Structural formula | Property Melting point (recrystallization solvent) | NMR (δ ppm)* ( ): observation frequency | IR (cm⁻¹) ( ): measuring method |
|---|---|---|---|---|
| 53 | | Colorless oil | (270MHz) 1.89(2H, m), 2.50(2H, m), 2.67(4H, m), 3.05(2H, m), 3.18(4H, m), 3.53(2H, m), 3.61(2H, t, J=6.9Hz), 3.67(3H, s), 6.60(1H, d, J=3.0Hz), 6.64(1H, d, J=3.0Hz), 6.86(2H, m), 6.96(2H, m) | (film) 3406, 1602, 1508, 1464, 1438, 1238, 1164, 971, 929, 821 |
| 54 | | Colorless powdery crystals 148.0–151.0° C. (ethyl acetate-isopropyl ether) | (270MHz)(DMSO-d₆/TMS) 1.71(2H, m), 2.32(2H, t, J=7.2Hz), 2.50(4H, m), 2.77(2H, t, J=5.3Hz), 3.07(4H, m), 3.39~3.47(4H, m), 3.65(3H, s), 6.89~7.05(5H, m), 7.21(1H, d, J=2.6Hz), 10.69(1H, s) | (KBr) 3252, 2932, 2827, 1606, 1535, 1511, 1432, 1356, 1312, 1247, 1132, 1048, 928, 818, 786, |
| 55 | | Pale yellow plate crystals 190.5–192.0° C. (acetonitrile) | (270MHz)(DMSO-d₆/TMS) 1.70(2H, m), 2.32(2H, t, J=7.2Hz), 2.50(4H, m), 2.66(2H, m), 3.06 (4H, m), 3.45~3.49(4H, m), 7.33(1H, d, J=2.6Hz), 7.92 (1H, d, J=2.6Hz), 10.91(1H, s) | (KBr) 3121, 2947, 2825, 1607, 1534, 1514, 1479, 1434, 1310, 1276, 1243, 1234, 1172, 984, 919, 825 |

TABLE 14-continued

| Comp'd No. | Structural formula | Property Melting point (recrystallization solvent) | IR (cm⁻¹) NMR (δ ppm)* ( ): observation frequency | ( ): measuring method |
|---|---|---|---|---|
| 56 | 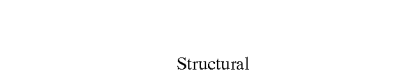 | Colorless prism crystals 185.5–187.5° C. (isopropanol) | (400MHz) 2.31(2H, m), 2.53~2.65(3H, m), 2.69~2.84(3H, m), 3.09(4H, m), 3.31(1H, m), 3.47(1H, m), 3.57 (1H, m), 3.68(3H, s), 4.03(1H, br.s), 4.22(1H, m), 4.91(1H, m), 6.57 (1H, d, J=2.9Hz), 6.63(1H, d, J=2.9Hz), 6.83(2H, m), 6.92(2H, m) | (KBr) 3282, 2812, 1582, 1512, 1430, 1358, 1233, 1141, 1060, 958, 916, 827, 732 |

*Measured in CDCDl₃ with TMS as an internal standard unless otherwise specifically indicated.

TABLE 15

| Comp'd No. | Structural formula | Property Melting point (recrystallization solvent) | IR (cm⁻¹) NMR (δ ppm)* ( ): observation frequency | ( ): measuring method |
|---|---|---|---|---|
| 57 | | Colorless powdery crystals 168.0–167.5° C. (ethyl acetate) | (400MHz) 1.82(2H, quint, J=7.3Hz), 2.15~2.32 (3H, m), 2.44(2H, t, J=7.3Hz), 2.60 (4H, m), 3.11(4H, m), 3.34(1H, m), 3.52(1H, m), 3.59~3.70(2H, m), 3.72 (3H, s), 4.91(1H, br.s), 6.61(1H, d, J=2.9Hz), 6.70(1H, d, J=2.9Hz), 6.87 (2H, m), 6.95(2H, m) | (KBr) 3258, 2820, 1595, 1509, 1482, 1432, 1378, 1287, 1220, 1162, 1027, 952, 926, 832, 742, 674 |
| 58 | | Colorless powdery crystals 197.0–198.5° C. (ethanol) | (400MHz) 1.50~1.65(4H, m), 2.21(2H, m), 2.42 (2H, m), 2.59(4H, m), 3.10(4H, m), 3.28(1H, m), 3.47(1H, m), 3.58(1H, m), 3.71(3H, s), 4.88(1H, t, J=4.6Hz), 6.59 (1H, d, J=2.9Hz), 6.66(1H, d, J=2.9Hz), 6.82~6.91(2H, m), 6.94(2H, m) | (KBr) 3316, 1582, 1512, 1292, 1232, 1056, 949, 831, 731 |
| 59 | | Colorless needle crystals 161.0–163.0° C. (chloroform-ethyl ether) | (400MHz) 1.77(2H, quint, J=7.2Hz), 2.10(1H, m), 2.22(1H, m), 2.23(3H, s), 2.42(2H, t, J=7.2Hz), 2.59(4H, m), 3.10(4H, m), 3.30(1H, dd, J=8.0Hz, 15.0Hz), 3.39~3.59(3H, m), 3.62(3H, s), 4.85(1H, t, J=5.6Hz), 6.39(1H, s), 6.85(2H, m), 6.94(2H, m) | (KBr) 3346, 2949, 1590, 1560, 1513, 1480, 1442, 1305, 1245, 1165, 1053, 817 |
| 60 | | Colorless powdery crystals 146.0–147.0° C. (chloroform-hexane) | (400MHz) 1.43(3H, t, J=7.3Hz), 1.83(2H, quint, J=7.3Hz), 2.23(2H, m), 2.45(2H, t, J=7.3Hz), 2.60(4H, m), 3.11(4H, m), 3.34(1H, m), 3.52~3.71(3H, m), 3.98~4.16(2H, m), 4.93(1H, t, J=4.4Hz), 6.70(1H, d, J=3.0Hz), 6.75 (1H, d, J=3.0Hz), 6.86(2H, m) | (KBr) 3298, 2944, 2825, 1583, 1512, 1448, 1245, 1158, 1056, 818 |

*Measured in CDCl₃ with TMS as an internal standard unless otherwise specifically indicated.

TABLE 16

| Comp'd No. | Structural formula | Property Melting point (recrystallization solvent) | NMR (δ ppm)* ( ): observation frequency | IR (cm⁻¹) ( ): measuring method |
|---|---|---|---|---|
| 61 | (structure with pyrrole fused azepinone, N-Ph, OH, (CH₂)₃-piperazine-4-fluorophenyl) | Colorless flaky crystals 190.5–192.0° C. (chloroform-diethyl ether) | (400MHz) 1.86(2H, m), 2.18(2H, m), 2.48(2H, m), 2.61(4H, m), 3.11(4H, m), 3.37(1H, m), 3.63(2H, t, J=7.2Hz), 3.78(1H, m), 4.88(1H, t, J=4.1Hz), 6.78(1H, d, J=3.0Hz), 6.83~6.90(3H, m), 6.95(2H, m), 7.39~7.53(5H, m) | (KBr) 3111, 2829, 1610, 1509, 1432, 1302, 1236, 1174, 1124, 1060, 907, 826, 766, 696 |
| 62 | (structure with N-Bzl, OH, (CH₂)₃-piperazine-4-fluorophenyl) | Pale yellow oil | (400MHz) 1.82(2H, m), 2.15(2H, m), 2.45(2H, m), 2.60(4H, m), 3.11(4H, m), 3.31(1H, m), 3.53(1H, m), 3.58~3.73(3H, m), 4.76 (1H, t, J=4.3H), 5.15(1H, d, J=16.1Hz), 5.43(1H, d, J=16.1Hz), 6.69(1H, d, J=2.9Hz), 6.78(1H, d, J=2.9Hz), 6.86(2H, m), 6.95(2H, m), 7.04(2H, m), 7.25~7.35(3H, m) | (KBr) 3310, 2944, 2821, 1590, 1540, 1508, 1456, 1369, 1235, 1163, 1054, 956, 920, 816, 731, 700 |
| 63 | (structure with HO, N-Me pyrrole, (CH₂)₃-piperazine-4-fluorophenyl) | Colorless oil | (270MHz) 1.84(2H, quint, J=7.3Hz), 2.06~2.26 (3H, m), 2.46(2H, m), 2.61(4H, m), 3.12(4H, m), 3.33(1H, m), 3.57(2H, t, J=7.3Hz), 3.59(1H, m), 3.63(3H, s), 4.94(1H, t, J=5.3Hz), 6.64(1H, d, J=2.6Hz), 6.83~6.98(4H, m), 7.22(1H, d, J=2.6Hz) | (film) 3500–3200, 2946, 2824, 1592, 1538, 1505, 1455, 1378, 1235, 1163, 1054, 925, 818, 751 |
| 64 | (structure with N-Me, OH, (CH₂)₃-piperazine-phenyl) | Colorless powdery crystals 167.5–170.0° C. (isopropanol-isopropyl ether) | (400MHz) 1.81(2H, quint, J=7.3Hz), 2.22(2H, m), 2.44(2H, m), 2.61(4H, m), 3.20(4H, m), 3.33(1H, m), 3.48(1H, m), 3.63(2H, m), 3.72(3H, s), 4.89(1H, t, J=4.3Hz), 6.59(1H, d, J=2.9Hz), 6.64(1H, d, J=2.9Hz), 6.84(1H, d, J=7.3Hz), 6.91(2H, d, J=8.1Hz), 7.25(2H, m) | (KBr) 3278, 2813, 1598, 1508, 1430, 1236, 920, 759, 741, 692 |

*Measured in CDCl₃ with TMS as an internal standard unless otherwise specifically infected.

TABLE 17

| Comp'd No. | Structural formula | Property Melting point (recrystallization solvent) | NMR (δ ppm)* ( ): observation frequency | IR (cm⁻¹) ( ): measuring method |
|---|---|---|---|---|
| 65 | (structure with N-Me, OH, (CH₂)₃-piperazine-3-fluorophenyl) | Colorless prism crystals 163.5–168.5° C. (ethyl acetate-hexane) | (400MHz) 1.80(2H, m), 2.22(2H, m), 2.43(2H, m), 2.58(4H, m), 3.19(4H, m), 3.32(1H, m), 3.48(1H, m), 3.57~3.69(2H, m), 3.72 (3H, s), 4.89(1H, t, J=4.4Hz), 6.51 (1H, dt, J=1.9Hz, 8.2Hz), 6.57(1H, m), 6.60(1H, d, J=2.9Hz), 6.66(1H, m), 6.68(1H, d, J=2.9Hz), 7.17(1H, m) | (KBr) 3273, 2837, 1596, 1509, 1495, 1430, 1263, 1182, 996, 973, 759, 740, 684 |

TABLE 17-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 66 | | Colorless powdery crystals 138.0–140.0° C. (ethyl acetate) | (400MHz) 1.82(2H, quint, J=7.3Hz), 2.23 (2H, m), 2.46(2H, m), 2.63(4H, m), 3.11 (4H, m), 3.34(1H, m), 3.52(1H, m), 3.59~3.70(2H, m), 3.72(3H, s), 4.90(1H, t, J=4.5Hz), 6.61(1H, d, J=2.9Hz), 6.70 (1H, d, J=2.9Hz), 6.88~7.08(4H, m) | (KBr) 3312, 2948, 2818, 1587, 1540, 1501, 1447, 1302, 1259, 1238, 1142, 1053, 984, 758 |
| 67 | | Colorless oil | (270MHz) 1.83(2H, quint, J=7.3Hz), 2.21(2H, m), 2.44(2H, t, J=7.3Hz), 2.60(4H, m), 3.07(4H, m), 3.34(1H, m), 3.57~371 (3H, m), 3.72(3H, s), 4.91(1H, m), 6.63 (1H, d, J=2.6Hz), 6.72(1H, d, J=2.6Hz), 6.75~6.84(4H, m) | (film) 3250, 2947, 2822, 1585, 1513, 1445, 1364, 1259, 1049, 956, 817, 730 |
| 68 | | Colorless powdery crystals 181.0–183.0° C. (chloroform-ethyl acetate) | (400MHz) 1.80(2H, m), 2.22(2H, m), 2.43(2H, m), 2.59(4H, m), 3.15(4H, m), 3.33(1H, m), 3.50(1H, m), 3.56~3.69(2H, m), 3.72 (3H, s), 4.89(1H, m), 6.61(1H, d, J=2.9Hz), 6.69(1H, d, J=2.9Hz), 6.82 (2H, m), 7.19(2H, m) | (KBr) 3236, 2947, 1582, 1538, 1500, 1249, 1140, 1051, 954, 810, 742 |

*Measured in CDCl$_3$ with TMS as an internal standard unless otherwise specifically indicated.

TABLE 18

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 69 | | Orange prism crystals 177.0–178.5° C. (chloroform-isopropyl ether) | (400MHz) 1.81(2H, quint, J=7.3Hz), 2.13~ 2.31(3H, m), 2.45(2H, m), 2.59(4H, m), 3.33(1H, m), 3.41(4H, m), 3.50~3.71 (3H, m), 3.72(3H, s), 4.91(1H, br.s), 6.62(1H, d, J=2.9Hz), 6.70(1H, d, J=2.9Hz), 6.81(2H, m), 8.11(2H, m) | (KBr) 3299, 2922, 1599, 1509, 1483, 1320, 1240, 1103, 1090, 1021, 951, 824, 753, 731, 656 |
| 70 | | Pale yellow powdery crystals 155.0–158.0° C. (chloroform-isopropyl ether) | (400MHz) 1.81(2H, quint, J=7.3Hz), 2.22 (2H, m), 2.44(2H, m), 2.61(4H, m), 3.09(4H, m), 3.33(1H, m), 3.51(1H, m), 3.57~3.69(2H, m), 3.72(3H, s), 3.76 (3H, s), 4.89(1H, t, J=4.8Hz), 6.60(1H, d, J=2.9Hz), 6.60(1H, d, J=2.9Hz), 6.83(2H, m), 6.89(2H, m) | (KBr) 3304, 2947, 2821, 1597, 1513, 1441, 1288, 1244, 1042, 827, 739 |

TABLE 18-continued

| Comp'd No. | Structural formula | Property Melting point (recrystallization solvent) | IR (cm$^{-1}$) NMR (δ ppm)* ( ): observation frequency | ( ): measuring method |
|---|---|---|---|---|
| 71 | | Colorless prism crystals 169.0–172.5° C. (ethyl acetate-hexane) | (400MHz) 1.81(2H, quint, J=7.3Hz), 2.22(2H, m), 2.42(2H, m), 2.49(4H, m), 3.33(1H, m), 3.49(1H, m), 3.59~3.70(2H, m)3.72 (3H, s), 3.81(4H, m), 4.89(1H, t, J=4.4Hz), 6.46(1H, t, J=4.8Hz), 6.60(1H, d, J=2.9Hz), 6.68(1H, d, J=2.9Hz), 8.29(2H, d, J=4.8Hz) | (KBr) 3250, 2852, 1610, 1584, 1546, 1508, 1482, 1449, 1358, 1306, 1254, 1048, 985, 956, 796, 744 |
| 72 | | Colorless oil | (400MHz) 1.76(2H, m), 2.19(2H, m), 2.32~2.57 (10H, m), 3.28(1H, m), 3.47(1H, m), 3.53~3.66(2H, m), 3.71(3H, s), 4.22 (1H, s), 4.88(1H, t, J=4.5Hz), 6.59(1H, d, J=2.9Hz), 6.67(1H, d, J=2.9Hz), 7.16 (2H, t, J=7.3Hz), 7.26(4H, m), 7.40(4H, m) | (film) 3319, 2944, 2809, 1590, 1540, 1509, 1450, 1282, 1150, 1056, 1008, 956, 733, 707 |

*Measured in CDCl$_3$ with TMS as an internal standard unless otherwise specifically indicated.

TABLE 19

| Comp'd No. | Structural formula | Property Melting point (recrystallization solvent) | IR (cm$^{-1}$) NMR (δ ppm)* ( ): observation frequency | ( ): measuring method |
|---|---|---|---|---|
| 73 | | Yellow oil | (400MHz) 1.82~1.93(6H, m), 2.10~2.31(4H, m), 2.44~2.59(3H, m), 3.12(2H, d, J=11.3Hz), 3.33(1H, m), 3.46~3.69(3H, m), 3.72(3H, s), 4.90(1H, t, J=4.6Hz), 6.59(1H, d, J=2.9Hz), 6.66(1H, d, J=2.9Hz), 7.17~7.25(3H, m), 7.25~7.33(2H, m) | (film) 3312, 2924, 1591, 1540, 1511, 1482, 1440, 1364, 1256, 1052, 955, 733, 700 |
| 74 | | Colorless prism crystals 142.5–147.0° C. (chloroform-ethyl acetate) | (400MHz) 1.82(2H, m), 2.02~2.19(6H, m), 2.23 (2H, m), 2.45(2H, m), 2.98~3.15(3H, m), 3.35(1H, m), 3.50~3.71(3H, m), 3.73(3H, m), 4.91(1H, m), 6.61(1H, d, J=2.9Hz), 6.70(1H, d, J=2.9Hz), 7.04 (1H, dt, J= 2.1Hz, 8.8Hz), 7.23(1H, dd, J=2.1Hz, 8.5Hz), 7.69(1H, dd, J=5.1Hz, 8.8Hz), | (KBr) 3252, 2947, 1585, 1544, 1515, 1419, 1351, 1298, 1112, 1057, 958, 835, 730 |
| 75 | | Colorless powdery crystals 175.5–178.0° C. (decomposed) (isopropanol-isopropyl ether) | (400MHz) 1.72~1.87(6H, m), 2.07(2H, m), 2.21 (2H, m), 2.38(2H, m), 2.98(2H, m), 3.18(1H, m), 3.30(1H, m), 3.44(1H, m), 3.56(1H, m), 3.63(1H, m), 3.72 (3H, s), 4.88 (1H, t, J=4.8Hz), 6.58(1H, d, J=2.9Hz), 6.65(1H, d, J=2.9Hz), 7.13(2H, m), 7.96(2H, m) | (KBr) 1677, 1600, 1508, 1432, 1291, 1251, 1230, 1159, 972, 956, 742 |

TABLE 19-continued

| Comp'd No. | Structural formula | Property Melting point (recrystallization solvent) | IR (cm⁻¹) NMR (δ ppm)* ( ): observation frequency | ( ): measuring method |
|---|---|---|---|---|
| 76 | (structure: pyrrolo-azepinone with OMe, N-Me, linked via (CH₂)₃N-piperazine-N-(4-chlorophenyl)) | Colorless powdery crystals 132.0–135.° C. (ethyl acetate- hexane) | (400MHz) 1.84(2H, m), 1.95(1H, m), 2.40~2.51 (3H, m), 2.60(4H, m), 3.16(4H, m), 3.28(1H, m), 3.36(3H, s), 3.62(5H, m), 3.69(1H, m), 4.39(1H, t, J=3.9Hz), 6.61(1H, d, J=2.9Hz), 6.71(1H, d, J=2.9Hz), 6.82(2H, m), 7.19(2H, m) | (KBr) 2954, 2361, 1603, 1500, 1412, 1348, 1303, 1258, 1146, 1068, 812, 741 |

*Measured in CDCl₃ with TMS as an internal standard unless otherwise specifically indicated.

TABLE 20

| Comp'd No. | Structural formula | Property Melting point (recrystallization solvent) | IR (cm⁻¹) NMR (δ ppm)* ( ): observation frequency | ( ): measuring method |
|---|---|---|---|---|
| 77 | (structure: pyrrolo-azepinone with OMe, N-Me, linked via (CH₂)₃N-piperazine-N-(4-fluorophenyl)) | Pale yellow oil | (400MHz) 1.84(2H, quint, J=7.3Hz), 1.95(1H, m), 2.40~2.50(3H, m), 2.62(4H, m), 3.12 (4H, m), 3.28(1H, dd, J=8.4Hz, 14.9Hz), 3.36(3H, s), 3.58~3.65(5H, m), 3.69(1H, dd, J=9.0Hz, 14.9Hz), 4.39(1H, t, J=3.9Hz), 6.60 (1H, d, J=2.9Hz), 6.71(1H, d, J=2.9Hz), 6.82~6.90(2H, m), 6.90~6.98(2H, m) | (film) 2943, 2819, 1609, 1541, 1509, 1480, 1234, 1163, 1073, 951, 816, 748 |
| 78 | (structure: pyrrolo-azepinone with vinyl, N-Me, linked via (CH₂)₃N-piperazine-N-(4-fluorophenyl)) | Colorless plate crystals 175.5–177.0° C. (dichloromethane-hexane) | (400MHz) 1.82(2H, quint, J=7.3Hz), 2.43(2H, t, J=7.3Hz), 2.59(4H, m), 3.11(4H, m), 3.60(2H, t, J=7.3Hz), 3.61(3H, s), 3.71(2H, d, J=6.9Hz), 6.09(1H, m), 6.64~6.69(2H, m), 6.75(1H, d, J=2.9Hz), 6.86(2H, m), 6.94(2H, m) | (KBr) 2822, 1594, 1511, 1471, 1450, 1420, 1386, 1344, 1295, 1254, 1244, 1230, 1161, 1003, 927, 825, 780, 735 |
| 79 | (structure: pyrrolo-azepinone with vinyl, N-Me, linked via (CH₂)₃N-piperazine-N-(4-chlorophenyl)) | Colorless plate crystals 171.5–172.5° C. (dichloromethane-hexane) | (400MHz) 1.84(2H, m), 2.42(2H, m), 2.58(4H, m), 3.15(4H, m), 3.54~3.68(5H, m), 3.71 (2H, d, J=6.8Hz), 6.09(1H, m), 6.62~ 6.72(2H, m), 6.75(1H, d, J=2.7Hz), 6.82(2H, d, J=8.6Hz), 7.18(2H, d, J=8.6Hz), | (KBr) 1593, 1498, 1449, 1387, 1246, 1160, 924, 818, 732 |
| 80 | (structure: pyrrolo-azepinone with vinyl, N-Me, linked via (CH₂)₃N-piperidine-4-C(O)-(4-fluorophenyl)) | Pale yellow oil | (400MHz) 1.74~1.93(6H, m), 2.17(2H, m), 2.42 (2H, m), 3.00(2H, m), 3.20(1H, m), 3.52~3.63(5H, m), 3.71(2H, d, J= 6.9Hz), 6.11(1H, m), 6.60~6.69(2H, m), 6.74(1H, d, J=2.9Hz), 7.13(2H, m), 7.95(2H, m) | (film) 2945, 1677, 1597, 1498, 1470, 1427, 1262, 1229, 1157, 976, 854, 744 |

*Measured in CDCl₃ with TMS as an internal standard unless otherwise specifically indicated.

TABLE 21

| Comp'd No. | Structural formula | Property Melting point (recrystallization solvent) | NMR(δ ppm)*<br>( ): observation frequency | IR (cm$^{-1}$)<br>( ):<br>measuring method |
|---|---|---|---|---|
| 81 | (structure: pyrrolo-azepinone with (CH$_2$)$_3$-piperazine-phenyl-Cl, N-Me) | Colorless powdery crystals 133.0–134.0° C. (ethyl acetate-hexane) | (400MHz) 1.83(2H, m), 2.11(2H, m), 2.45(2H, m) 2.60(4H, m), 2.78(2H, t, J=6.9Hz), 3.16(4H, m), 3.45(2H, m), 3.49(3H, s), 3.58(2H, t, J=7.3Hz), 6.55(1H, d, J=3.0Hz), 6.68(1H, d, J=3.0Hz), 6.82 (2H, m), 7.19(2H, m) | (Kbr) 2927, 1607,1501, 1480, 1432, 1356, 1309, 1251, 1170, 1142, 948, 811, 722 |
| 82 | (structure: pyrrolo-azepinone with (CH$_2$)$_3$-piperazine-phenyl-F, N-Me) | Pale yellow oil | (400MHz), 1.83(2H, m), 2.11(2H, m), 2.46(2H, m), 2.61(4H, m), 2.78(2H, t, J=6.9Hz), 3.12 (4H, m), 3.44(2H, m), 3.49(3H, s), 3.58 (2H, t, J=7.3Hz), 6.54(1H, d, J=3.0Hz), 6.68(1H, d, J=3.0Hz), 6.82 ~ 6.90(2H, m), 6.90 ~ 6.98(2H, m) | (film) 2942, 2817, 1604, 1509, 1480, 1449, 1233, 1162,816, 719 |

*Measured in CDCl$_3$ with TMS as an internal standard unless otherwise specifically indicated.

EXAMPLE 80

Separation of 5-[3-[4-(4-fluorophenyl)piperazin-1-yl]propyl]-8-hydroxy-1-methyl-1,4,5,6,7,8-hexahydropyrrolo[3,2-c]azepin-4-one (Compound No. 57)

Into Respective Optically-Active Substances by the Use of an Optical Resolution Column (Compound No. 83 & Compound No. 84)

Twenty microliters (20 μl) of a 50 mg/ml methanol solution of Compound No. 57 were subjected to high performance liquid chromatography (hereinafter abbreviated as "HPLC") to separately collect eluate fractions [column: "CHIRALPAC AD 4.6∅×250 mm" (product of Daicel Chemical Industries, Ltd.), column temperature: 40° C., mobile phase: hexane/ethanol/methanol/diethylamine= 70/10/20/0.1, flow rate: 0.4 ml/min, detection: 240 nm]. This procedure was repeated 7 times. Eluates were separately concentrated under reduced pressure, whereby the respective optically-active substances were obtained as much as 1.2 mg each.

Compound No. 83 (colorless powdery crystals):

Obtained from the first eluate fraction (elution time: about 14 minutes)

[α]$^{20}_D$-7.27° (C=3.00, MeOH)

Compound No. 84 (colorless powdery crystals):

Obtained from the second eluate fraction (elution time: about 18 minutes)

[α]$^{20}_D$+7.30° (C=2.96, MeOH)

From an X-ray crystal structure analysis of the L-(+)-tartrate of Compound No. 83, Compound No. 83 was found to have an S-configuration at the 8-position.

EXAMPLE 81

Optical resolution of 5-[3-[4-(4-fluorophenyl) piperazin-1-yl]propyl]-8-hydroxy-1-methyl-1,4,5,6,7,8-hexahydropyrrolo[3,2-c]azepin-4-one (Compound No. 57) by an Optically Active Acid (Synthesis of Compound No. 83)

Compound No. 57 (20.0 g, 50 mmol) was dissolved under heat in 160 ml of methanol. Subsequent to cooling, 7.50 g (50 mmol) of L-(+)-tartaric acid were added. After the resultant mixture was seeded and then stirred at room temperature for 24 hours, precipitated crystals were collected by filtration. Colorless crystals were obtained as much as 11.8 g. Those crystals were dissolved under heat in 59 ml of DMF. Subsequent to cooling, 59 ml of ethanol were added. After the resultant mixture was seeded and then stirred at room temperature for 21 hours, precipitated crystals were collected so that 8.49 g of colorless crystals were obtained. Those crystals were added under stirring into a chilled 1 N aqueous solution of sodium hydroxide, followed by stirring. The reaction mixture was extracted twice with chloroform. The organic layers were washed with a saturated aqueous solution of sodium chloride, dried over anhydrous sodium sulfate, and then concentrated under reduced pressure. Colorless crystals so obtained were recrystallized twice from 2-propanol, whereby 4.75 g of colorless crystals were obtained (yield: 24%). Those crystals were analyzed by HPLC (under the same conditions as in Example 80) and were confirmed to be Compound No. 83.

EXAMPLE 82

Synthesis of (−)-(S)-5-[3-[4-(4-fluorophenyl)piperazin-1-yl]-8-hydroxy-1-methyl-1,4,5,6,7,8-hexahydropyrrolo[3,2-c]azepin-4-one (Compound No. 83) by Asymmetric Reduction of Compound No. 17 with (R)-3,3-diphenyl-1-methyltetrahydro-1H,3H-pyrrolo-[1,2-c][1,3,2]oxazaborol Compound No. 17 (1.28 g, 5 mmol) and molcular sieves 4A (powder, 1.0 g) were placed in a reactor. After the contents were dried by a vacuum pump, the reactor was purged with argon gas. Toluene (25 ml) was added to the reactor. After the contents were ice-cooled, a solution of 277 mg (1 mmol) of (R)-3,3-diphenyl-1-methyltetrahydro-1H, 3H-pyrrolo[1,2-c][1,3,2]oxazaborol in 4 ml of toluene was added dropwise, followed by the dropwise addition of a 1.11 M toluene solution of borane-dimethyl sulfide complex, (9.5 ml, 10. 5 mmol). After the reaction mixture was stirred at 3° C. for 4 hours, a saturated aqueous solution of sodium chloride was added and the resultant mixture was then filtered. Ethyl acetate was added to the filtrate. The organic layer was separated, dried over anhydrous magnesium sulfate and then concentrated under reduced pressure. The residue was purified by chromatography on a silica gel column (eluent: methylene chloride/methanol=30/1), whereby 887 mg of colorless crystals were obtained.

A suspension of 850 mg of the above-obtained crystals, 624 mg (3.47 mmol) of 1-(4-fluorophenyl)piperazine, 911 mg (6.6 mmol) of potassium carbonate and 990 mg (6.6 mmol) of potassium iodide in 16.5 ml of acetonitrile was refluxed for 6 hours. After the reaction mixture was concentrated under reduced pressure, a saturated aqueous solution of sodium hydrogencarbonate was added to the residue, followed by extraction with chloroform (twice). The organic layers were washed with a saturated aqueous solution of sodium chloride, dried over anhydrous sodium magnesium, and then concentrated under reduced pressure. The residue was purified by chromatography on a silica gel column (eluent: methylene chloride/methanol 20/1→10/1), whereby 1.01 g of crystals were obtained. The thus-obtained crystals were recrystallized twice from 2-propanol, whereby 649 mg of the title compound were obtained [optical purity: 99.0% e.e. (by HPLC analysis)].

Melting point: 167.5–168.5° C.

EXAMPLE 83
Synthesis of (−)-(S)-5-[3-[4-(4-fluorophenyl)piperazin-1-yl]-8-hydroxy-1-methyl-1,4,5,6,7,8-hexahydropyrrolo[3,2-c]azepin-4-one (Compound No. 83) by Asymmetric Reduction of Compound No. 33 with (R)-3,3-diphenyl-1-methyltetrahydro-1H, 3H-pyrrolo-[1,2-c][1,3,2]oxazaborol Compound No. 33 (884 mg, 2.22 mmol) and molcular sieves 4A (powder, 450 mg) were placed in a reactor. After the contents were dried by a vacuum pump, the reactor was purged with argon gas. Toluene (11 ml) was added to the reactor. Under ice cooling and stirring, a solution of 123 mg (0.44 mmol) of (R)-3,3-diphenyl-1-methyltetrahydro-1H, 3H-pyrrolo[1,2-c][1,3,2]oxazaborol in 2 ml of toluene and a 1.11 M toluene solution of borane-dimethyl sulfide complex (12 ml, 13.3 mmol) were added dropwise successively. After the reaction mixture was stirred at 2° C. for 6 hours, a saturated aqueous solution of sodium chloride was added and the resultant mixture was extracted with chloroform (twice). The organic layers were dried over anhydrous magnesium sulfate and then concentrated under reduced pressure. Acetonitrile (26.4 ml) and triethylamine (8.8 ml) were added to the residue. The resultant mixture was stirred at room temperature for 40 hours and then concentrated under reduced pressure. Post treatment and purification were conducted as in Example 82, whereby 355 mg of the title compound were obtained [optical purity: 99.0% e.e. (by HPLC analysis)].

EXAMPLE 84
Synthesis of (−)-(S)-5-[3-[4-(4-fluorophenyl)piperazin-1-yl]-8-hydroxy-1-methyl-1,4,5,6,7,8-hexahydropyrrolo[3,2-c]azepin-4-one (Compound No. 83) by Asymmetric Hydrogen Transfer Reaction of Compound No. 17 with a Ruthenium Complex A suspension of 58 mg (0.1 mmol) of di-µ-chlorobis[η-mesitylene]chlororuthenium, 73 mg (0.2 mmol) of (1S,2S)-N-(p-tolylsulfonyl)-1,2-dipheny-lethylenediamine and 40 mg (0.4 mmol) of triethylamine in 50 ml of 2-propanol was stirred at 80° C. for 1 hour. The reaction mixture was concentrated under reduced pressure at 60° C. and dried, whereby the ruthenium complex was prepared.

Into a solution of 1.28 g (5 mmol) of Compound 17 and 2.5 ml of a formic acid-triethylamine azeotropic mixture (5:2 molar ratio) in 8 ml of THF, 33 mg (0.05 mmol) of the above-obtained ruthenium complex were added, followed by stirring at room temperature for 72 hours. Ethyl acetate was added to the reaction mixture. The resultant mixture was washed with a half-saturated aqueous solution of sodium chloride, dried over anhydrous magnesium sulfate and then concentrated under reduced pressure. The residue was purified by chromatography on a silica gel column (eluent: methylene chloride/methanol=30/1), whereby 249 mg of pale brown crystals were obtained.

Using 240 mg of the above-obtained crystals, 184 mg (1.02 mmol) of 1-(4-fluorophenyl)piperazine, 257 mg (1.86 mmol) of potassium carbonate, 279 mg (1.86 mmol) of potassium iodide and 5 ml of acetonitrile, a reaction, post treatment and purification were conducted as in Example 82, whereby 170 mg of the title compound were obtained [optical purity: 99.6% e.e. (by HPLC analysis)].

EXAMPLE 85
Synthesis of (−)-(S)-5-[3-[4-(4-fluorophenyl)piperazin-1-yl]-8-hydroxy-1-methyl-1,4,5,6,7,8-hexahydropyrrolo[3,2-c]azepin-4-one (Compound No. 83) by an Asymmetric Hydrogen Transfer Reaction of Compound No. 33 with a Ruthenium Complex Into a solution of 955 mg (2.4 mmol) of Compound No. 33 and 1.2 ml of a formic acid-triethylamine azeotropic mixture (5:2 molar ratio) in 3.8 ml of THF, 16 mg (0.024 mmol) of the ruthenium complex obtained in Example 84 were added, followed by stirring at room temperature for 90 hours. Post treatment and purification were conducted as in Example 82, whereby 160 mg of the title compound were obtained [optical purity: 98.0% e.e. (by HPLC analysis)].

EXAMPLE 86
Synthesis of (+)-(R)-5-[3-[4-(4-fluorophenyl)piperazin-1-yl]-8-hydroxy-1-methyl-1,4,5,6,7,8-hexahydropyrrolo[3,2-c]azepin-4-one (Compound No. 84) by Asymmetric Reduction of Compound No. 33 with (S)-3,3-diphenyl-1-methyltetrahydro-1H,3H-pyrrolo[1,2-c][1,3,2]oxazaborol Using 398 mg (1.0 mmol) of Compound No. 33, 250 mg of molcular sieves 4A (powder), 56 mg (0.2 mmol) of (S)-3,3-diphenyl-1-methyltetrahydro-1H,3H-pyrrolo[1,2-c][1,3,2]oxazaborol, 4.1ml (4.5 mmol) of a 1.10 M toluene solution of borane-dimethyl sulfide complex and 5.4 ml of toluene, 90 mg of the title compound were obtained in a similar manner as in Example 83 [optical purity: 98.6% e.e. (by HPLC analysis)].

Melting point: 167.5–168.5° C.

EXAMPLE 87
Synthesis of (+)-5-[3-[4-(4-fluorophenyl)piperazin-1-yl]-8-hydroxy-1-methyl-1,4,5,6,7,8-hexahydropyrrolo[3,2-c]azepin-4-one (Compound No. 84) by an Asymmetric Hydrogen Transfer Reaction of Compound No. 33 with a Ruthenium Complex Using 1.59 g (4 mmol) of Compound No. 33, a solution of 2 ml of a formic acid-triethylamine azeotropic mixture (5:2 molar ratio) in 6.4 ml of THF, and 27 mg (0.04 mmol) of a ruthenium complex [which had been prepared in a similar manner as in Example 84 except for the use of (1R,2R)-N-(p-tolylsulfonyl)-1,2-diphenylethylenediamine in place of (1S,2S)-N-(p-tolylsulfonyl)-1,2-diphenylethylenediamine], 161 mg of the title compound were obtained in a similar manner as in Example 85 [optical purity: 99.7% e.e. (by HPLC analysis)].

EXAMPLE 88

In the same manner or a similar manner as in any of Examples 1–87 described above, the following compounds represented by the formula (I-1) are obtained.

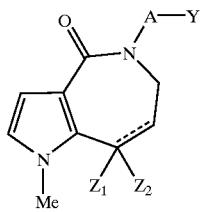

(I-1)

wherein the dashed line, A, Y, $Z_1$ and $Z_2$ have the same meanings as defined above.

(1) 5-[3-[4-(4-Hydroxyphenyl)piperazin-1-yl]propyl]-1-methyl-1,4,5,6,7,8-hexahydropyrrolo[3,2-c]azepin-4-one-8-spiro-2'-(1',3'-dithiolane)
(2) 5-[3-[4-(4-Fluorobenzoyl)piperidino]propyl]-1-methyl-1,4,5,6,7,8-hexahydropyrrolo[3,2-c]azepin-4-one-8-spiro-2'-(1',3'-dithiolane)
(3) 1-Methyl-5-[3-(4-phenylpiperazin-1-yl)propyl]-1,4,5,6,7,8-hexahydropyrrolo[3,2-c]azepin-4-one-8-spiro-2'-(1',3'-dithiolane)
(4) 5-[3-[4-(4-Chlorophenyl)piperazin-1-yl]propyl]-1-methyl-1,4,5,6,7,8-hexahydropyrrolo[3,2-c]azepin-4-one-8-spiro-2-(1',3'-dithiolane)
(5) 5-[3-[4-(4-Fluorophenyl)piperazin-1-yl]propyl]-1-methyl-1,4,5,6,7,8-hexahydropyrrolo[3,2-c]azepin-4-one-8-spiro-2'-(1',3'-dithiane)
(6) 5-[3-[4-(4-Hydroxyphenyl)piperazin-1-yl]propyl]-1-methyl-1,4,5,6,7,8-hexahydropyrrolo[3,2-c]azepin-4-one-8-spiro-2'-(1',3'-dithiane)
(7) 1-Methyl-5-[3-(4-phenylpiperazin-1-yl)propyl]-1,4,5,6,7,8-hexahydropyrrolo[3,2-c]azepin-4-one-8-spiro-2'-(1',3'-dithiane)
(8) 5-[3-[4-(4-Chlorophenyl)piperazin-1-yl]propyl]-1-methyl-1,4,5,6,7,8-hexahydropyrrolo[3,2-c]azepin-4-one-8-spiro-2'-(1',3'-dithiane)
(9) 8,8-Bis(ethylthio)-5-[3-[4-(4-fluorophenyl)piperazin-1-yl]propyl]-1-methyl-1,4,5,6,7,8-hexahydropyrrolo[3,2-c]azepin-4-one
(10) 8,8-Bis(ethylthio)-5-[3-[4-(4-hydroxyphenyl)piperazin-1-yl]propyl]-1-methyl-1,4,5,6,7,8-hexahydropyrrolo[3,2-c]azepin-4-one
(11) 8,8-Bis(ethylthio)-1-methyl-5-[3-(4-phenylpiperazin-1-yl)propyl]-1,4,5,6,7,8-hexahydropyrrolo[3,2-c]azepin-4-one
(12) 5-[3-[4-(4-Chlorophenyl)piperazin-1-yl]propyl]-8,8-bis(ethylthio)-1-methyl-1,4,5,6,7,8-hexahydropyrrolo[3,2-c]azepin-4-one
(13) 8-Hydroxyimino-5-[3-[4-(4-hydroxyphenyl)piperazin-1-yl]propyl]-1-methyl-1,4,5,6,7,8-hexahydropyrrolo[3,2-c]azepin-4-one
(14) 5-[3-[4-(4-Fluorobenzoyl)piperidino]propyl]-8-hydroxyimino-1-methyl-1,4,5,6,7,8-hexahydropyrrolo[3,2-c]azepin-4-one
(15) 8-Hydroxyimino-1-methyl-5-[3-(4-phenylpiperazin-1-yl]propyl]-1,4,5,6,7,8-hexahydropyrrolo-[3,2-c)azepin-4-one
(16) 5-[3-[4-(4-Chlorophenyl)piperazin-1-yl]propyl]-8-hydroxyimino-1-methyl-1,4,5,6,7,8-hexahydropyrrolo[3,2-c]azepin-4-one
(17) 8-Hydroxy-5-[3-[4-(2-methoxyphenyl)piperazin-1-yl]propyl]-1-methyl-1,4,5,6,7,8-hexahydropyrrolo[3,2-c]azepin-4-one
(18) 5-[3-[4-(3-Chlorophenyl)piperazin-1-yl]propyl]-8-hydroxy-1-methyl-1, 4,5,6,7,8-hexahydropyrrolo-[3,2-c]azepin-4-one
(19) 5-[3-[4-(4-Hydroxyphenyl)piperazin-1-yl]propyl]-8-methoxy-1-methyl-1,4,5,6,7,8-hexahydropyrrolo-[3,2-c]azepin-4-one
(20) 5-[3-[4-(4-Fluorobenzoyl)piperidino]propyl]-8-methoxy-1-methyl-1,4,5,6,7,8-hexahydropyrrolo-[3,2-c]azepin-4-one
(21) 5-[3-[4-(3-Fluorophenyl)piperazin-1-yl]propyl]-8-methoxy-1-methyl-1,4,5,6,7,8-hexahydropyrrolo-[3,2-c]azepin-4-one
(22) 5-[2-[4-(4-Fluorophenyl)piperazin-1-yl]ethyl]-8-methoxy-1-methyl-1,4,5,6,7,8-hexahydropyrrolo-[3,2-c]azepin-4-one
(23) 5-[4-[4-(4-Fluorophenyl)piperazin-1-yl]butyl]-8-methoxy-1-methyl-1,4,5,6,7,8-hexahydropyrrolo-[3,2-c]azepin-4-one
(24) 8-Methoxy-1-methyl-5-[3-(4-phenylpiperazin-1-yl)propyl]-1,4,5,6,7,8-hexahydropyrrolo[3,2-c]azepin-4-one
(25) 8-Methoxy-5-[3-[4-(4-methoxyphenyl)piperazin-1-yl]propyl]-1-methyl-,4,5,6,7,8-hexahydropyrrolo[3,2-c]azepin-4-one
(26) 8-Methoxy-1-methyl-5-[3-[4-(2-pyrimidinyl)piperazin-1-yl]propyl]-1,4,5,6,7,8-hexahydropyrrolo[3,2-c]azepin-4-one
(27) 8-Methoxy-5-[3-[4-(2-methoxyphenyl)piperazin-1-yl]propyl]-1-methyl-1,4,5,6,7,8-hexahydropyrrolo[3,2-c]azepin-4-one
(28) 5-[3-[4-(3-Chlorophenyl)piperazin-1-yl]propyl]-8-methoxy-1-methyl-1,4,5,6,7,8-hexahydropyrrolo-[3,2-c]azepin-4-one
(29) 5-[3-[4-(6-Fluoro-1,2-benzisoxazol-3-yl)piperidino]propyl]-8-methoxy-1-methyl-1,4,5,6,7,8-hexahydropyrrolo[3,2-c]azepin-4-one
(30) 8-Ethoxy-5-[3-[4-(4-fluorophenyl)piperazin-1-yl]propyl]-1-methyl-1,4,5,6,7,8-hexahydropyrrolo[3,2-c]azepin-4-one
(31) 8-Ethoxy-5-[3-[4-(4-hydroxyphenyl)piperazin-1-yl]propyl]-1-methyl-1,4,5,6,7,8-hexahydropyrrolo[3,2-c]azepin-4-one
(32) 8-Ethoxy-1-methyl-5-[3-(4-phenylpiperazin-1-yl)propyl]-1,4,5,6,7,8-hexahydropyrrolo[3,2-c]azepin-4-one
(33) 5-[3-[4-(4-Chlorophenyl)piperazin-1-yl]propyl]-8-ethoxy-1-methyl-1,4,5,6,7,8-hexahydropyrrolo-[3,2-c]azepin-4-one
(34) 8-Benzyloxy-5-[3-[4-(4-fluorophenyl)piperazin-1-yl]propyl]-1-methyl-1,4,5,6,7,8-hexahydropyrrolo[3,2-c]azepin-4-one
(35) 8-Benzyloxy-5-[3-[4-(4-hydroxyphenyl)piperazin-1-yl]propyl]-1-methyl-1,4,5,6,7,8-hexahydropyrrolo[3,2-c]azepin-4-one

(36) 8-Benzyloxy-1-methyl-5-[3-(4-phenylpiperazin-1-yl]propyl]-1,4,5,6,7,8-hexahydropyrrolo[3,2-c]azepin-4-one

(37) 8-Benzyloxy-5-[3-[4-(4-chlorophenyl)piperazin-1-yl]propyl]-1-methyl-1,4,5,6,7,8-hexahydropyrrolo[3,2-c]azepin-4-one

(38) 5-[3-[4-(4-Hydroxyphenyl)piperazin-1-yl]propyl]-1-methyl-1,4,5,6-tetrahydropyrrolo[3,2-c]azepin-4-one

(39) 5-[3-[4-(3-Fluorophenyl)piperazin-1-yl]propyl]-1-methyl-1,4,5,6-tetrahydropyrrolo[3,2-c]azepin-4-one

(40) 5-[2-[4-(4-Fluorophenyl)piperazin-1-yl]ethyl]-1-methyl-1,4,5,6-tetrahydropyrrolo[3,2-c]azepin-4-one

(41) 5-[4-[4-(4-Fluorophenyl)piperazin-1-yl]butyl]-1-methyl-1,4,5,6-tetrahydropyrrolo[3,2-c]azepin-4-one

(42) 1-Methyl-5-[3-(4-phenylpiperazin-1-yl)propyl]-1,4,5,6-tetrahydropyrrolo[3,2-c]azepin-4-one

(43) 5-[3-[4-(4-Methoxyphenyl)piperazin-1-yl]propyl]-1-methyl-1,4,5,6-tetrahydropyrrolo[3,2-c]azepin-4-one

(44) 1-Methyl-5-[3-[4-(2-pyrimidinyl)piperazin-1-yl)propyl]-1,4,5,6-tetrahydropyrrolo[3,2-c]azepin-4-one

(45) 5-[3-[4-(2-Methoxyphenyl)piperazin-1-yl]propyl]-1-methyl-1,4,5,6-tetrahydropyrrolo[3,2-c]azepin-4-one

(46) 5-[3-[4-(3-Chlorophenyl)piperazin-1-yl]propyl]-1-methyl-1,4,5,6-tetrahydropyrrolo[3,2-c]azepin-4-one

(47) 5-[3-[4-(6-Fluoro-1,2-benzisoxazol-3-yl)piperidino]propyl]-1-methyl-1,4,5,6-tetrahydropyrrolo[3,2-c]azepin-4-one

(48) 5-[3-[4-(4-Hydroxyphenyl)piperazin-1-yl]propyl]-1-methyl-1,4,5,6,7,8-hexahydropyrrolo[3,2-c]azepin-4-one

(49) 5-[3-[4-(4-Fluorobenzoyl)piperidino]propyl]-1-methyl-1,4,5,6,7,8-hexahydropyrrolo[3,2-c]azepin-4-one

(50) 5-[3-[4-(3-Fluorophenyl)piperazin-1-yl]propyl]-1-methyl-1,4,5,6,7,8-hexahydropyrrolo[3,2-c]azepin-4-one

(51) 5-[2-[4-(4-Fluorophenyl)piperazin-1-yl]ethyl]-1-methyl-1,4,5,6,7,8-hexahydropyrrolo[3,2-c]azepin-4-one

(52) 5-[4-[4-(4-Fluorophenyl)piperazin-1-yl]butyl]-1-methyl-1,4,5,6,7,8-hexahydropyrrolo[3,2-c]azepin-4-one

(53) 1-Methyl-5-[3-(4-phenylpiperazin-1-yl)propyl]-1,4,5,6,7,8-hexahydropyrrolo[3,2-c]azepin-4-one

(54) 5-[3-[4-(4-Methoxyphenyl)piperazin-1-yl]propyl]-1-methyl-1,4,5,6,7,8-hexahydropyrrolo[3,2-c]azepin-4-one

(55) 1-Methyl-5-[3-[4-(2-pyrimidinyl)piperazin-1-yl)propyl]-1,4,5,6,7,8-hexahydropyrrolo[3,2-c]azepin-4-one

(56) 5-[3-[4-(2-Methoxyphenyl)piperazin-1-yl]propyl]-1-methyl-1,4,5,6,7,8-hexahydropyrrolo[3,2-c]azepin-4-one

(57) 5-[3-[4-(3-Chlorophenyl)piperazin-1-yl]propyl]-1-methyl-1,4,5,6,7,8-hexahydropyrrolo[3,2-c]azepin-4-one

(58) 5-[3-[4-(6-Fluoro-1,2-benzisoxazol-3-yl)piperidino]propyl]-1-methyl-1,4,5,6,7,8-hexahydropyrrolo[3,2-c]azepin-4-one

EXAMPLE 89

In the same manner or a similar manner as in any of Examples 1–87 described above, the following compounds represented by the formula (I-2) are obtained.

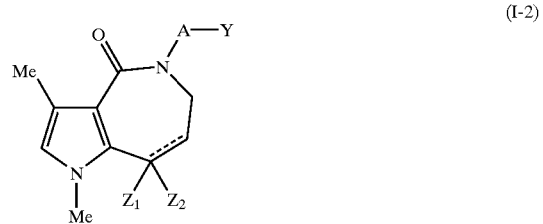

(I-2)

wherein the dashed line, A, Y, $Z_1$ and $Z_2$ have the same meanings as defined above.

(59) 5-[3-[4-(4-Fluorophenyl)piperazin-1-yl]propyl]-1,3-dimethyl-1,4,5,6,7,8-hexahydropyrrolo-[3,2-c]azepin-4-one-8-spiro-2'-(1',3'-dithiane)

(60) 8,8-Bis(ethylthio)-5-[3-[4-(6-fluoro-1,2-benzisoxazol-3-yl)piperidino]propyl]-1,3-dimethyl-1,4,5,6,7,8-hexahydropyrrolo[3,2-c]azepin-4-one

(61) 8-Hydroxy-5-[3-[4-(4-hydroxyphenyl)piperazin-1-yl]propyl]-1,3-dimethyl-1,4,5,6,7,8-hexahydropyrrolo[3,2-c]azepin-4-one

(62) 8-Hydroxy-1,3-dimethyl-5-[3-(4-phenylpiperazin-1-yl)propyl]-1,4,5,6,7,8-hexahydropyrrolo-[3,2-c]azepin-4-one

(63) 5-[3-[4-(4-Chlorophenyl)piperazin-1-yl]propyl]-8-hydroxy-1,3-dimethyl-1,4,5,6,7,8-hexahydropyrrolo[3,2-c]azepin-4-one

(64) 5-[3-[4-(6-Fluoro-1,2-benzisoxazol-3-yl)piperidino]propyl]-8-hydroxy-1,3-dimethyl-1,4,5,6,7,8-hexahydropyrrolo[3,2-c]azepin-4-one

(65) 5-[3-[4-(4-Fluorophenyl)piperazin-1-yl]propyl]-8-methoxy-1,3-dimethyl-1,4,5,6,7,8-hexahydropyrrolo[3,2-c]azepin-4-one

(66) 5-[3-[4-(4-Hydroxyphenyl)piperazin-1-yl]propyl]-8-methoxy-1,3-dimethyl-1,4,5,6,7,8-hexahydropyrrolo[3,2-c]azepin-4-one

(67) 5-[4-[4-(4-Fluorophenyl) piperazin-1-yl]butyl]-8-methoxy-1,3-dimethyl-1,4,5,6,7,8-hexahydropyrrolo[3,2-c]azepin-4-one

(68) 8-Methoxy-5-[3-[4-(2-methoxyphenyl) piperazin-1-yl]propyl]-1,3-dimethyl-1,4,5,6,7,8-hexahydropyrrolo[3,2-c]azepin-4-one

(69) 5-[3-[4-(6-Fluoro-1,2-benzisoxazol-3-yl)piperidino]propyl]-8-methoxy-1,3-dimethyl-1,4,5,6,7,8-hexahydropyrrolo[3,2-c]azepin-4-one

(70) 8-Ethoxy-5-[3-[4-(4-fluorophenyl)piperazin-1-yl]propyl]-1,3-dimethyl-1,4,5,6,7,8-hexahydropyrrolo[3,2-c]azepin-4-one

(71) 8-Benzyloxy-5-[3-[4-(4-fluorophenyl)piperazin-1-yl]propyl]-1,3-dimethyl-1,4,5,6,7,8-hexahydropyrrolo[3,2-c]azepin-4-one

(72) 5-[3-[4-(4-Fluorophenyl)piperazin-1-yl]propyl]-1,3-dimethyl-1,4,5,6-tetrahydropyrrolo[3,2-c]azepin-4-one

(73) 5-[3-[4-(4-Hydroxyphenyl)piperazin-1-yl]propyl]-1,3-dimethyl-1,4,5,6-tetrahydropyrrolo[3,2-c]azepin-4-one

(74) 1,3-Dimethyl-5-[3-(4-phenylpiperazin-1-yl)propyl]-1,4,5,6-tetrahydropyrrolo[3,2-c]azepin-4-one

(75) 5-[3-[4-(2-Methoxyphenyl)piperazin-1-yl]propyl]-1,3-dimethyl-1,4,5,6-tetrahydropyrrolo[3,2-c]azepin-4-one

(76) 5-[3-[4-(4-Chlorophenyl)piperazin-1-yl]propyl]-1,3-dimethyl-1,4,5,6-tetrahydropyrrolo[3,2-c]azepin-4-one

(77) 5-[3-[4-(6-Fluoro-1,2-benzisoxazol-3-yl)piperidino]propyl]-1,3-dimethyl-1,4,5,6-tetrahydropyrrolo[3,2-c]azepin-4-one

(78) 5-[3-[4-(4-Fluorophenyl)piperazin-1-yl]propyl]-1,3-dimethyl-1,4,5,6,7,8-hexahydropyrrolo-[3,2-c]azepin-4-one

(79) 5-[3-[4-(4-Hydroxyphenyl)piperazin-1-yl]propyl]-1,3-dimethyl-1,4,5,6,7,8-hexahydropyrrolo-[3,2-c]azepin-4-one

(80) 5-[4-[4-(4-Fluorophenyl)piperazin-1-yl]butyl]-1,3-dimethyl-1,4,5,6,7,8-hexahydropyrrolo-[3,2-c]azepin-4-one

(81) 1,3-Dimethyl-5-[3-(4-phenylpiperazin-1-yl)propyl]-1,4,5,6,7,8-hexahydropyrrolo[3,2-c]azepin-4-one

(82) 5-[3-[4-(2-Methoxyphenyl)piperazin-1-yl]propyl]-1,3-dimethyl-1,4,5,6,7,8-hexahydropyrrolo-[3,2-c]azepin-4-one

(83) 5-[3-[4-(4-Chlorophenyl)piperazin-1-yl]propyl]-1,3-dimethyl-1,4,5,6,7,8-hexahydropyrrolo-[3,2-c]azepin-4-one

(84) 5-[3-[4-(6-Fluoro-1,2-benzisoxazol-3-yl)-piperidino]propyl]-1,3-dimethyl-1,4,5,6,7,8-hexahydropyrrolo[3,2-c]azepin-4-one

EXAMPLE 90

In the same manner or a similar manner as in any of Examples 1–87 described above, the following compounds represented by the formula (I-3) are obtained.

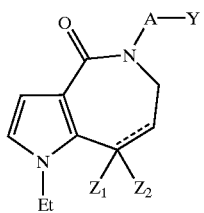

(I-3)

wherein the dashed line, A, Y, $Z_1$ and $Z_2$ have the same meanings as defined above.

(85) 5-[3-[4-(4-Chlorophenyl)piperazin-1-yl]propyl]-1-ethyl-1,4,5,6,7,8-hexahydropyrrolo[3,2-c]azepin-4-one-8-spiro-2'-(1',3'-dithiolane)

(86) 1-Ethyl-8,8-bis(ethylthio)-5-[3-[4-(4-fluorophenyl)piperazin-1-yl]propyl]-1,4,5,6,7,8-hexahydropyrrolo[3,2-c]azepin-4-one

(87) 1-Ethyl-8-hydroxy-5-[3-[4-(4-hydroxyphenyl)piperazin-1-yl]propyl]-1,4,5,6,7,8-hexahydropyrrolo[3,2-c]azepin-4-one

(88) 1-Ethyl-8-hydroxy-5-[3-(4-phenylpiperazin-1-yl)propyl]-1,4,5,6,7,8-hexahydropyrrolo[3,2-c]azepin-4-one

(89) 5-[3-[4-(4-Chlorophenyl)piperazin-1-yl]propyl]-1-ethyl-8-hydroxy-1,4,5,6,7,8-hexahydropyrrolo-[3,2-c]azepin-4-one

(90) 1-Ethyl-5-[3-[4-(6-fluoro-1,2-benzoisoxazol-3-yl)piperidino]propyl]-8-hydroxy-1,4,5,6,7,8-hexahydropyrrolo[3,2-c]azepin-4-one

(91) 1-Ethyl-5-[3-[4-(4-fluorophenyl)piperazin-1-yl]propyl]-8-methoxy-1,4,5,6,7,8-hexahydropyrrolo[3,2-c]azepin-4-one

(92) 1-Ethyl-5-[3-[4-(4-hydroxyphenyl)piperazin-1-yl]propyl]-8-methoxy-1,4,5,6,7,8-hexahydropyrrolo[3,2-c]azepin-4-one

(93) 1-Ethyl-8-methoxy-5-[3-(4-phenylpiperazin-1-yl)propyl]-1,4,5,6,7,8-hexahydropyrrolo[3,2-c]azepin-4-one

(94) 5-[3-[4-(4-Chlorophenyl)piperazin-1-yl]propyl]-1-ethyl-8-methoxy-1,4,5,6,7,8-hexahydropyrrolo-[3,2-c]azepin-4-one

(95) 1-Ethyl-5-[3-[4-(6-fluoro-1,2-benzisoxazol-3-yl)piperidino]propyl]-8-methoxy-1,4,5,6,7,8-hexahydropyrrolo[3,2-c]azepin-4-one

(96) 1-Ethyl-5-[3-[4-(4-fluorophenyl)piperazin-1-yl]propyl]-1,4,5,6-tetrahydropyrrolo[3,2-c]azepin-4-one

(97) 1-Ethyl-5-[3-[4-(4-hydroxyphenyl)piperazin-1-yl]propyl]-1,4,5,6-tetrahydropyrrolo[3,2-c]azepin-4-one

(98) 1-Ethyl-5-[3-(4-phenylpiperazin-1-yl)propyl]-1,4,5,6-tetrahydropyrrolo[3,2-c]azepin-4-one

(99) 5-[3-[4-(4-Chlorophenyl)piperazin-1-yl]propyl]-1-ethyl-1,4,5,6-tetrahydropyrrolo[3,2-c]azepin-4-one (100) 1-Ethyl-5-[3-[4-(6-fluoro-1,2-benzisoxazol-3-yl)piperidino]propyl]-1,4,5, 6-tetrahydropyrrolo-[3,2-c]azepin-4-one (101) 1-Ethyl-5-[3-[4-(4-fluorophenyl)piperazin-1-yl]propyl]-1,4,5,6,7,8-hexahydropyrrolo[3,2-c]azepin-4-one (102) 1-Ethyl-5-[3-[4-(4-hydroxyphenyl)piperazin-1-yl]propyl]-1,4,5,6,7,8-hexahydropyrrolo[3,2-c]azepin-4-one (103) 1-Ethyl-5-[3-(4-phenylpiperazin-1-yl)propyl]-1,4,5,6,7,8-hexahydropyrrolo[3,2-c]azepin-4-one (104) 1-Ethyl-5-[3-[4-(2-methoxyphenyl)piperazin-1-yl]propyl]-1,4,5,6,7,8-hexahydropyrrolo[3,2-c]azepin-4-one (105) 1-Ethyl-5-[3-[4-(4-chlorophenyl)piperazin-1-yl]propyl]-1,4,5,6,7,8-hexahydropyrrolo[3,2-c]azepin-4-one (106) 1-Ethyl-5-[3-[4-(6-fluoro-1,2-benzisoxazol-3-yl)piperidino]propyl]-1,4,5,6,7,8-hexahydropyrrolo[3,2-c]azepin-4-one

EXAMPLE 91

In the same manner or a similar manner as in any of Examples 1–87 described above, the following compounds represented by the formula (I-4) are obtained.

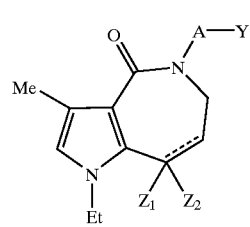

(I-4)

wherein the dashed line, A, Y, $Z_1$ and $Z_2$ have the same meanings as defined above.

(107) 1-Ethyl-5-[3-[4-(6-fluoro-1,2-benzisoxazol-3-yl)piperidino]propyl]-3-methyl-1,4,5,6,7,8-hexahydropyrrolo[3,2-c]azepin-4-one-8-spiro-2'-(1',3'-dithiolane)

(108) 1-Ethyl-5-[3-[4-(4-fluorophenyl)piperazin-1-yl]propyl]-3-methyl-1,4,5,6,7,8-hexahydropyrrolo[3,2-c]azepin-4-one-8-spiro-2'-(1',3'-dithiane)

(109) 1-Ethyl-5-[3-[4-(4-fluorophenyl)piperazin-1-yl]propyl]-8-hydroxy-3-methyl-1,4,5,6,7,8-hexahydropyrrolo[3,2-c]azepin-4-one (110) 1-Ethyl-8-hydroxy-5-[3-[4-(4-hydroxyphenyl)piperazin-1-yl]propyl]-3-methyl-1,4,5,6,7,8-hexahydropyrrolo[3,2-c]azepin-4-one (111) 1-Ethyl-8-hydroxy-3-methyl-5-[3-(4-phenylpiperazin-1-yl)propyl]-1,4,5,6,7,8-hexahydropyrrolo[3,2-c]azepin-4-one (112) 5-[3-[4-(4-chlorophenyl)piperazin-1-yl]propyl]-1-ethyl-8-hydroxy-3-methyl-1,4,5,6,7,8-hexahydropyrrolo[3,2-c]azepin-4-one (113) 1-Ethyl-5-[3-[4-(6-fluoro-1,2-benzisoxazol-3-yl)piperidino]propyl]-8-hydroxy-3-methyl-1,4,5,6,7,8-hexahydropyrrolo[3,2-c]azepin-4-one (114) 1-Ethyl-5-[3-[4-(4-fluorophenyl)piperazin-1-yl]propyl]-8-methoxy-3-methyl-1,4,5,6,7,8-hexahydropyrrolo[3,2-c]azepin-4-one (115) 1-Ethyl-5-[4-[4-(4-fluorophenyl)piperazin-1-yl]butyl]-8-methoxy-3-methyl-1,4,5,6,7,8-hexahydropyrrolo[3,2-c]azepin-4-one (116) 5-[3-[4-(4-chlorophenyl)piperazin-1-yl]propyl]-1-ethyl-8-methoxy-3-methyl-1,4,5,6,7,8-hexahydropyrrolo[3,2-c]azepin-4-one (117) 1-Ethyl-5-[3-[4-(6-fluoro-1,2-benzisoxazol-3-yl)piperidino]propyl]-8-methoxy-3-methyl-1,4,5,6,7,8-hexahydropyrrolo[3,2-c]azepin-4-one (118) 1-Ethyl-5-[3-[4-(4-fluorophenyl)piperazin-1-yl]propyl]-3-methyl-1,4,5,6-tetrahydropyrrolo-[3,2-c]azepin-4-one (119) 1-Ethyl-5-[3-[4-(4-hydroxyphenyl)piperazin-1-yl]propyl]-3-methyl-1,4,5,6-tetrahydropyrrolo-[3,2-c]azepin-4-one (120) 1-Ethyl-3-methyl-5-[3-(4-phenylpiperazin-1-yl)propyl]-1,4,5,6-tetrahydropyrrolo[3,2-c]azepin-4-one (121) 5-[3-[4-(4-chlorophenyl)piperazin-1-yl]propyl]-1-ethyl-3-methyl-1,4,5,6-tetrahydropyrrolo-[3,2-c]azepin-4-one (122) 1-Ethyl-5-[3-[4-(6-fluoro-1,2-benzisoxazol-3-yl)piperidino]propyl]-3-methyl-1,4,5,6-tetrahydropyrrolo[3,2-c]azepin-4-one (123) 1-Ethyl-5-[3-[4-(4-fluorophenyl)piperazin-1-yl]propyl]-3-methyl-1,4,5,6,7,8-hexahydropyrrolo[3,2-c]azepin-4-one (124) 1-Ethyl-5-[3-[4-(4-hydroxyphenyl)piperazin-1-yl]propyl]-3-methyl-1,4,5,6,7,8-hexahydropyrrolo[3,2-c]azepin-4-one (125) 1-Ethyl-3-methyl-5-[3-(4-phenylpiperazin-1-yl)propyl]-1,4,5,6,7,8-hexahydropyrrolo[3,2-c]azepin-4-one (126) 5-[3-[4-(4-chlorophenyl)piperazin-1-yl]propyl]-1-ethyl-3-methyl-1,4,5,6,7,8-hexahydropyrrolo[3,2-c]azepin-4-one (127) 1-Ethyl-5-[3-[4-(6-fluoro-1,2-benzisoxazol-3-yl)piperidino]propyl]-3-methyl-1,4,5,6,7,8-hexahydropyrrolo[3,2-c]azepin-4-one

EXAMPLE 92

In the same manner or a similar manner as in any of Examples 1–87 described above, the following compounds represented by the formula (I-5) are obtained.

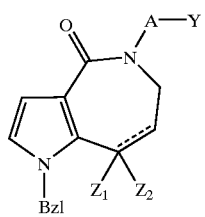

(I-5)

wherein the dashed line, A, Y, $Z_1$ and $Z_2$ have the same meanings as defined above.

(128) 1-Benzyl-5-[3-[4-(4-fluorophenyl)piperazin-1-yl]propyl]-1,4,5,6,7,8-hexahydropyrrolo[3,2-c]azepin-4-one-8-spiro-2'-(1',3'-dithiolane)

(129) 1-Benzyl-8,8-bis(ethylthio)-5-[3-[4-(6-fluoro-1,2-benzisoxazol-3-yl)piperidino]propyl]-1,4,5,6,7,8-hexahydropyrrolo[3,2-c]azepin-4-one (130) 1-Benzyl-8-hydroxy-5-[3-[4-(4-hydroxyphenyl)piperazin-1-yl]propyl]-1,4,5,6,7,8-hexahydropyrrolo[3,2-c]azepin-4-one (131) 1-Benzyl-8-hydroxy-5-[3-(4-phenylpiperazin-1-yl)propyl]-1,4,5,6,7,8-hexahydropyrrolo[3,2-c]azepin-4-one (132) 1-Benzyl-5-[3-[4-(4-chlorophenyl)piperazin-1-yl]propyl]-8-hydroxy-1,4,5,6,7,8-hexahydropyrrolo[3,2-c]azepin-4-one (133) 1-Benzyl-5-[3-[4-(6-fluoro-1,2-benzisoxazol-3-yl)piperidino]propyl]-8-hydroxy-1,4,5,6,7,8-hexahydropyrrolo[3,2-c]azepin-4-one (134) 1-Benzyl-5-[3-[4-(4-fluorophenyl)piperazin-1-yl]propyl]-8-methoxy-1,4,5,6,7,8-hexahydropyrrolo[3,2-c]azepin-4-one (135) 1-Benzyl-5-[3-[4-(4-hydroxyphenyl)piperazin-1-yl]propyl]-8-methoxy-1,4,5,6,7,8-hexahydropyrrolo[3,2-c]azepin-4-one (136) 1-Benzyl-8-methoxy-5-[3-(4-phenylpiperazin-1-yl)propyl]-1,4,5,6,7,8-hexahydropyrrolo[3,2-c]azepin-4-one (137) 1-Benzyl-5-[3-[4-(4-chlorophenyl)piperazin-1-yl]propyl]-8-methoxy-1,4,5,6,7,8-hexahydropyrrolo[3,2-c]azepin-4-one (138) 1-Benzyl-5-[3-[4-(6-fluoro-1,2-benzisoxazol-3-yl)piperidino]propyl]-8-methoxy-1,4,5,6,7,8-hexahydropyrrolo[3,2-c]azepin-4-one (139) 1-Benzyl-8-ethoxy-5-[3-[4-(4-methoxyphenyl)piperazin-1-yl]propyl]-1,4,5,6,7,8-hexahydropyrrolo[3,2-c]azepin-4-one (140) 1-Benzyl-8-benzyloxy-5-[3-[4-(4-fluorophenyl)piperazin-1-yl]propyl]-1,4,5,6,7,8-hexahydropyrrolo[3,2-c]azepin-4-one (141) 1-Benzyl-5-[3-[4-(4-fluorophenyl)piperazin-1-yl]propyl]-1,4,5,6-tetrahydropyrrolo[3,2-c]azepin-4-one (142) 1-Benzyl-5-[3-[4-(4-hydroxyphenyl)piperazin-1-yl]propyl]-1,4,5,6-tetrahydropyrrolo[3,2-c]azepin-4-one (143) 1-Benzyl-5-[3-(4-phenylpiperazin-1-yl)propyl]-1,4,5,6-tetrahydropyrrolo[3,2-c]azepin-4-one (144) 1-Benzyl-5-[3-[4-(4-chlorophenyl)piperazin-1-yl]propyl]-1,4,5,6-tetrahydropyrrolo[3,2-c]azepin-4-one (145) 1-Benzyl-5-[3-[4-(6-fluoro-1,2-benzisoxazol-3-yl)piperidino]propyl]-1,4,5,6-tetrahydropyrrolo-[3,2-c]azepin-4-one (146) 1-Benzyl-5-[3-[4-(4-fluorophenyl)piperazin-1-yl]propyl]-1,4,5,6,7,8-hexahydropyrrolo[3,2-c]azepin-4-one (147) 1-Benzyl-5-[3-[4-(4-hydroxyphenyl)piperazin-1-yl]propyl]-1,4,5,6,7,8-hexahydropyrrolo[3,2-c]azepin-4-one (148) 1-Benzyl-5-[3-(4-phenylpiperazin-1-yl)propyl]-1,4,5,6,7,8-hexahydropyrrolo[3,2-c]azepin-4-one (149) 1-Benzyl-5-[3-[4-(4-chlorophenyl)piperazin-1-yl]propyl]-1,4,5,6,7,8-hexahydropyrrolo[3,2-c]azepin-4-one (150) 1-Benzyl-5-[3-[4-(6-fluoro-1,2-benzisoxazol-3-yl)piperidino]propyl]-1,4,5,6,7,8-hexahydropyrrolo[3,2-c]azepin-4-one

EXAMPLE 93

In the same manner or a similar manner as in any of Examples 1–87 described above, the following compounds represented by the formula (I-6) are obtained:

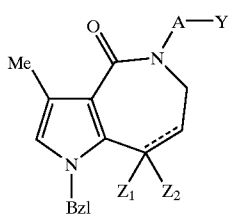

wherein the dashed line, A, Y, $Z_1$ and $Z_2$ have the same meanings as defined above.

(151) 1-Benzyl-5-[3-[4-(4-chlorophenyl)piperazin-1-yl]propyl]-8,8-bis(ethylthio)-3-methyl-1,4,5,6,7,8-hexahydropyrrolo[3,2-c]azepin-4-one (152) 1-Benzyl-5-[3-[4-(4-fluorophenyl)piperazin-1-yl]propyl]-8-hydroxy-3-methyl-1,4,5,6,7,8-hexahydropyrrolo[3,2-c]azepin-4-one (153) 1-Benzyl-8-hydroxy-5-[3-[4-(4-hydroxyphenyl)piperazin-1-yl]propyl]-3-methyl-1,4,5,6,7,8-hexahydropyrrolo[3,2-c]azepin-4-one (154) 1-Benzyl-8-hydroxy-3-methyl-5-[3-(4-phenylpiperazin-1-yl)propyl]-1,4,5,6,7,8-hexahydropyrrolo[3,2-c]azepin-4-one (155) 1-Benzyl-5-[3-[4-(4-chlorophenyl)piperazin-1-yl]propyl]-8-hydroxy-3-methyl-1,4,5,6,7,8-hexahydropyrrolo[3,2-c]azepin-4-one (156) 1-Benzyl-5-[3-[4-(6-fluoro-1,2-benzisoxazol-3-yl)piperidino]propyl]-8-hydroxy-3-methyl-1,4,5,6,7,8-hexahydropyrrolo[3,2-c]azepin-4-one (157) 1-Benzyl-5-[3-[4-(4-fluorophenyl)piperazin-1-yl]propyl]-8-methoxy-3-methyl-1,4,5,6,7,8-hexahydropyrrolo[3,2-c]azepin-4-one (158) 1-Benzyl-5-[3-[4-(4-hydroxyphenyl)piperazin-1-yl]propyl]-8-methoxy-3-methyl-1,4,5,6,7,8-hexahydropyrrolo[3,2-c]azepin-4-one (159) 1-Benzyl-8-methoxy-3-methyl-5-[3-(4-phenylpiperazin-1-yl)propyl]-1,4,5,6,7,8-hexahydropyrrolo[3,2-c]azepin-4-one (160) 1-Benzyl-5-[3-[4-(4-chlorophenyl)piperazin-1-yl]propyl]-8-methoxy-3-methyl-1,4,5,6,7,8-hexahydropyrrolo[3,2-c]azepin-4-one (161) 1-Benzyl-8-ethoxy-5-[3-[4-(6-fluoro-1,2-benzisoxazol-3-yl)piperidino]propyl]-3-methyl-1,4,5,6,7,8-hexahydropyrrolo[3,2-c]azepin-4-one (162) 1-Benzyl-5-[3-[4-(4-fluorophenyl)piperazin-1-yl]propyl]-3-methyl-1,4,5,6-tetrahydropyrrolo-[3,2-c]azepin-4-one (163) 1-Benzyl-5-[3-[4-(4-hydroxyphenyl)piperazin-1-yl]propyl]-3-methyl-1,4,5,6-tetrahydropyrrolo-[3,2-c]azepin-4-one (164) 1-Benzyl-3-methyl-5-[3-(4-phenylpiperazin-1-yl)propyl]-1,4,5,6-tetrahydropyrrolo[3,2-c]azepin-4-one (165) 1-Benzyl-5-[3-[4-(4-chlorophenyl)piperazin-1-yl]propyl]-3-methyl-1,4,5,6-tetrahydropyrrolo-[3,2-c]azepin-4-one (166) 1-Benzyl-5-[3-[4-(6-fluoro-1,2-benzisoxazol-3-yl)piperidino]propyl]-3-methyl-1,4,5,6-tetrahydropyrrolo[3,2-c]azepin-4-one (167) 1-Benzyl-5-[3-[4-(4-fluorophenyl)piperazin-1-yl]propyl]-3-methyl-1,4,5,6,7,8-hexahydropyrrolo[3,2-c]azepin-4-one (168) 1-Benzyl-5-[3-[4-(4-hydroxyphenyl)piperazin-1-yl]propyl]-3-methyl-1,4,5,6,7,8-hexahydropyrrolo[3,2-c]azepin-4-one (169) 1-Benzyl-3-methyl-5-[3-(4-phenylpiperazin-1-yl)propyl]-1,4,5,6,7,8-hexahydropyrrolo[3,2-c]azepin-4-one (170) 1-Benzyl-5-[3-[4-(4-chlorophenyl)piperazin-1-yl]propyl]-3-methyl-1,4,5,6,7,8-hexahydropyrrolo[3,2-c]azepin-4'-one (171) 1-Benzyl-5-[3-[4-(6-fluoro-1,2-benzisoxazol-3-yl)piperidino]propyl]-3-methyl-1,4,5,6,7,8-hexahydropyrrolo[3,2-c]azepin-4-one

EXAMPLE 94

In the same manner or a similar manner as in any of Examples 1–87 described above, the following compounds represented by the formula (I-7) are obtained:

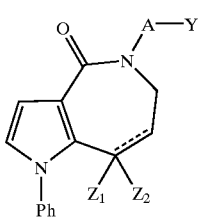

wherein the dashed line, A, Y, $Z_1$ and $Z_2$ have the same meanings as defined above.

(172) 5-[3-[4-(4-Chlorophenyl)piperazin-1-yl]propyl]-1-phenyl-1,4,5,6,7,8-hexahydropyrrolo[3,2-c]azepin-4-one-8-spiro-2'-(1',3'-dithiolane)

(173) 8-Hydroxy-5-[3-[4-(4-hydroxyphenyl)piperazin-1-yl]propyl]-1-phenyl-1,4,5,6,7,8-hexahydropyrrolo[3,2-c]azepin-4-one (174) 8-Hydroxy-1-phenyl-5-[3-(4-phenylpiperazin-1-yl)propyl]-1,4,5,6,7,8-hexahydropyrrolo[3,2-c]azepin-4-one (175) 5-[3-[4-(4-Chlorophenyl)piperazin-1-yl]propyl]-8-hydroxy-1-phenyl-1,4,5,6,7,8-hexahydropyrrolo-[3,2-c]azepin-4-one (176) 5-[3-[4-(6-Fluoro-1,2-benzisoxazol-3-yl)piperidino]propyl]-8-hydroxy-1-phenyl-1,4,5,6,7,8-hexahydropyrrolo[3,2-c]azepin-4-one (177) 5-[3-[4-(4-Fluorophenyl)piperazin-1-yl]propyl]-8-methoxy-1-phenyl-1,4,5,6,7,8-hexahydropyrrolo-[3,2-c]azepin-4-one (178) 5-[3-[4-(4-Hydroxyphenyl)piperazin-1-yl]propyl]-8-methoxy-1-phenyl-1,4,5,6,7,8-hexahydropyrrolo-[3,2-c]azepin-4-one (179) 8-Methoxy-1-phenyl-5-[3-(4-phenylpiperazin-1-yl)propyl]-1,4,5,6,7,8-hexahydropyrrolo[3,2-c]azepin-4-one (180) 5-[3-[4-(4-Chlorophenyl)piperazin-1-yl]propyl]-8-methoxy-1-phenyl-1,4,5,6,7,8-hexahydropyrrolo-[3,2-c]azepin-4-one (181) 5-[3-[4-(6-Fluoro-1,2-benzisoxazol-3-yl)piperidino]propyl]-8-methoxy-1-phenyl-1,4,5,6,7,8-hexahydropyrrolo[3,2-c]azepin-4-one (182) 5-[3-[4-(4-Fluorophenyl)piperazin-1-yl]propyl]-1-phenyl-1,4,5,6-tetrahydropyrrolo[3,2-c]azepin-4-one (183) 5-[3-[4-(4-Hydroxyphenyl)piperazin-1-yl]propyl]-1-phenyl-1,4,5,6-tetrahydropyrrolo[3,2-c]azepin-4-one (184) 1-Phenyl-5-[3-(4-phenylpiperazin-1-yl)propyl]-1,4,5,6-tetrahydropyrrolo[3,2-c]azepin-4-one (185) 5-[3-[4-(4-Chlorophenyl)piperazin-1-yl]propyl]-1-phenyl-1,4,5,6-tetrahydropyrrolo[3,2-c]azepin-4-one (186) 5-[3-[4-(6-Fluoro-1,2-benzisoxazol-3-yl)piperidino]propyl]-1-phenyl-1,4,5,6-tetrahydropyrrolo[3,2-c]azepin-4-one (187) 5-[3-[4-(4-Fluorophenyl)piperazin-1-yl]propyl]-1-phenyl-1,4,5,6,7,8-hexahydropyrrolo[3,2-c]azepin-4-one (188) 5-[3-[4-(4-Hydroxyphenyl)piperazin-1-yl]propyl]-1-phenyl-1,4,5,6,7,8-hexahydropyrrolo[3,2-c]azepin-4-one (189) 1-Phenyl-5-[3-(4-phenylpiperazin-1-yl)propyl]-1,4,5,6,7,8-hexahydropyrrolo[3,2-c]azepin-4-one (190) 5-[3-[4-(4-Chlorophenyl)piperazin-1-yl]propyl]-1-phenyl-1,4,5,6,7,8-hexahydropyrrolo[3,2-c]azepin-4-one (191) 5-[3-[4-(6-Fluoro-1,2-benzisoxazol-3-yl)piperidino]propyl]-1-phenyl-1,4,5,6,7,8-hexahydropyrrolo[3,2-c]azepin-4-one

EXAMPLE 95

In the same manner or a similar manner as in any of Examples 1–87 described above, the following compounds represented by the formula (I-8) are obtained.

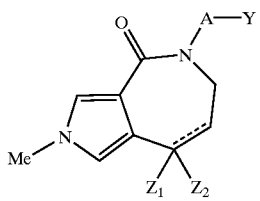

(I-8)

wherein the dashed line, A, Y, $Z_1$ and $Z_2$ have the same meanings as defined above.

(192) 5-[3-[4-(4-Fluorophenyl)piperazin-1-yl]propyl]-2-methyl-2,4,5,6,7,8-hexahydropyrrolo[3,4-c]azepin-4-one-8-spiro-2'-(1',3'-dithiolane)

(193) 8-Hydroxy-5-[3-[4-(4-hydroxyphenyl)piperazin-1-yl]propyl]-2-methyl-2,4,5,6,7,8-hexahydropyrrolo[3,4-c]azepin-4-one (194) 8-Hydroxy-2-methyl-5-[3-(4-phenylpiperazin-1-yl)propyl]-2,4,5,6,7,8-hexahydropyrrolo[3,4-c]azepin-4-one (195) 5-[3-[4-(4-Chlorophenyl)piperazin-1-yl]propyl]-8-hydroxy-2-methyl-2,4,5,6,7,8-hexahydropyrrolo-[3,4-c]azepin-4-one (196) 5-[3-[4-(6-Fluoro-1,2-benzisoxazol-3-yl)piperidino]propyl]-8-hydroxy-2-methyl-2,4,5,6,7,8-hexahydropyrrolo[3,4-c]azepin-4-one (197) 5-[3-[4-(4-Fluorophenyl)piperazin-1-yl]propyl]-8-methoxy-2-methyl-2,4,5,6,7,8-hexahydropyrrolo-[3,4-c]azepin-4-one (198) 5-[3-[4-(4-Hydroxyphenyl)piperazin-1-yl]propyl]-8-methoxy-2-methyl-2,4,5,6,7,8-hexahydropyrrolo-[3,4-c]azepin-4-one (199) 8-Methoxy-2-methyl-5-[3-(4-phenylpiperazin-1-yl)propyl]-2,4,5,6,7,8-hexahydropyrrolo[3,4-c]azepin-4-one (200) 5-[3-[4-(4-Chlorophenyl)piperazin-1-yl]propyl]-8-methoxy-2-methyl-2,4,5,6,7,8-hexahydropyrrolo-[3,4-c]azepin-4-one (201) 8-Ethoxy-5-[3-[4-(6-fluoro-1,2-benzisoxazol-3-yl)piperidino]propyl]-2-methyl-2,4,5,6,7,8-hexahydropyrrolo[3,4-c]azepin-4-one (202) 5-[3-[4-(4-Fluorophenyl)piperazin-1-yl]propyl]-2-methyl-2,4,5,6-tetrahydropyrrolo[3,4-c]azepin-4-one (203) 5-[3-[4-(4-Hydroxyphenyl)piperazin-1-yl]propyl]-2-methyl-2,4,5,6-tetrahydropyrrolo[3,4-c]azepin-4-one (204) 2-Methyl-5-[3-(4-phenylpiperazin-1-yl)propyl]-2,4,5,6-tetrahydropyrrolo[3,4-c]azepin-4-one (205) 5-[3-[4-(4-Chlorophenyl)piperazin-1-yl]propyl]-2-methyl-2,4,5,6-tetrahydropyrrolo[3,4-c]azepin-4-one (206) 5-[3-[4-(6-Fluoro-1,2-benzisoxazol-3-yl)piperidino]propyl]-2-methyl-2,4,5,6-tetrahydropyrrolo[3,4-c]azepin-4-one (207) 5-[3-[4-(4-Fluorophenyl)piperazin-1-yl]propyl]-2-methyl-2,4,5,6,7,8-hexahydropyrrolo[3,4-c]azepin-4-one (208) 5-[3-[4-(4-Hydroxyphenyl)piperazin-1-yl]propyl]-2-methyl-2,4,5,6,7,8-hexahydropyrrolo[3,4-c]azepin-4-one (209) 2-Methyl-5-[3-(4-phenylpiperazin-1-yl)propyl]-2,4,5,6,7,8-hexahydropyrrolo[3,4-c]azepin-4-one (210) 5-[3-[4-(4-Chlorophenyl)piperazin-1-yl]propyl]-2-methyl-2,4,5,6,7,8-hexahydropyrrolo[3,4-c]azepin-4-one (211) 5-[3-[4-(6-Fluoro-1,2-benzisoxazol-3-yl)piperidino]propyl]-2-methyl-2,4,5,6,7,8-hexahydropyrrolo[3,4-c]azepin-4-one

EXAMPLE 96

In the same manner or a similar manner as in any of Examples 1–87 described above, the following compounds represented by the formula (I-9) are obtained.

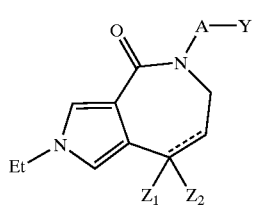

(I-9)

wherein the dashed line, A, Y, $Z_1$ and $Z_2$ have the same meanings as defined above.

(212) 2-Ethyl-5-[3-[4-(4-fluorophenyl)piperazin-1-yl]propyl]-8-hydroxy-2,4,5,6,7,8-hexahydropyrrolo[3,4-c]azepin-4-one (213) 2-Ethyl-8-hydroxy-5-[3-[4-(4-hydroxyphenyl)piperazin-1-yl]propyl]-2,4,5,6,7,8-hexahydropyrrolo[3,4-c]azepin-4-one (214) 2-Ethyl-8-hydroxy-5-[3-(4-phenylpiperazin-1-yl)propyl]-2,4,5,6,7,8-hexahydropyrrolo[3,4-c]azepin-4-one (215) 5-[3-[4-(4-Chlorophenyl)piperazin-1-yl]propyl]-2-ethyl-8-hydroxy-2,4,5,6,7,8-hexahydropyrrolo-[3,4-c]azepin-4-one (216) 2-Ethyl-5-[3-[4-(4-Fluorophenyl)piperazin-1-yl]propyl]-8-methoxy-2,4,5,6,7,8-hexahydropyrrolo[3,4-c]azepin-4-one (217) 2-Ethyl-5-[3-[4-(4-fluorophenyl)piperazin-1-yl]propyl]-2,4,5,6-tetrahydropyrrolo[3,4-c]azepin-4-one (218) 2-Ethyl-5-[3-[4-(4-hydroxyphenyl)piperazin-1-yl]propyl]-2,4,5,6-tetrahydropyrrolo[3,4-c]azepin-4-one (219) 2-Ethyl-5-[3-[4-(6-fluoro-1,2-benzisoxazol-3-yl)piperidino]propyl]-2,4,5,6-tetrahydropyrrolo-[3,4-c]azepin-4-one (220) 2-Ethyl-5-[3-[4-(4-fluorophenyl)piperazin-1-yl]propyl]-2,4,5,6,7,8-hexahydropyrrolo[3,4-c]azepin-4-one (221) 2-Ethyl-5-[3-[4-(4-hydroxyphenyl)piperazin-1-yl]propyl]-2,4,5,6,7,8-hexahydropyrrolo[3,4-c]azepin-4-one (222) 2-Ethyl-5-[3-(4-phenylpiperazin-1-yl)propyl]-2,4,5,6,7,8-hexahydropyrrolo[3,4-c]azepin-4-one (223) 5-[3-[4-(4-Chlorophenyl)piperazin-1-yl]propyl]-2-ethyl-2,4,5,6,7,8-hexahydropyrrolo[3,4-c]azepin-4-one (224) 2-Ethyl-5-[3-[4-(6-fluoro-1,2-benzisoxazol-3-yl)piperidino]propyl]-2,4,5,6,7,8-hexahydropyrrolo[3,4-c]azepin-4-one

EXAMPLE 97

In the same manner or a similar manner as in any of Examples 1–87 described above, the following compounds represented by the formula (I-10) are obtained.

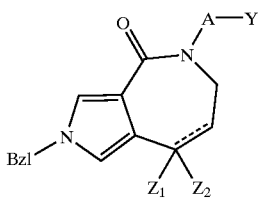

(I-10)

wherein the dashed line, A, Y, $Z_1$ and $Z_2$ have the same meanings as defined above.

(225) 2-Benzyl-5-[3-[4-(4-fluorophenyl)piperazin-1-yl]propyl]-8-hydroxy-2,4,5,6,7,8-hexahydropyrrolo[3,4-c]azepin-4-one (226) 2-Benzyl-8-hydroxy-5-[3-[4-(4-hydroxyphenyl)piperazin-1-yl]propyl]-2,4,5,6,7,8-hexahydropyrrolo[3,4-c]azepin-4-one (227) 2-Benzyl-5-[3-[4-(6-fluoro-1,2-benzisoxazol-3-yl)piperidino]propyl]-8-hydroxy-2,4,5,6,7,8-hexahydropyrrolo[3,4-c]azepin-4-one (228) 2-Benzyl-5-[3-[4-(4-fluorophenyl)piperazin-1-yl]propyl]-8-methoxy-2,4,5,6,7,8-hexahydropyrrolo[3,4-c]azepin-4-one (229) 2-Benzyl-5-[3-[4-(4-fluorophenyl)piperazin-1-yl]propyl]-2,4,5,6-tetrahydropyrrolo[3,4-c]azepin-4-one (230) 2-Benzyl-5-[3-[4-(4-hydroxyphenyl)piperazin-1-yl]propyl]-2,4,5,6-tetrahydropyrrolo[3,4-c]azepin-4-one (231) 2-Benzyl-5-[3-(4-phenylpiperazin-1-yl)propyl]-2,4,5,6-tetrahydropyrrolo[3,4-c]azepin-4-one (232) 2-Benzyl-5-[3-[4-(4-chlorophenyl)piperazin-1-yl]propyl]-2,4,5,6-tetrahydropyrrolo[3,4-c]azepin-4-one (233) 2-Benzyl-5-[3-[4-(4-fluorophenyl)piperazin-1-yl]propyl]-2,4,5,6,7,8-hexahydropyrrolo(3,4-c]azepin-4-one (234) 2-Benzyl-5-[3-[4-(4-hydroxyphenyl)piperazin-1-yl]propyl]-2,4,5,6,7,8-hexahydropyrrolo[3,4-c]azepin-4-one (235) 2-Benzyl-5-[3-[4-(6-fluoro-1,2-benzisoxazol-3-yl)piperidino]propyl]-2,4,5,6,7,8-hexahydropyrrolo[3,4-c]azepin-4-one

EXAMPLE 98

In the same manner or a similar manner as in any of Examples 1–87 described above, the following compounds represented by the formula (I-11) are obtained.

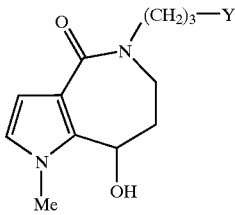

(I-11)

wherein Y has the same meanings as defined above.

(236) 5-[3-[4-(2-Furoyl)piperazin-1-yl)propyl]-8-hydroxy-1-methyl-1,4,5,6,7,8-hexahydropyrrolo-[3,2-c]azepin-4-one (237) 5-[3-[4-[Bis(4-fluorophenyl)hydroxymethyl]-piperidino]propyl]-8-hydroxy-1-methyl-1,4,5,6,7,8-hexahydropyrrolo[3,2-c]azepin-4-one (238) 5-[3-[4-(6-Fluoro-1,2-benzisothiazol-3-yl)piperidino]propyl]-8-hydroxy-1-methyl-1,4,5,6,7,8-hexahydropyrrolo[3,2-c]azepin-4-one (239) 5-[3-[4-(6-Fluoro-1H-indazol-3-yl)piperidino]-propyl]-8-hydroxy-1-methyl-1,4,5,6,7,8-hexahydropyrrolo[3,2-c]azepin-4-one (240) 5-[3-[3-(4-Fluorobenzoyl)pyrrolidin-1-yl]-propyl]-8-hydroxy-1-methyl-1,4,5,6,7,8-hexahydropyrrolo[3,2-c]azepin-4-one (241) 5-[3-[4-(4-Fluorophenoxy)piperidino]propyl]-8-hydroxy-1-methyl-1,4,5,6,7,8-hexahydropyrrolo-[3,2-c]azepin-4-one (242) 5-[3-[4-[Bis(4-fluorophenyl)methylene]-piperidino]propyl]-8-hydroxy-1-methyl-1,4,5,6,7,8-hexahydropyrrolo[3,2-c]azepin-4-one (243) 5-[3-[4-[2-(4-Fluorophenyl)-1,3-dioxolan-2-yl]-piperidino]propyl]-8-hydroxy-1-methyl-1,4,5,6,7,8-hexahydropyrrolo[3,2-c]azepin-4-one Test With respect to the compounds of the present invention, their anti-serotonin (5-HT) action and anti-$\alpha_1$ action were investigated by the methods which will be described below. The results of some representative compounds are shown in Table 22.

(1) Anti-Serotonin (5-HT) Action

The superior mesenteric artery of each Hartley male guinea pig (body weight: 300–500 g) was excised. A preparation cut in a helical form was suspended under resting tension of 0.3 g in a Magnus cylinder filled with the Tyrode solution which had been aerated with a gas mixture of 95% $O_2$ and 5% $CO_2$ and maintained at 37° C. Using an isometric transducer ("UL-10", manufactured by SHINKOH K.K.) and a pressure preamplifier ("DSA-605A", manufactured by SHINKOH K.K.), variations in tension were measured. The isometric tensions were recorded on a pen-writing recorder ("VP-6537A", manufactured by NATIONAL K.K.). Taking the contraction induced by $10^{-5}$ M serotonin (5-HT) as 100%, the percent contractions by $10^{-5}$ M 5-HT in the presence of each test drug at $10^{-8}$ M, $10^{-7}$ M and $10^{-6}$ M were determined as anti-5-HT action.

(2) Anti-$\alpha_1$ Action

The thoracic aorta of each Hartley male guinea pig (body weight: 300–500 g) was excised. A preparation cut in a helical form was suspended under 1 g load in a Magnus cylinder filled with the Tyrode solution which had been aerated with a gas mixture of 95% $O_2$ and 5% $CO_2$ and maintained at 37° C. Using an isometric transducer ("TB-612J", manufactured by Nihon Kohden Corporation) and a pressure preamplifier ("AP-620G", manufactured by Nihon Kohden Corporation), variations in tension were measured. The isometric tensions were recorded on a thermal pen-writing recorder ("WT-647G", manufactured by Nihon Kohden Corporation). Taking the tonic contraction induced by $10^{-5}$ M norepinephrine (NE) as 100%, the percent contractions upon addition of each test drug at $10^{-8}$ M and $10^{-7}$ M were determined as $\alpha_1$ action.

(Results)

TABLE 22

| Comp'd No. | Anti 5-HT action (% of Control) | | | Anti $\alpha_1$ action (% of Control) | |
|---|---|---|---|---|---|
| | $10^{-8}$M | $10^{-7}$M | $10^{-6}$M | $10^{-8}$M | $10^{-7}$M |
| 50 | 67.5 | 25.1 | NT | 67.1 | 34.2 |
| 52* | 75.5 | 20.9 | NT | 96.8 | 75.8 |
| 53 | NT | 87.1 | 48.2 | 86.1 | 60.1 |
| 55 | NT | 59.5 | 11.0 | 97.6 | 73.5 |
| 56 | NT | 90.2 | 47.9 | 96.7 | 71.4 |
| 57 | 54.6 | 12.0 | 7.5 | 100 | 91.4 |
| 59 | 48.5 | 12.5 | NT | 81.6 | 47.3 |
| 61 | NT | 74.3 | 37.3 | 96.1 | 39.4 |
| 62 | NT | 50.6 | 11.1 | 95.0 | 31.7 |
| 73 | 90.7 | 54.7 | 14.9 | 99.3 | 94.0 |
| 75 | NT | 71.7 | 25.2 | 98.3 | 70.3 |
| 76 | NT | 35.5 | 7.2 | 98.9 | 88.1 |
| 79 | 78.3 | 31.8 | NT | 94.8 | 58.1 |
| 82 | 35.2 | 8.4 | NT | 87.6 | 37.6 |
| 83 | 42.0 | 8.7 | NT | 99.9 | 93.0 |
| 84 | 82.0 | 61.9 | 11.9 | 100 | 92.4 |

NT Not tested.
*The compound in the form of the dihydrochloride was used as the test compound.

Capability of Exploitation in Industry

The pyrroloazepine derivatives (I) and their salts according to the present invention have strong serotonin-2 blocking action and have high safety. Accordingly, the present invention has made it possible to provide pharmaceuticals making use of antagonistic action against serotonin-2 receptors, for example, therapeutics for various circulatory diseases such as ischemic heart diseases, cerebrovascular disturbances and peripheral circulatory disturbances. Further, the compounds according to the present invention include those also having al blocking action in combination. Since these compounds are also effective as antihypertensives, they are extremely used for therapeutics for a wide variety of circulatory diseases.

What is claimed is:
1. A compound having the formula (XXIII):

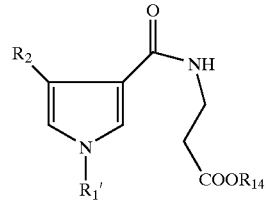

(XXIII)

wherein $R_1'$ is hydrogen, alkyl, cycloalkyl, cycloalkyl-alkyl, optionally substituted aralkyl or aryl; $R_2$ is hydrogen or alkyl; and $R_{14}$ is hydrogen or a carboxyl-protecting group.

2. A compound having the formula (XXV):

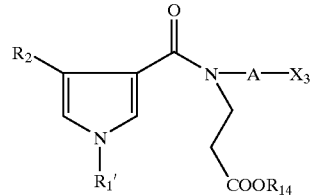

(XXV)

wherein A is alkylene, alkenylene or alkynylene; $R_1'$ is hydrogen, alkyl, cycloalkyl, cycloalkyl-alkyl, optionally substituted aralkyl or aryl; $R_2$ is hydrogen or alkyl; $R_{14}$ is hydrogen or carboxyl-protecting group; and $X_3$ is chlorine or bromine.

3. The compound of claim 1, wherein $R_1'$ is hydrogen.

4. The compound of claim 1, wherein $R_1'$ is $C_1$–$C_8$ linear or branched alkyl.

5. The compound of claim 1, wherein $R_1'$ is $C_3$–$C_8$ cycloalkyl.

6. The compound of claim 1, wherein $R_1'$ is $C_4$–$C_8$ cycloalkyl-alkyl.

7. The compound of claim 1, wherein $R_1'$ is $C_7$–$C_{22}$ aralkyl which is optionally substituted by halogen, $C_1$–$C_4$ alkyl, or $C_1$–$C_4$ alkoxy or a combination thereof.

8. The compound of claim 1, wherein $R_2$ is hydrogen.

9. The compound of claim 1, wherein $R_2$ is is $C_1$–$C_8$ linear or branched alkyl.

10. The compound of claim 1, wherein $R_{14}$ is hydrogen.

11. The compound of claim 1, wherein the carboxyl-protecting group $R_{14}$ is selected from the group consisting of methyl, ethyl, n-propyl, isopropyl, n-butyl, isobutyl, t-butyl, benzyl and 9-anthrylmethyl group.

12. The compound of claim 2, wherein the alkylene, alkenylene or alkynylene in A are selected from the group consisting of ethylene, trimethylene, tetramethylene, pentamethylene, octamethylene, 2-butenylene, 3-pentenylene, 2-butynylene, 3-pentynylene, which may optionally be substituted with one or more fluorine, chlorine and/or bromine atoms.

13. The compound of claim 2, wherein $R_1'$ is hydrogen.

14. The compound of claim 2, wherein $R_1'$ is $C_1$–$C_8$ linear or branched alkyl.

15. The compound of claim 2, wherein $R_1'$ is $C_3$–$C_8$ cycloalkyl.

16. The compound of claim 2, wherein $R_1'$ is $C_4$–$C_8$ cycloalkyl-alkyl.

17. The compound of claim 2, wherein $R_1'$ is $C_7$–$C_{22}$ aralkyl which is optionally substituted by halogen, $C_1$–$C_4$ alkyl, or $C_1$–$C_4$ alkoxy or a combination thereof.

18. The compound of claim 2, wherein $R_2$ is hydrogen.

19. The compound of claim 2, wherein $R_2$ is is $C_1$–$C_8$ linear or branched alkyl.

20. The compound of claim 2, wherein $R_{14}$ is hydrogen.

* * * * *